United States Patent
Tomczuk et al.

(10) Patent No.: US 8,894,970 B2
(45) Date of Patent: Nov. 25, 2014

(54) ARGINASE INHIBITORS AND METHODS OF USE THEREOF

(75) Inventors: Bruce Edward Tomczuk, Collegeville, PA (US); Gary Lee Olson, Mountainside, NJ (US); Richard Scott Pottorf, Belle Mead, NJ (US); Lijuan Jane Wang, Wildwood, MO (US); Bhaskara Rao Nallaganchu, Hillsborough, NJ (US); Yanqun Zhang, East Brunswick, NJ (US)

(73) Assignee: Corridor Pharmaceuticals, Inc., Towson, MD (US)

( * ) Notice: Subject to any disclaimer, the term of this patent is extended or adjusted under 35 U.S.C. 154(b) by 356 days.

(21) Appl. No.: 13/191,160

(22) Filed: Jul. 26, 2011

(65) Prior Publication Data

US 2012/0171116 A1    Jul. 5, 2012

Related U.S. Application Data

(60) Provisional application No. 61/428,894, filed on Dec. 31, 2010, provisional application No. 61/450,804, filed on Mar. 9, 2011.

(51) Int. Cl.

| | |
|---|---|
| *A61K 51/00* | (2006.01) |
| *A61M 36/14* | (2006.01) |
| *A61K 31/69* | (2006.01) |
| *C07F 5/02* | (2006.01) |
| *A61K 51/04* | (2006.01) |
| *A61K 49/00* | (2006.01) |

(52) U.S. Cl.
CPC ............... *A61K 31/69* (2013.01); *A61K 51/044* (2013.01); *A61K 49/0004* (2013.01); *C07F 5/02* (2013.01)
USPC ......... 424/1.69; 424/1.11; 424/1.65; 424/9.1; 514/1.1

(58) Field of Classification Search
CPC ... A61K 51/08; A61K 51/0497; A61K 51/00; A61K 51/04; A61K 51/041; A61K 51/044; A61K 51/0444; A61K 51/0446; A61K 51/0453; A61K 51/0459; A61K 51/0463; A61K 51/0465; A61K 51/0468; A61K 51/047; A61K 51/06; A61K 51/065; A61K 2123/00; A61K 2121/00; A61K 38/00; A61K 38/005; A61K 38/02; A61K 38/03; A61K 38/04; A61K 49/0002; A61K 49/0004; A61K 49/00; A61K 49/001; A61K 49/0013; A61K 49/0015; A61K 49/0017; A61K 49/0019; A61K 49/0021; A61K 49/005; A61K 31/00; A61K 31/69; C07F 5/02; C07F 5/00
USPC ............ 424/1.11, 1.65, 9.1, 9.2, 9.3, 9.4, 9.5, 424/9.6, 9.7, 9.8, 1.69; 514/1, 1.1; 530/300; 544/336, 98, 59, 105, 349; 546/255, 546/184, 133, 138, 139, 152; 548/560; 540/484

See application file for complete search history.

(56) References Cited

U.S. PATENT DOCUMENTS

| | | | |
|---|---|---|---|
| 4,483,853 A | | 11/1984 | Collins et al. |
| 5,792,769 A | * | 8/1998 | Lu et al. .................... 514/252.12 |
| 5,891,909 A | * | 4/1999 | Soll et al. ....................... 514/517 |
| 6,037,356 A | * | 3/2000 | Lu et al. ......................... 514/349 |
| 6,133,315 A | * | 10/2000 | Lu et al. ......................... 514/517 |
| 6,204,263 B1 | * | 3/2001 | Lu et al. ...................... 514/235.8 |
| 6,225,302 B1 | * | 5/2001 | Lu et al. ......................... 514/183 |
| 6,235,778 B1 | * | 5/2001 | Tomczuk et al. ............. 514/517 |
| 6,245,763 B1 | * | 6/2001 | Lu et al. ......................... 514/247 |
| 6,281,206 B1 | * | 8/2001 | Lu et al. ......................... 514/183 |
| 6,326,492 B1 | * | 12/2001 | Wang et al. ....................... 544/63 |
| 6,344,466 B2 | * | 2/2002 | Soll et al. ....................... 514/331 |
| 6,344,484 B1 | * | 2/2002 | Tomczuk et al. ............. 514/565 |
| 6,344,486 B1 | * | 2/2002 | Soll et al. ....................... 514/620 |
| 6,350,764 B2 | * | 2/2002 | Lu et al. ......................... 514/349 |
| 6,414,020 B2 | * | 7/2002 | Lu et al. ......................... 514/517 |
| 6,417,161 B1 | * | 7/2002 | Lu et al. ........................ 514/13.6 |
| 6,472,399 B2 | * | 10/2002 | Lu et al. .................... 514/255.05 |
| 6,476,016 B2 | * | 11/2002 | Wang et al. .............. 514/211.08 |
| 6,514,978 B2 | * | 2/2003 | Lu et al. .................... 514/255.06 |
| 6,518,310 B2 | * | 2/2003 | Tomczuk et al. ............. 514/613 |
| 6,521,663 B2 | * | 2/2003 | Pan et al. ....................... 514/518 |
| 6,566,379 B1 | * | 5/2003 | Lu et al. ......................... 514/345 |
| 6,635,637 B2 | * | 10/2003 | Wang et al. ................. 514/228.8 |
| 6,638,931 B1 | * | 10/2003 | Tomczuk et al. .......... 514/238.2 |
| 6,706,021 B2 | * | 3/2004 | Lu et al. ......................... 604/244 |
| 6,706,765 B2 | * | 3/2004 | Tomczuk et al. ............. 514/605 |
| 6,730,783 B2 | * | 5/2004 | Tomczuk et al. ............. 544/158 |
| 7,029,654 B2 | * | 4/2006 | Lu et al. ......................... 424/9.1 |
| 7,402,586 B2 | * | 7/2008 | Lu et al. ......................... 514/269 |
| 2004/0057926 A1 | | 3/2004 | Ochoa et al. |
| 2005/0176651 A1 | | 8/2005 | Madge et al. |
| 2007/0185060 A1 | | 8/2007 | Wang |
| 2010/0189644 A1 | | 7/2010 | Christianson et al. |

FOREIGN PATENT DOCUMENTS

| | | |
|---|---|---|
| WO | WO 2010/085797 | 7/2010 |
| WO | WO 2011/133653 | 10/2011 |

OTHER PUBLICATIONS

Busnel, O., et al., "Synthesis and evaluation of new omega-borono-alpha-amino acids as rat liver arginase inhibitors," *Bioorganic & Medicinal Chemistry*, 2005, 13(7):2373-2379.

(Continued)

*Primary Examiner* — D L Jones
(74) *Attorney, Agent, or Firm* — Saul Ewing LLP; Kathryn Doyle; Domingos J. Silva

(57) ABSTRACT

The present invention includes arginase enzyme inhibitors, compositions comprising these arginase inhibitors, and methods of treating or diagnosing conditions characterized either by abnormally high arginase activity or abnormally low nitric oxide levels in a mammal, comprising administering compositions of the invention to the mammal.

2 Claims, 13 Drawing Sheets

(56) References Cited

OTHER PUBLICATIONS

Moali, C., et al., "Recognition of alpha-Amino acids Bearing Various C:NOH Functions by Nitric Oxide Synthase and Arginase Involves Very Different Structural Determinants," *Biochemistry*, 2000, 39(38):8208-8218.

Collet, S., et al., "Synthesis and evaluation of omega-borono-alpha-amino acids as active-site probes of arginase and nitric oxide synthases," *J. Chem. Soc., Perkin Trans.* 1, 2000, 2:177-182.

Kabasawa, H., et al., "Divergent synthesis of N-hydroxy-l-indospicine, the carbon isostere of N-hydroxy-l-arginine, and N-hydroxy-I-homoarginine from l-glutamate," *ARKIVOC*, 2003, 8:180-187.

Hey, C., et al., "Inhibition of arginase in rat and rabbit alveolar macrophages by Nomega-hydroxy-D,L-indospicine, effects on L-arginine utilization by nitric oxide synthase," *British Journal of Pharmacology*, 1997, 121(3):395-400.

Reddy, V. J., et al., "Concise synthesis of omega-borono-alpha-amino acids," *Organic & Biomolecular Chemistry*, 2007, 5(6):889-891.

Colleluori, D., et al., "Classical and Slow-Binding Inhibitors of Human Type II Arginase," *Biochemistry*, 2001, 40:9356-9362.

International Search Report for PCT/US2010/022090, mailed Sep. 14, 2010.

\* cited by examiner

R = Boc, alkyl, aralkyl
aryl, heteroaryl 1. 10% citric acid THF
2. (Boc)₂O, DIEA
T̶H̶F̶ →

25 → 32

1. 1 N HCl/THF
2. (Boc)₂O, DIEA THF
3. TBSCl, DMAP →

25 → 32

A

B

C

A $R^3$ = Boc 47
    = Cbz 48
    = pNO$_2$Cbz 50

B

ARGINASE INHIBITORS AND METHODS OF USE THEREOF

CROSS-REFERENCE TO RELATED APPLICATION

The present application is entitled to priority under 35 U.S.C. §119(e) to U.S. Provisional Applications No. 61/428,894, filed Dec. 31, 2010, and No. 61/450,804, filed Mar. 9, 2011, which applications are incorporated by reference herein in their entireties.

BACKGROUND OF THE INVENTION

Arginase is an enzyme that catalyzes divalent cation-dependent hydrolysis of L-arginine to form L-ornithine and urea. Arginase is known to serve at least three important functions: (1) production of urea, (2) production of L-ornithine, and (3) regulation of arginine levels as a substrate for nitric oxide synthases (also known as NOSs, these enzymes convert L-arginine into citrulline and NO).

In most mammals, two isozymes of arginase exist: arginase I and arginase II. Arginase I is located primarily in the cytoplasm of the liver, while arginase II is found in the mitochondria of several tissues, with higher concentrations in the kidney and prostate, and lesser concentrations found in macrophages, lactating mammary glands, and the brain. The production of urea by hepatic arginase is an important mechanism to excrete nitrogen (ammonia) in the form of a highly soluble, non-toxic compound.

In tissues lacking a complete complement of the urea cycle enzymes, arginase regulates cellular concentrations of L-ornithine. L-ornithine is a precursor for the biosynthesis of polyamines (such as spermine, and spermidine, which have important roles in cell proliferation and differentiation) and praline (an important component of collagen, a component of fibrin and fibrotic tissue). Arginase also modulates NOS-mediated production of NO by regulating the levels of arginine present within tissues. In pathological disease states where extrahepatic arginases are elevated, L-arginine is more actively consumed, limiting its availability as a substrate for NOS. Arginase and NOS thus appear to be reciprocally regulated. In such disease states, it may be particularly desirable to inhibit the extrahepatic arginase.

An excess of arginase has been associated with a number of human pathological conditions, including erectile dysfunction, atherosclerosis, asthma, and pulmonary arterial hypertension and certain cancers, such as non-small-cell lung, prostate, and pancreatic cancers. Furthermore, high levels of arginase have been documented in animal models of human diseases such as myocardial ischemia-reperfusion injury, systolic (essential) hypertension, atherosclerosis, pulmonary arterial hypertension, erectile dysfunction, asthma, and multiple sclerosis.

Patients with conditions associated with an increase in arginase activity may stand to benefit from treatment with arginase inhibitors, such as $N^\omega$-hydroxy-L-arginine (L-HO-Arg), an intermediate in the NO synthase reaction. However, L-OH-Arg is a non-selective inhibitor, and thus the exact role of arginase in pathophysiology and the potential therapeutic effects of arginase inhibitors remain unknown.

While it is desirable not to extensively inhibit hepatic arginase, there is support for the hypothesis that the urea cycle is very robust. For example, Gau and coworkers (Mol. Ther., 2009, 1:1-9) has reported that rescue of an arginase I knockout animal by arginase I gene therapy only requires approximately 20% arginase activity in order to maintain normal ammonia levels. In other words, as long as the arginase activity in the liver does not fall below 20% normal levels, the urea cycle can function normally and hyperammonemia does not occur. In addition, the heterozygous arginase I knock-out mouse, which has only approximately 60% of normal hepatic arginase activity, has normal plasma ammonia levels as reported by Iyer and coworkers (Mol. Cell. Biol., 2002, 22:4491-4498).

There is a need in the art for inhibitors of arginase activity that may be used to treat a disease or disorder in a mammal, wherein the disease or disorder is characterized either by abnormally high arginase activity or by abnormally low nitric oxide levels in a tissue of the mammal. The present invention meets these needs.

BRIEF SUMMARY OF THE INVENTION

The invention includes a composition comprising an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propyl hexanoic acid, or 2-amino-6-borono-2-(3-(4-(3-methoxyphenylcarbamoyl)piperazin-1-yl)propyl)hexanoic acid.

In one embodiment, the first substituent comprises a boronic acid. In another embodiment, the first substituent is $-(CH_2)_4B(OH)_2$ or an ester thereof. In yet another embodiment, the proximal nitrogen is part of a primary, secondary or tertiary amine group. In yet another embodiment, the proximal nitrogen is part of a heterocyclic group. In yet another embodiment, the heterocyclic group is selected from the group consisting of azitidine, azetidine, pyrrolidine, piperidine, azepane, azocane, diazetidine imidazolidine, pyrazolidine, oxazolidine, isoxazolidine, thiazolidine, isothiazolidine, piperazine, morpholine, bridged analogs thereof, fused combinations thereof, and substituted versions thereof. In yet another embodiment, the second substituent is separated the alpha-carbon by a chain of two or three carbons. In yet another embodiment, the second substituent is separated from the alpha-carbon by a chain of three carbons. In yet another embodiment, the substituted heterocyclic group comprises at least one substituent selected from the group consisting of $(C_1-C_6)$alkyl, halo, aryl and heteroaryl, aryl$(C_1-C_6)$alkyl, heteroaryl$(C_1-C_6)$alkyl, $-C(=O)R^3$, $-SO_2R^3$, $-CONHR^3$, $COOR^3$, $OR^2$ and $NR^3R^3$, with the proviso that, if the at least one substituent is $OR^2$ or $NR^3R^3$, then the at least one substituent is not attached to the same carbon atom as the nitrogen atom of the heterocyclic group; wherein: $R^2$ is H, $(C_1-C_6)$alkyl, aryl, heteroaryl, aryl$(C_1-C_6)$alkyl, heteroaryl$(C_1-C_6)$alkyl, $-C(=O)(C_1-C_6)$alkyl, $-C(=O)($aryl$)$, $-C(=O)($heteroaryl$)$, $-SO_2(C_1-C_6)$alkyl, $-SO_2($aryl$)$, $-SO_2($heteroaryl$)$, $-CONH(C_1-C_6)$alkyl, $-CONH($aryl$)$, or $-CONH($heteroaryl$)$; and, each occurrence of $R^3$ is independently H, $(C_1-C_6)$alkyl, aryl, heteroaryl, aryl$(C_1-C_6)$alkyl, or heteroaryl$(C_1-C_6)$alkyl.

In one embodiment, the compound is a compound of formula (IV), or a derivative thereof, or a salt thereof:

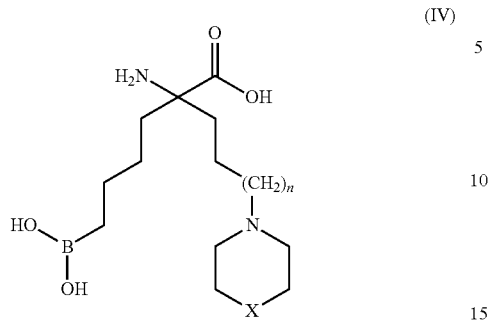
(IV)

wherein: n is 0, 1 or 2; X is $NR^5$, $CR^6R^7$, O, S, S(=O) or $S(O)_2$; $R^7$ is H, OH, $OR^8$, CN or $NR^8R^9$; and, $R^5$, $R^6$, $R^8$ and $R^9$ are independently H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —$SO_2(C_1-C_6)$alkyl, —$SO_2$(aryl), —$SO_2$(heteroaryl), —CONH$(C_1-C_6)$alkyl, —CONH(aryl), or —CONH(heteroaryl); or a derivative thereof, or a salt thereof.

In one embodiment, the compound is selected from the group consisting of:

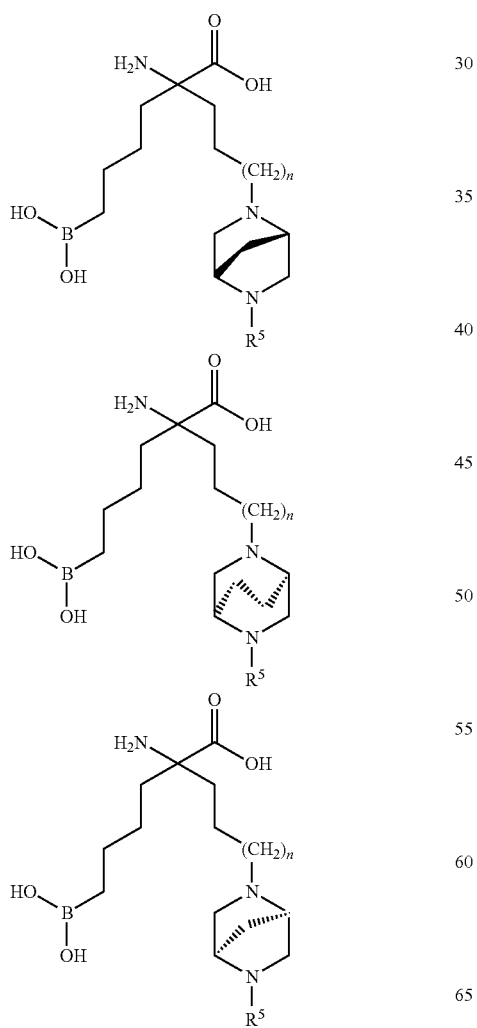

wherein: n is 0, 1 or 2; and, $R^5$ is H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —$SO_2(C_1-C_6)$alkyl, —$SO_2$(aryl), —$SO_2$(heteroaryl), —CONH$(C_1-C_6)$alkyl, —CONH(aryl), or —CONH(heteroaryl); or a derivative thereof, or a salt thereof.

In one embodiment, the compound is selected from the group consisting of:

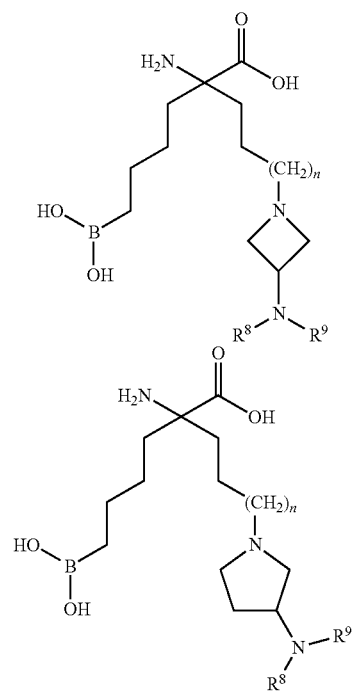

-continued

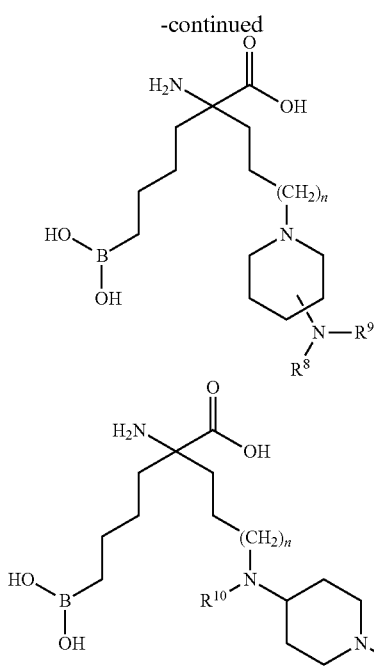

wherein: n is 0, 1 or 2; $R^8$ and $R^9$ are independently H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO$_2$$(C_1-C_6)$alkyl, —SO$_2$(aryl), —SO$_2$(heteroaryl), —CONH$(C_1-C_6)$alkyl, —CONH(aryl), or —CONH(heteroaryl); and $R^{10}$ is H, $(C_1-C_6)$ alkyl or arylalkyl; or a derivative thereof, or a salt thereof.

In one embodiment, the compound is a compound of formula (V), or a derivative thereof, or a salt thereof:

(V)

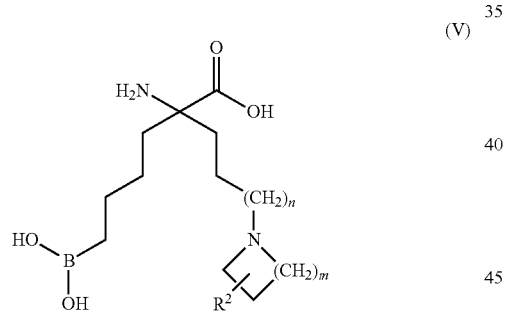

wherein: m is 1, 2, 3 or 4; n is 0, 1 or 2; and, $R^2$ is H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO$_2$$(C_1-C_6)$alkyl, —SO$_2$(aryl), —SO$_2$(heteroaryl), —CONH$(C_1-C_6)$alkyl, —CONH(aryl), or —CONH(heteroaryl).

In one embodiment, the compound is a compound of formula (VI) or a derivative thereof, or a salt thereof:

(VI)

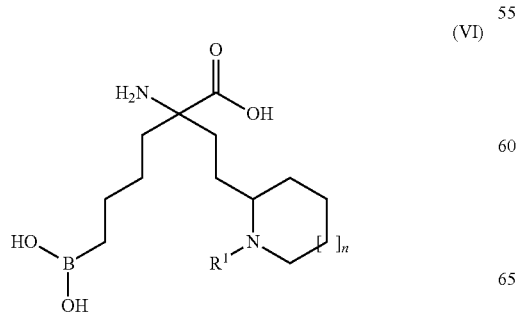

wherein: n is 0, 1 or 2; and $R^1$ is H, alkyl or arylalkyl; and, $R^2$ is H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO$_2$$(C_1-C_6)$alkyl, —SO$_2$(aryl), —SO$_2$(heteroaryl), —CONH$(C_1-C_6)$alkyl, —CONH(aryl), or —CONH(heteroaryl).

In one embodiment, the compound is selected from the group consisting of:

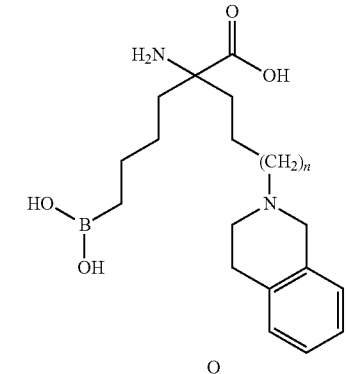

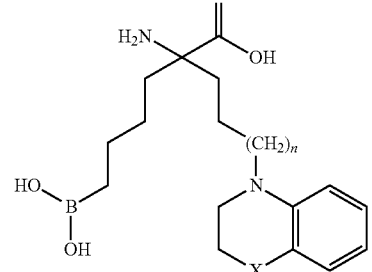

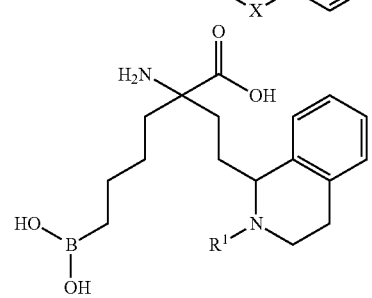

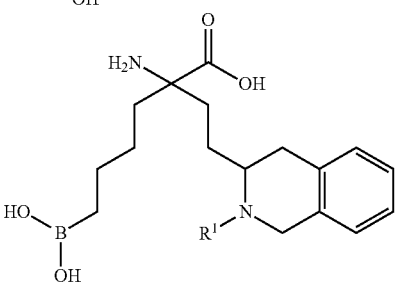

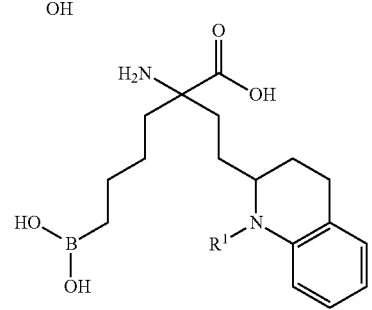

wherein: n is 0, 1 or 2; $R^1$ is H, alkyl or arylalkyl; X is $NR^5$, $CR^6R^7$, O, S, S(O), or S(O)$_2$; wherein, if X is $CR^6R^7$, then $R^7$ is H, OH, $OR^8$, CN or $NR^8R^9$; and, $R^5$, $R^6$, $R^8$ and $R^9$ are independently H, (C$_1$-C$_6$)alkyl, aryl, heteroaryl, aryl(C$_1$-C$_6$)alkyl, heteroaryl(C$_1$-C$_6$)alkyl, —C(=O)(C$_1$-C$_6$)alkyl, —C(=O)(aryl), —C(=O)(heteroaryl), —SO$_2$(C$_1$-C$_6$)alkyl, —SO$_2$(aryl), —SO$_2$(heteroaryl), —CONH(C$_1$-C$_6$)alkyl, —CONH(aryl), or —CONH(heteroaryl); or a derivative thereof, or a salt thereof:

In one embodiment, the compound is selected from the group consisting of:

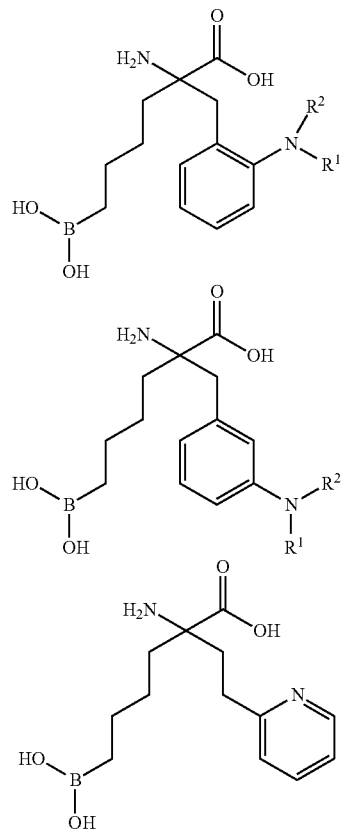

wherein $R^1$ and $R^2$ are independently H, C$_1$-C$_6$ alkyl or arylalkyl; or a derivative thereof, or a salt thereof:

In one embodiment, the compound is a compound of formula (VII), or a derivative thereof, or a salt thereof:

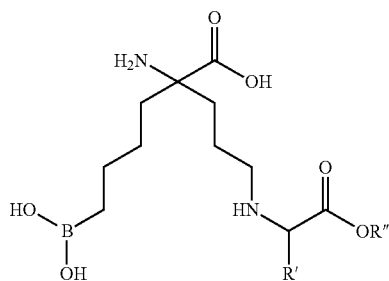

(VII)

wherein: R' is H, C$_1$-C$_6$ alkyl, benzyl, substituted benzyl, CH$_3$SCH$_2$CH$_2$—, CH$_3$S(=O)CH$_2$CH$_2$—, CH$_3$S(O)$_2$CH$_2$—, 3-indol-1H-yl-methyl, HSCH$_2$—, —CH$_2$CH$_2$C(=O)NH$_2$, —CH$_2$C(=O)NH$_2$, CH$_2$CH$_2$C(=O)OH, —CH$_2$C(=O)OH, —CH(OH)CH$_3$, —CH$_2$OH, —(CH$_2$)$_4$NH$_2$, —(CH$_2$)$_3$NHC(=NH)NH$_2$, or imidazole-4-yl-methyl; R" is H or C$_1$-C$_6$ alkyl.

In one embodiment, the compound is a compound of formula (VIII), or a derivative thereof, or a salt thereof:

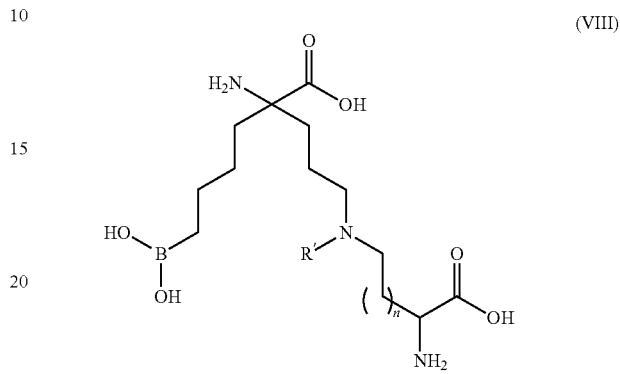

(VIII)

wherein: n is 0, 1, 2 or 3; and R' is H or C$_1$-C$_6$ alkyl.

In one embodiment, the compound is selected from the group consisting of:

2-amino-6-borono-2-(2-(piperazin-1-yl)ethyl)hexanoic acid;
2-amino-2-(3-(4-benzylpiperazin-1-yl)propyl)-6-boronohexanoic acid;
2-amino-6-borono-2-(3-(4-(2-chlorobenzyl)piperazin-1-yl)propyl)hexanoic acid;
2-amino-6-borono-2-(3-(4-(2-cyanobenzyl)piperazin-1-yl)propyl)hexanoic acid;
2-amino-6-borono-2-(3-(4-(2,4-difluorobenzyl)piperazin-1-yl)propyl)hexanoic acid;
2-amino-6-borono-2-(3-(4-(2,3-difluorobenzyl)piperazin-1-yl)propyl)hexanoic acid;
2-amino-6-borono-2-(3-(4-(3,4-dichlorobenzyl)piperazin-1-yl)propyl)hexanoic acid;
2-amino-6-borono-2-(3-(4-(3-(trifluoromethyl)benzyl)piperazin-1-yl)propyl)hexanoic acid;
2-amino-6-borono-2-(3-(4-(4-(methylsulfonyl)benzyl)piperazin-1-yl)propyl)hexanoic acid;
2-amino-6-borono-2-(3-(4-(4-fluorobenzyl)piperazin-1-yl)propyl)hexanoic acid;
2-amino-6-borono-2-(3-(4-(3,4-difluorobenzyl)piperazin-1-yl)propyl)hexanoic acid;
2-amino-6-borono-2-(3-(4-(3,5-difluorobenzyl)piperazin-1-yl)propyl)hexanoic acid;
2-amino-6-borono-2-(3-(4-phenethylpiperazin-1-yl)propyl)hexanoic acid;
2-amino-6-borono-2-(2-(4-(3,4-dichlorobenzyl)piperazin-1-yl)ethyl)hexanoic acid;
2-amino-6-borono-2-(3-(4-(3,4-dichlorophenyl)piperazin-1-yl)propyl)hexanoic acid;
2-amino-6-borono-2-(3-(2-(4-fluorophenyl)piperidin-1-yl)propyl)hexanoic acid;
2-amino-6-borono-2-(2-(piperidin-2-yl)ethyl)hexanoic acid;
2-amino-6-borono-2-(2-(1-(3,4-dichlorobenzyl)piperidin-2-yl)ethyl)hexanoic acid;
2-amino-6-borono-2-(2-(1-(3,5-difluorobenzyl)piperidin-2-yl)ethyl)hexanoic acid;
2-amino-6-borono-2-(2-(1-(3,4-difluorobenzyl)piperidin-2-yl)ethyl)hexanoic acid;

2-amino-6-borono-2-(2-(1-(3,4-dichlorobenzyl)piperidin-3-yl)ethyl)hexanoic acid;
2-amino-6-borono-2-(3-(1-(3,4-dichlorobenzyl)piperidin-2-yl)propyl)hexanoic acid;
2-amino-6-borono-2-(3-(1-(3,4-difluorobenzyl)piperidin-2-yl)propyl)hexanoic acid;
2-amino-6-borono-2-(3-(1-(3,5-difluorobenzyl)piperidin-2-yl)propyl)hexanoic acid;
2-amino-6-borono-2-(3-(3-phenylpiperidin-1-yl)propyl) hexanoic acid;
2-amino-6-borono-2-(3-(3-(5-fluoro-1H-benzo[d]imidazol-2-yl)piperidin-1-yl)propyl)hexanoic acid;
2-amino-6-borono-2-(3-(4-(3,4-difluorobenzyl)piperidin-1-yl)propyl)hexanoic acid;
2-amino-6-borono-2-(3-(4-(pyrimidin-2-ylmethyl)piperidin-1-yl)propyl)hexanoic acid;
2-(3-(3H-spiro[isobenzofuran-1,4'piperidine]-1'-yl)propyl)-2-amino-6-boronohexanoic acid;
2-amino-6-borono-2(3-(4-oxo-1-phenyl-1,3,8-triazaspiro[4.5]decan-8-yl)propyl) hexanoic acid;
2-amino-6-borono-2-(3-(4-(2-chlorophenyl)-1H-pyrazol-1-yl)piperidin-1-yl) propylhexanoic acid;
2-amino-6-borono-2-(3-(4-(5-phenyl-1,3,4-oxadiazol-2-yl)piperidin-1-yl)propyl) hexanoic acid;
2-amino-6-borono-2-(3-(4-(4-(trifluoromethyl)phenoxy)piperidin-1-yl)propyl) hexanoic acid;
2-amino-6-borono-2-(3-(4-(2-isopropylphenoxy)piperidin-1-yl)propyl)hexanoic acid;
2-amino-6-borono-2-(3-(4-(4-fluorophenyl)piperidin-1-yl) propylhexanoic acid;
2-amino-6-borono-2-(3-(4-(4-methoxyphenyl)piperidin-1-yl)propyl)hexanoic acid;
2-amino-6-borono-2-(3-(4-(4-chlorophenyl)-5,6-dihydropyridin-1(2H)-yl)propyl) hexanoic acid;
2-amino-2-(3-(4-benzyl-4-hydroxypiperidin-1-yl)propyl)-6-boronohexanoic acid;
2-amino-6-borono-2-(3-(4-(4-chlorophenyl)-4-hydroxypiperidin-1-yl)propyl)hexanoic acid;
2-amino-6-borono-2-(3-(4-(5-(trifluoromethyl)pyridin-2-yl) piperazin-1-yl)propyl) hexanoic acid;
2-amino-6-borono-2-(3-(4-hydroxypiperidin-1-yl)propyl) hexanoic acid;
2-amino-2-(3-(4-((S)-2-amino-3-methylbutanoyloxy)piperidin-1-yl)propyl)-6-boronohexanoic acid;
2-amino-2-(3-(4-benzamidopiperidin-1-yl)propyl)-6-boronohexanoic acid;
2-amino-6-borono-2-(3-(3,4-dihydroisoquinolin-2(1H)-yl)propyl)hexanoic acid;
2-amino-6-borono-2-(3-(4-methyl-2-phenylpiperazin-1-yl)propyl)hexanoic acid;
2-amino-2-(3-(2-benzylpiperidin-1-yl)propyl)-6-boronohexanoic acid;
2-amino-6-borono-2-(3-(2-(4-methoxyphenyl)piperidin-1-yl)propyl)hexanoic acid;
2-amino-6-borono-2-(3-(2-(3-methoxyphenyl)pyrrolidin-1-yl)propyl)hexanoic acid
2-amino-6-borono-2-(3-(2-(2-fluorobenzyl)pyrrolidin-1-yl)propyl)hexanoic acid;
2-amino-6-borono-2-(3-(2-(2-(trifluoromethyl)phenyl)pyrrolidin-1-yl)propyl) hexanoic acid;
2-amino-6-borono-2-(3-(2-(4-fluorophenyl)pyrrolidin-1-yl)propyl)hexanoic acid;
2-amino-6-borono-2-(3-(2-(3-chlorophenyl)pyrrolidin-1-yl)propyl)hexanoic acid;
2-amino-2-(3-(2-(biphenyl-4-yl)pyrrolidin-1-yl)propyl)-6-borono-hexanoic acid;
2-amino-6-borono-2-(3-(2-(3,4-dichlorophenyl)pyrrolidin-1-yl)propyl)hexanoic acid;
2-amino-6-borono-2-(3-(pyrrolidin-1-yl)propyl)hexanoic acid;
2-amino-2-(3-(azetidin-1-yl)propyl)-6-boronohexanoic acid;
2-amino-6-borono-2-(3-(3-phenylazetidin-1-yl)propyl)hexanoic acid;
2-amino-6-borono-2-(3-(3-p-tolylazetidin-1-yl)propyl)hexanoic acid;
2-amino-6-borono-2-(3-(3-(3-(3,4-dichlorophenyl)ureido) azetidin-1-yl)propyl) hexanoic acid;
2-amino-6-borono-2-(3-(3-(3-(4-fluorophenyl)ureido)azetidin-1-yl)propyl) hexanoic acid;
2-amino-6-borono-2-(3-(3-chloro-2-fluorobenzamido)azetidin-1-yl)propyl) hexanoic acid;
2-amino-6-borono-2-(3-(4-ethylpiperazin-1-yl)propyl)hexanoic acid;
2-amino-6-borono-2-(3-morpholinopropyl)hexanoic acid;
2-amino-6-borono-2-(3-thiomorpholinopropyl)hexanoic acid;
2-amino-6-borono-2-(3-(thiazolidin-2-yl)propyl)hexanoic acid;
2-amino-6-borono-2-(3-(phenethylamino)propyl)hexanoic acid;
2-amino-6-borono-2-(3-(methyl(phenethyl)aminopropyl) hexanoic acid;
2-amino-6-borono-2-(3-(ethyl(naphthalen-1-ylmethyl) amino)propyl)hexanoic acid;
2-amino-6-borono-2-(3-(methyl(naphthalen-1-ylmethyl) amino)propyl)hexanoic acid;
2-amino-6-borono-2-(3-((cyclohexylmethyl)(ethyl)amino) propyl)hexanoic acid;
2-amino-2-(3-(benzyl(ethyl)amino)propyl-6-boronohexanoic acid;
2-amino-2-(3-(benzyl(ethyl)amino)propyl)-6-boronohexanoic acid;
2-amino-6-borono-2-(3-((4-chlorobenzyl)(methyl)amino) propyl)hexanoic acid;
2-amino-6-borono-2-(3-((3,4-dichlorobenzyl)(methyl) amino)propyl)hexanoic acid;
2-amino-6-borono-2-(3-((3,4-dichlorobenzyl)(ethyl)amino) propyl)hexanoic acid;
2-amino-6-borono-2-(3-(cyclohexylamino)propyl)hexanoic acid;
2-amino-6-borono-2-(3-(cyclohexyl(methyl)amino)propyl) hexanoic acid;
2-amino-6-borono-2-(3-(methyl(tetrahydro-2H-pyran-4-yl) amino)propyl) hexanoic acid;
2-amino-6-borono-2-(3-(cyclopentyl(methyl)amino)propyl) hexanoic acid;
2-amino-6-borono-2-(3-((3-chlorobenzyl)(methyl)amino) propyl)hexanoic acid;
2-amino-6-borono-2-(3-(ethyl(tetrahydro-2H-pyran-4-yl) amino)propyl)hexanoic acid;
2-amino-6-borono-2-(3-((6-fluorochroman-4-yl)(methyl) amino)propyl)hexanoic acid;
2-amino-6-borono-2-(3-(2-methoxyethylamino)propyl)hexanoic acid;
2-amino-6-borono-2-(3-((2-methoxyethyl)(methyl)amino) propyl)hexanoic acid;
2-amino-6-borono-2-(3-((S)-1-methoxypropan-2-ylamino) propyl)hexanoic acid;
2-amino-6-borono-2-(3-(dimethylamino)propyl)hexanoic acid;
2-amino-6-borono-2-(3-((2-(dimethylamino)ethyl(methyl) amino)propyl)hexanoic acid;

2-amino-6-borono-2-(3-(2-(dimethylamino)ethylamino) propyl)hexanoic acid;
2-amino-6-borono-2-(3-(diethylamino)propyl)hexanoic acid;
2-amino-6-borono-2-(3-((1R,4R)-5-(3,4-dichlorophenylcarbamoyl)-2,5-diazabicyclo[2.2.2]heptan-2-yl)propyl)hexanoic acid;
2-amino-6-borono-2-(3-(4-((S)-3-methyl-2((R)-4-((3R,5S,7R,8R,9S,10S,12S,13R,14S,17R)-3,7,12-trihydroxy-10,13-dimethylhexadecahydro-1H-cyclopenta[α]phenathren-17-yl)pentanamido)butanoyloxy)piperidin-1-yl) propyl)hexanoic acid;
2-amino-6-borono-2-(4-(piperazin-1-yl)butyl)hexanoic acid;
2-amino-6-borono-2-(4-(4-(3,4-dichlorophenyl)piperazin-1-yl)butyl)hexanoic acid;
2-amino-6-borono-2-(4-(4-(3,4-difluorobenzyl)piperidin-1-yl)butyl)hexanoic acid;
2-amino-6-borono-2-(4-(3,4-dihydroisoquinolin-2(1H)-yl) butyl)hexanoic acid;
2-amino-6-borono-2-(4-(2-(4-fluorophenyl)piperidin-1-yl) butyl)hexanoic acid;
2-amino-6-borono-2-(3-(carboxymethylamino)propyl)hexanoic acid;
2-amino-2-(3-(4-(biphenyl-4-ylmethyl)piperazin-1-yl)propyl)-6-boronohexanoic acid;
2-amino-2-(3-(4-benzhydrylpiperazin-1-yl)propyl)-6-boronohexanoic acid;
2-amino-6-borono-2-(3-(4-(4-fluorobenzoyl)piperidin-1-yl) propyl)hexanoic acid;
2-(3-(3-(1H-benzo[d]imidazol-1-yl)-8-azabicyclo[3.2.1]octan-8-yl)propyl)-2-amino-6-boronohexanoic acid;
2-amino-6-borono-2(3-(4-(phenylamino)piperidin-1-yl)propyl)hexanoic acid;
2-amino-6-borono-2-(3-(4-(3,4-dichlorobenzylamino)piperidin-1-yl)propyl) hexanoic acid;
2-amino-6-borono-2-(3-(4-((3,4-dichlorobenzyl)(ethyl) amino)piperidin-1-yl) propyl)hexanoic acid;
2-amino-6-boron-2-(3-(4-methylpiperazin-1-yl)propyl)hexanoic acid;
2-amino-6-borono-2-(3-(3-fluoro-4-phenylpiperidin-1-yl) propyl)hexanoic acid;
2-amino-6-borono-2-(3-(4-(N-(3,4-dichlorobenzyl)octanamido)piperidin-1-yl) propyl)hexanoic acid;
2-amino-3-(3-(4-benzyl-4-(decanoyloxy)piperidin-1-yl)propyl)-6-boronohexanoic acid;
2-amino-2-(3-(3-(benzo[d]oxazol-2-yl)piperidin-1-yl)propyl)-6-boronohexanoic acid;
2-amino-6-borono-2-(3-(2-phenylpyrrolin-1-yl)propyl)hexanoic acid;
2-amino-6-borono-2-(3-(3-(3-(3,4-dichlorophenyl)ureido) pyrrolidin-1-yl)propyl) hexanoic acid;
2-amino-6-borono-2-(3-(3-(3-(4-fluorophenyl)ureido)pyrrolidin-1-yl)propyl) hexanoic acid;
2-amino-6-borono-2-(3-(3-(3,4-dichlorophenylsulfonamido)pyrrolidin-1-yl) propyl)hexanoic acid;
2-(3-(1H-imidazol-1-yl)propyl)-2-amino-6-boronohexanoic acid;
2-(3-(1H-benzo[d]imidazol-1-yl)propyl)-2-amino-6-boronohexanoic acid;
2-amino-6-borono-2-(3-(cyclopentylamino)propyl)hexanoic acid;
2-amino-6-borono-2-(3-(tetrahydro-2H-pyran-4-ylamino) propyl)hexanoic acid;
2-amino-6-borono-2-(3-((3R)-3-methoxytetrahydro-2H-pyran-4-ylamino)propyl) hexanoic acid;
2-amino-6-borono-2-(3-(methyl(naphthalen-2-ylmethyl) amino)propyl)hexanoic acid;
2-amino-6-borono-2-(3-(methyl((4-methylnaphthalen-1-yl) methyl)amino)propyl) hexanoic acid;
2-amino-6-borono-2-(3-((4(3,4-dichlorophenoxy)benzyl) (methyl)amino)propyl) hexanoic acid;
2-amino-6-borono-2-(3-((3',4'-dichlorobiphenyl-4-yl)methyl)(methyl)amino) propyl)hexanoic acid;
2-amino-6-borono-2-(3-((3',4'-dichlorobiphenyl)-4-yl)methylamino)propyl) hexanoic acid;
(S)-2-amino-6-borono-2-(3-(1-carboxyethylamino)propyl) hexanoic acid;
(S)-2-amino-6-borono-2-(3-(1-carboxy-3-methylbutylamino)propyl)hexanoic acid;
2-amino-6-borono-2-(3-((S)-1-methoxy-1-oxopropan-2-ylamino)propyl)hexanoic acid;
(S)-2-amino-6-borono-2-(3-(1-methoxy-4-methyl-1-oxopentan-2-ylamino)propyl) hexanoic acid;
2-amino-6-borono-2-(3-(4-(3,4-dichlorobenzoyl)piperazin-1-yl)propyl)hexanoic acid;
2-amino-6-borono-2-(3-(4-(4-methoxybenzoyl)piperazin-1-yl)propyl)hexanoic acid;
2-amino-6-borono-2-(3-(4-(3-methoxybenzoyl)piperazin-1-yl)propyl)hexanoic acid;
2-amino-6-borono-2-(3-(4-(4-methylbenzoyl)piperazin-1-yl)propyl)hexanoic acid;
2-amino-6-borono-2-(3-(4-(4-fluorobenzoyl)piperazin-1yl) propyl)hexanoic acid;
2-amino-6-borono-2-(3-(4-(2-fluorobenzoyl)piperazin-1-yl) propyl)hexanoic acid;
2-amino-6-borono-2-(3-(4-(2-chlorobenzoyl)piperazin-1-yl)propyl)hexanoic acid;
2-amino-6-borono-2-(3-(4-(3-fluorobenzoyl)piperazin-1-yl) propyl)hexanoic acid;
2-amino-6-borono-2-(3-(4-(4-(trifluoromethyl)benzoyl)piperazin-1-yl) propyl)hexanoic acid;
2-amino-6-borono-2-(3-(4-(4-carbamoylbenzoyl)piperazin-1-yl)propyl)hexanoic acid;
2-amino-6-borono-2-(3-(4-(3,4-dichlorophenylcarbamoyl) piperazin-1-yl)propyl) hexanoic acid;
2-amino-6-borono-2-(3-(4-(2-fluorophenylcarbamoyl)piperazin-1-yl)propyl) hexanoic acid;
2-amino-6-borono-2-(3-(4-(3-fluorophenylcarbamoyl)piperazin-1-yl)propyl) hexanoic acid;
2-amino-6-borono-2-(3-(4-(4-fluorophenylcarbamoyl)piperazin-1-yl)propyl)hexanoic acid;
2-amino-6-borono-2-(3-(4-(3,4-difluorophenylcarbamoyl) piperazin-1-yl)propyl hexanoic acid;
2-amino-6-borono-2-(3-(4-(2,5-difluorophenylcarbamoyl) piperazin-1-yl)propyl)hexanoic acid;
2-amino-6-borono-2-(3-(4-(2,4-difluorophenylcarbamoyl) piperazin-1-yl)propyl)hexanoic acid;
2-amino-6-borono-2-(3-(4-(2,3-difluorophenylcarbamoyl) piperazin-1-yl)propyl)hexanoic acid;
2-amino-6-borono-2-(3-(4-(3,5-difluorophenylcarbamoyl) piperazin-1-yl)propyl)hexanoic acid;
2-amino-6-borono-2-(3-(4-tosylpiperazin-1-yl)propyl)hexanoic acid;
2-amino-6-borono-2-(3-(4-(4-fluorophenylsulfonyl)piperazin-1-yl)propyl) hexanoic acid;
2-amino-6-borono-2-(3-(4-(3-fluorophenylsulfonyl)piperazin-1-yl)propyl) hexanoic acid;
2-amino-6-borono-2-(3-(4-(3,4-dichlorophenylsulfonyl)piperazin-1-yl)propyl) hexanoic acid;
a salt thereof, a derivative thereof and a mixture thereof.

In one embodiment, the derivative is an ester prodrug of formula:

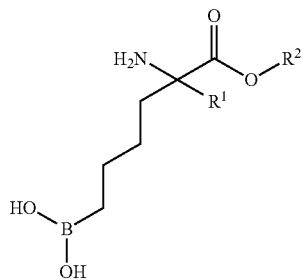

wherein:
R¹ is the second substituent;
R² is selected from the group consisting of $C_1$-$C_6$ alkyl, $C_3$-$C_7$ cycloalkyl, tetrahydrofuran-2-yl-methyl, tetrahydrofuran-3-yl-methyl, $C_3$-$C_7$ cycloalkyl-methyl, 2-($C_3$-$C_7$ cycloalkyl)-ethyl, dihydrofuran-2(3H)-one-4-yl-methyl, 2-hydroxyl-ethyl, 2-hydroxyl-2-methyl-ethyl, phenyl, 2-tolyl, 3-tolyl, 4-tolyl, 2-methoxy-phenyl, 3-methoxy-phenyl, 4-methoxy-phenyl, 2,3-dihydro-1H-inden-4-yl, 2,3-dihydro-1H-inden-5-yl, thiazol-2-yl-methyl, thiazol-4-yl-methyl, imidazole-2-yl-$(CH_2)_n$—, imidazole-4-yl-$(CH_2)_n$—, 2-methyl-1H-benzo[d]imidazole-2-yl-$(CH_2)_n$—, $R^5C(=O)OCH_2CH_2$—, $R^5C(=O)OCH(CH_3)CH_2$—, $R^5C(=O)OCH_2$—, or $R^5C(=O)OCH(CH_3)$—;
n is 1, 2, 3 or 4;
R⁵ is H, $C_1$-$C_6$ alkyl, $C_3$-$C_7$ cycloalkyl, aryl, heteroaryl, or $CH(R^6)NH_2$; and
R⁶ is H, $C_1$-$C_6$ alkyl, benzyl, substituted benzyl, $CH_3SCH_2CH_2$—, $CH_3S(=O)CH_2CH_2$—, $CH_3S(O)_2CH_2CH_2$—, 3-indol-1H-yl-methyl, $HSCH_2$—, —$CH_2CH_2C(=O)NH_2$, —$CH_2C(=O)NH_2$, $CH_2CH_2C(=O)OH$, $CH_2C(=O)OH$, —$CH(OH)CH_3$, —$CH_2OH$, —$(CH_2)_4NH_2$, —$(CH_2)_3NHC(=NH)NH_2$, or imidazole-4-yl-methyl; wherein the benzoimidazole is optionally substituted with at least one substituent selected from the group consisting of ($C_1$-$C_6$)alkyl, halo and ($C_1$-$C_6$)alkoxy.

In one embodiment, the derivative is selected from the group consisting of:
5-amino-8-(4-(3,4-dichlorobenzyl)piperazin-1-yl)-5-(isopropoxycarbonyl) octylboronic acid;
5-amino-8-(4-(3,4-dichlorobenzyl)piperazin-1-yl)-5-(isopentyloxycarbonyl) octylboronic acid;
5-amino-8-(4-(3,4-dichlorobenzyl)piperazin-1-yl)-5-((2-(piperidin-1-yl)ethoxy) carbonyl)octylboronic acid;
5-amino-8-(4-(3,4-dichlorobenzyl)piperazin-1-yl)-5-((2-morpholinoethoxy) carbonyl)octylboronic acid;
5-amino-5-(methoxycarbonyl)-8-(4-(4-methylsulfonyl)benzyl)piperazin-1-yl)octylboronic acid;
5-amino-5-(ethoxycarbonyl)-8-(4-(4-(methylsulfonyl)benzyl)piperazin-1-yl)octylboronic acid;
5-amino-8-(4-(4-(methylsulfonyl)benzyl)piperazine-1-yl)-5-(propoxycarbonyl) octylboronic acid;
5-amino-5-(isopropoxycarbonyl)-8-(4-(4-(methylsulfonyl)benzyl)piperazin-1-yl)octylboronic acid;
5-amino-5-(isobutoxycarbonyl)-8-(4-(4-(methylsulfonyl)benzyl)piperazin-1-yl)octylboronic acid;
5-amino-5-(isopentyloxycarbonyl)-8-(4-(4-(methylsulfonyl)benzyl)piperazin-1-yl)octylboronic acid;
5-amino-8-(4-(4-(methylsulfonyl)benzyl)piperazin-1-yl)-5-((pentan-3-yloxy)carbonyl)octylboronic acid;
5-amino-5-((3-methylbutan-2-yloxy)carbonyl)-8-(4-(4-(methylsulfonyl) benzylpiperazin-1-yl)octylboronic acid;
5-amino-5-((2-methoxyethoxy)carbonyl)-8-(4-(4-(methylsulfonyl)benzyl) piperazin-1-yl)octylboronic acid;
5-amino-5-((2-hydroxyethoxy)carbonyl)-8-(4-(4-(methylsulfonyl)benzyl) piperazin-1-yl)octylboronic acid;
5-amino-8-(4-(4-(methylsulfonyl)benzyl)piperazine-1-yl-5-((2-morpholinoethoxy)carbonyl)octylboronic acid;
5-amino-8-(4-(3,4-dichlorophenyl)piperazin-1-yl-5-(methoxycarbonyl) octylboronic acid;
a salt thereof and a mixture thereof.

In one embodiment, the composition further comprises at least one pharmaceutically acceptable carrier.

In one embodiment, the composition further comprises an inhibitor selected from the group consisting of a phosphodiesterase-1 (PDE1) inhibitor, a phosphodiesterase-2 (PDE2) inhibitor, a phosphodiesterase-3 (PDE3) inhibitor, a phosphodiesterase-4 (PDE4) inhibitor, a phosphodiesterase-5 (PDE5) inhibitor, a non-specific PDE inhibitor that inhibits at least two enzymes selected from the group consisting of PDE1, PDE2, PDE3, PDE4, and PDE5, and a combination thereof.

In one embodiment, the composition further comprises at least one pharmaceutically acceptable carrier and an inhibitor selected from the group consisting of a phosphodiesterase-1 (PDE1) inhibitor, a phosphodiesterase-2 (PDE2) inhibitor, a phosphodiesterase-3 (PDE3) inhibitor, a phosphodiesterase-4 (PDE4) inhibitor, a phosphodiesterase-5 (PDE5) inhibitor, a non-specific PDE inhibitor that inhibits at least two enzymes selected from the group consisting of PDE1, PDE2, PDE3, PDE4, and PDE5, and a combination thereof.

In one embodiment, the compound comprises an imageable moiety selected from the group consisting of a fluorescent label, gamma ray emitting radioisotope, positron emitting radioisotope, magnetic resonance imaging contrast agent, X-ray contrast agent, and ultrasound contrast agent.

The invention also includes a method of inhibiting arginase in a mammal. The method comprises administering to the mammal an effective amount of a formulation comprising an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propyl hexanoic acid, or 2-amino-6-borono-2-(3-(4-(3-methoxyphenylcarbamoyl)piperazin-1-yl)propyl)hexanoic acid.

In one embodiment, the arginase is yeast, bacterial, parasitic, or mammalian. In another embodiment, the mammalian arginase is a human type I arginase or a human type II arginase. In yet another embodiment, the formulation is administered to the mammal via at least one route selected from the group consisting of oral, nasal, pulmonary, transdermal, intranasal, ophthalmological, rectal, and parenteral, wherein the parenteral administration comprises subcutaneous, intravenous, intraurethral, or intramuscular.

The invention further includes a method of treating a disorder or disease in a mammal. The method comprises administering to the mammal a therapeutically effective amount of a formulation comprising at least one pharmaceutically acceptable carrier and an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl) propyl hexanoic acid, or 2-amino-6-boron-2-(3-(4-(3-methoxyphenylcarbamoyl)piperazin-1-yl)propyl)hexanoic acid.

In one embodiment, the disorder or disease is characterized by abnormally high arginase activity or abnormally low nitric oxide synthase activity in a tissue of the mammal.

In one embodiment, the disorder or disease is selected from the group consisting of a condition associated with ischemic reperfusion injury, idiopathic pulmonary fibrosis, pulmonary arterial hypertension, acute coronary vasodilation, asthma, acute respiratory distress syndrome, chronic obstructive pulmonary disease (COPD), bronchopulmonary dysplasia, hypoxic respiratory failure, cystic fibrosis, subarachnoid hemorrhage, thrombosis, microbial infection, cancer, wound healing, blood preservation, cardiac hypertrophy, gastrointestinal disease, pulmonary inflammatory disease, sexual arousal disorder, cardiovascular disorder, disease caused by a pathogenic microorganism, immunological disorder, cancer, pre-term labor, Reynaud's disease, psoriasis, rheumatoid arthritis, and Peyronie's Disease, wherein the condition associated with ischemia reperfusion injury comprises myocardial ischemia-reperfusion injury, organ transplantation, acute renal failure, or vaso-occlusive crises in sickle cell disease.

In one embodiment, the formulation is administered to the mammal via at least one route selected from the group consisting of oral, nasal, pulmonary, transdermal, intranasal, ophthalmological, rectal, and parenteral, wherein the parenteral administration comprises subcutaneous, intravenous, intraurethral, or intramuscular.

The invention also includes a method of diagnosing arginase overexpression in a mammal. The method comprising the steps of administering to the mammal a diagnostically-effective amount of a formulation comprising an alpha-amino acid compound, a derivative thereof or a pharmaceutically acceptable salt thereof; and, imaging the mammal. A first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl) propyl hexanoic acid, or 2-amino-6-borono-2-(3-(4-(3-methoxyphenylcarbamoyl)piperazin-1-yl)propyl)hexanoic acid. The compound comprises an imaging substituent that allows for in vivo imaging of the compound.

In one embodiment, the arginase overexpression is associated with asthma, cancer, bacterial infection, or combinations thereof. In another embodiment, the imaging substituent is selected from the group consisting of a fluorescent label, gamma ray emitting radioisotope, positron emitting radioisotope, magnetic resonance imaging contrast agent, X-ray contrast agent, and ultrasound contrast agent.

The invention further includes a method of relaxing smooth muscle or enhancing smooth muscle relaxation in a mammal. The method comprises administering to the mammal a therapeutically effective amount of a formulation comprising at least one pharmaceutically acceptable carrier and an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propyl hexanoic acid, or 2-amino-6-borono-2-(3-(4-(3-methoxyphenylcarbamoyl)piperazin-1-yl) propyl)hexanoic acid.

In one embodiment, the smooth muscle is selected from the group consisting of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, ocular smooth muscle, and a combination thereof. In another embodiment, the formulation is administered to the mammal via at least one route selected from the group consisting of oral, nasal, pulmonary, transdermal, intranasal, ophthalmological, rectal, and parenteral, wherein the parenteral administration comprises subcutaneous, intravenous, intraurethral, or intramuscular.

The invention also includes a method of providing relief from immune suppression in a mammal. The method comprises administering to the mammal a therapeutically effective amount of a formulation comprising at least one pharmaceutically acceptable carrier and an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propyl hexanoic acid, or 2-amino-6-borono-2-(3-(4-(3-methoxyphenylcarbamoyl)piperazin-1-yl) propyl)hexanoic acid.

In one embodiment, the mammal is suffering from a disease or condition selected from the group consisting of a chronic infectious disease, bacterial infection, parasitic infection, trauma, leprosy, tuberculosis, liver transplantation, cancer, and combinations thereof. In another embodiment, the formulation is administered to the mammal via at least one route selected from the group consisting of oral, nasal, pulmonary, transdermal, intranasal, ophthalmological, rectal, and parenteral, wherein the parenteral administration comprises subcutaneous, intravenous, intraurethral, or intramuscular.

The method further includes a method of inhibiting production of ornithine in a mammal. The method comprises administering to the mammal a therapeutically effective amount of a formulation comprising at least one pharmaceutically acceptable carrier and an alpha-amino acid compound, or a derivative thereof, or a salt thereof, wherein a first substituent and a second substituent are linked to the alpha-carbon of the compound. The first substituent comprises a moiety selected from the group consisting of a boronic acid and N-hydroxy guanidine. The second substituent comprises a proximal nitrogen atom, wherein the proximal nitrogen is basic, further wherein the proximal nitrogen is separated from the alpha-carbon by a chain of two, three or four carbons, with the proviso that the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl) propyl hexanoic acid, or 2-amino-6-borono-2-(3-(4-(3-methoxyphenylcarbamoyl)piperazin-1-yl)propyl)hexanoic acid.

In one embodiment, the mammal is suffering from a disease or condition selected from the group consisting cancer and fibrotic disease. In another embodiment, the formulation is administered to the mammal via at least one route selected from the group consisting of oral, nasal, pulmonary, transdermal, intranasal, ophthalmological, rectal, and parenteral, wherein the parenteral administration comprises subcutaneous, intravenous, intraurethral, or intramuscular.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
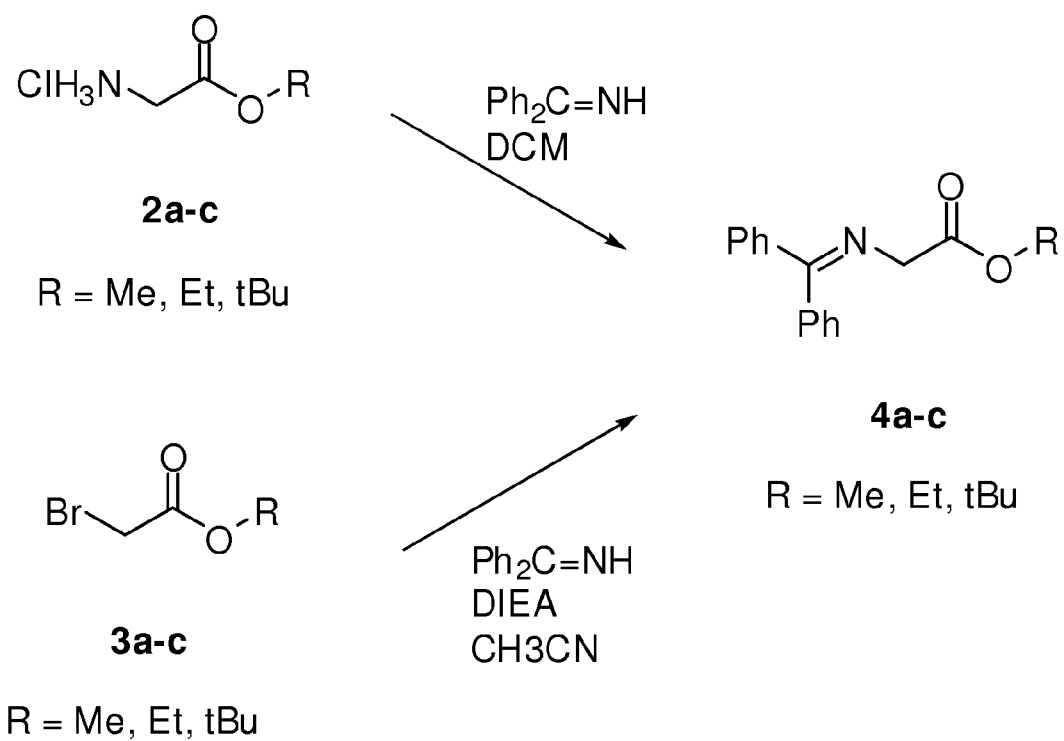
FIG. 1 is a scheme illustrating the solution-phase syntheses of selected starting materials.

The present invention includes enzyme inhibitors, compositions comprising such inhibitors, and uses thereof. In a non-limiting aspect, the invention includes arginase inhibitors, compositions comprising such arginase inhibitors, and methods of diagnosing and/or treating conditions characterized by abnormally high arginase activity or by abnormally low nitric oxide levels using the compositions of the invention.

Definitions

As employed above and throughout the disclosure, the following terms, unless otherwise indicated, shall be understood to have the following meanings.

The articles "a" and "an" are used herein to refer to one or to more than one (i.e., to at least one) of the grammatical object of the article. By way of example, "an element" means one element or more than one element.

As used herein, the term "about," when referring to a measurable value such as an amount, a temporal duration, and the like, is meant to encompass variations of ±20%, preferably ±10%, more preferably ±5%, even more preferably ±1%, and yet even more preferably ±0.1% from the specified value, as such variations are appropriate to perform the disclosed methods and compositions.

As used herein, the term "ABH" refers to 2(S)-amino-6-boronohexanoic acid. As used herein, the term "BEC" refers to S-(2-boronoethyl)-L-cysteine.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "treating" and "treatment" refer to the preventative, curative, and palliative treatment of a condition malady or affliction, especially in a mammalian patient in need of such treatment, preferably a human patient.

As used herein, "administering" refers to the act of giving or providing a composition or compound to a patient by the patient herself or by a caregiver, such as a medical professional or the like, including the act of ingestion by or application to the patient or the like wherein the composition or compound can exert its effects.

By the term "effective amount", as used herein, is meant an amount of an inhibitor that is sufficient to prevent, reduce or eliminate the symptoms or condition that is of concern. The skilled artisan would understand that the amount varies and can be readily determined based on a number of factors such as the disease or condition being treated, the age and health and physical condition of the animal being treated, the severity of the disease, the particular compound being administered, and the like. Generally, the dosage will be set between 0.01 mg/kg and 250 mg/kg. The invention is not limited to any particular method of administration.

As used herein, the term "pharmaceutically-acceptable" refers to those compounds, materials, compositions, or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, the term "pharmaceutically-acceptable salts" refers to derivatives of the disclosed compounds wherein the parent compound is modified by making acid or base salts thereof, including acid addition salts and base addition salts. Examples of pharmaceutically acceptable salts include, but are not limited to, mineral or organic acid salts of basic residues such as amines; alkali or organic salts of acidic residues such as carboxylic acids; and the like.

The term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, lycerophosphoric, heptanoic, hexanoic, hydrochloric, hydrobromic, hydroiodic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like.

The term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, arylalkyl halides like benzyl and phenethyl bromides, and others. The pharmaceutically-acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperizine, pyrrolidine, ethanolamine, morpholine, diazapine, ethylene diamine, pyridine, quinoline, quinuclidine, and the like.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Except insofar as any conventional media or agent is incompatible with the active compound, use thereof in the compositions is contemplated. Supplementary active compounds can also be incorporated into the compositions.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, the term "patient" refers to an animal, including a mammal, preferably a human.

An "amino acid" unless otherwise indicated is an alpha-amino acid containing an alpha carbon (also known as α-carbon, Cα, or αC), an amine group attached to the α-carbon, a carboxylic acid group attached to the α-carbon, and at least one side chain group attached to the α-carbon. This at least one side chain would encompass those found in the twenty natural amino acids, such as those in glycine, alanine, lysine, or glutamic acid, as well as those that are not found in the known amino acids (un-natural amino acid).

As used herein, the term "basic nitrogen" refers to a nitrogen atom that has a lone pair of electrons available to bind to a proton and form an ammonium ion. The basic nitrogen may be part of a primary, secondary, or tertiary amine. Additionally, the basic nitrogen may be part of a heteroaryl ring when the N atom's lone pair of electrons can bind to a proton. The basic nitrogen can form a hydrogen bond as an acceptor or form salt bridges with acidic groups on proteins such as the side chain of glutamic or aspartic acid.

"Instructional material," as that term is used herein, includes a publication, a recording, a diagram, or any other medium of expression which can be used to communicate the usefulness of the nucleic acid, peptide, and/or compound of the invention in the kit for effecting alleviating or treating the various diseases or disorders recited herein. Optionally, or alternately, the instructional material may describe one or more methods of alleviating the diseases or disorders in a cell or a tissue of an animal. The instructional material of the kit may, for example, be affixed to a container that contains the nucleic acid, peptide, and/or compound of the invention or be shipped together with a container which contains the nucleic acid, peptide, and/or compound. Alternatively, the instructional material may be shipped separately from the container with the intention that the recipient uses the instructional material and the compound cooperatively.

As used in the definitions herein, each occurrence of $R^a$ is independently H, OH, alkyl (optionally substituted with one or more $R^4$), alkoxy (optionally substituted with one or more $R^4$), halo, trifluoromethyl, alkanoyloxy (optionally substituted with one or more $R^4$), methylenedioxy, benzyloxy (optionally substituted with one or more $R^4$), phenyloxy (optionally substituted with one or more $R^4$), naphthyloxy (optionally substituted with one or more $R^4$), nitro, trifluoromethoxy, nitrile, alkenyl (optionally substituted with one or more $R^4$), alkynyl, sulfoxide, sulfonyl, sulfonamido, aryl (optionally substituted with one or more $R^4$), heteroaryl (optionally substituted with one or more $R^4$), aryloyl (optionally substituted with one or more $R^4$), heteroaryloyl (optionally substituted with one or more $R^4$), heteroaryloxy (optionally substituted with one or more $R^4$), heteroarylmethyloxy (optionally substituted with one or more $R^4$), alkanoyl, alkoxycarbonyl, alkylaminocarbonyl, or amino.

As used herein, in the definitions presented each occurrence of $R^4$ is independently $(C_1-C_{20})$alkyl, $(C_2-C_{20})$alkenyl, $(C_2-C_{20})$alkynyl, halo, nitrile, nitro, $(C_5-C_{50})$aryl, $(C_3-C_{50})$ heteroaryl having at least one heteroatom selected from N, O, and S; $(C_5-C_{50})$aryl$(C_1-C_{20})$alkyl, heteroaryl$(C_1-C_{20})$alkyl, $(C_5-C_{50})$aryloxy$(C_1-C_{20})$alkyl, heteroaryloxy$(C_1-C_{20})$alkyl, $(C_5-C_{50})$arylamino$(C_1-C_{20})$alkyl, heteroarylamino$(C_1-C_{20})$alkyl, amino$(C_1-C_{20})$alkyl, —$R^x$—C(=O)—$R^y$, —$R^x$—O—$R^z$, or -L-Y.

"Alkyl," as used herein, refers to an aliphatic hydrocarbon chain of 1 to about 20 carbon atoms, preferably 1 to 10 carbon atoms, more preferably, 1 to 6 carbon atoms, and even more preferably, 1 to 4 carbon atoms and includes straight and branched chains such as methyl, ethyl, n-propyl, isopropyl, n-butyl, isobutyl, sec-butyl, tert-butyl, n-pentyl, isopentyl, neo-pentyl, n-hexyl, and isohexyl. Lower alkyl refers to alkyl having 1 to 4 carbon atoms. Alkyl groups can be optionally substituted with one or more $R^a$, as defined herein.

"Alkylenyl," as used herein, refers to a divalent counterpart of "alkyl," as defined herein (e.g., methyleneyl, ethyleneyl, propyleneyl, etc.). Alkylenyl groups can be optionally substituted with one or more $R^a$, as defined herein.

"Alkenyl" or "olefinic," as used herein, refers to an alkyl group of at least two carbon atoms having one or more double bonds, wherein alkyl is as defined herein. Alkenyl groups can be optionally substituted with one or more $R^a$, as defined herein.

"Hydroxy$(C_1-C_{20})$alkyl," as used herein, refers to an alkyl group, as defined herein, substituted with at least one hydroxy group.

"Hydroxy$(C_2-C_{20})$alkenyl," as used herein, refers to an alkenyl group, as defined herein, substituted with at least one hydroxy group.

"Alkynyl," as used herein, refers to an alkyl group of at least two carbon atoms having one or more triple bonds, wherein alkyl is as defined herein. Alkynyl groups can be optionally substituted with one or more $R^a$, as defined herein.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl. Aryl groups can be optionally substituted with one or more $R^a$, as defined herein.

"Heteroaryl," as used herein, refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrrolyl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups can be optionally substituted with one or with one or more $R^a$, as defined herein.

"$(C_5-C_{50})$Aryl$(C_1-C_{20})$alkyl," as used herein, refers to the group R—R'— where R is an aryl group and R' is an alkylenyl, as defined herein.

"Heteroaryl$(C_1-C_{20})$alkyl," as used herein, refers to the group R—R'— where R is a heteroaryl group and R' is an alkylenyl, as defined herein.

"$(C_5-C_{50})$aryloxy$(C_1-C_{20})$alkyl," as used herein, refers to the group R—O—R'— where R is an aryl group and R' is an alkylenyl, as defined herein.

"Heteroaryloxy$(C_1-C_{20})$alkyl," as used herein, refers to the group R—O—R'— where R is a heteroaryl group and R' is an alkylenyl, as defined herein.

"$(C_5-C_{50})$arylamino$(C_1-C_{20})$alkyl," as used herein, refers to the group R—NH—R'— where R is an aryl group and R' is an alkylenyl, as defined herein.

"Heteroaryloxyamino$(C_1-C_{20})$alkyl," as used herein, refers to the group R—NH—R'— where R is a heteroaryl group and R' is an alkylenyl, as defined herein.

"Amino$(C_1-C_{20})$alkyl," as used herein, refers to the group N(R")—R'— where R" is a hydrogen or $(C_1-C_6)$alkyl group and R' is an alkylenyl, as defined herein.

"Cycloalkyl," as used herein, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

"Heterocycloalkyl," as used herein, refers to an optionally substituted, cycloalkyl group having one or more rings in their structures having from 2 to about 20 carbon atoms (and all combinations and subcombinations of ranges and specific numbers of carbon atoms therein), with from 2 to about 10 carbon atoms being preferred, in addition to at least one heteroatom independently selected from the group consisting of N, O and S. Multi-ring structures may be bridged or fused ring structures. Groups include, but are not limited, to aziridinyl, pyrrolidinyl, pyrrolidino, piperidinyl, piperidino, piperazinyl, piperazino, morpholinyl, morpholine, thiomorpholinyl, thiomorpholino, tetrahydrofuranyl, tetrahydrothiofuranyl, tetrahydropyranyl, and pyranyl.

"Halo" or "halogen," as used herein, refers to chloro, bromo, fluoro, and iodo.

"Alkoxy," as used herein, refers to the group R—O— where R is an alkyl group of 1 to 6 carbon atoms.

"Alkoxycarbonyl," as used herein, refers to the group R—O—C(=O)— where R is an alkyl group of 1 to 6 carbon atoms.

"Alkanoyl," as used herein, refers to the group R—C(=O)— where R is an alkyl group of 1 to 6 carbon atoms.

"Alkanoyloxy," as used herein, refers to the group R—C(=O)—O— where R is an alkyl group of 1 to 6 carbon atoms.

"Alkylaminocarbonyl," as used herein, refers to the group R—NH—C(=O)— where R is an alkyl group of 1 to 6 carbon atoms.

"Alkylcarbonylamino," as used herein, refers to the group R—C(=O)—NH where R is an alkyl group of 1 to 6 carbon atoms.

"Heteroarylmethyl," as used herein, refers to the group R—$CH_2$— where R is a heteroaryl group, as defined herein.

"Heteroarylmethyloxy," as used herein, refers to the group R—$CH_2$—O— where R is a heteroaryl group, as defined herein.

"Heteroaryloxy," as used herein, refers to the group R—O— where R is a heteroaryl group, as defined herein.

"Heteroarylmethyloxy," as used herein, refers to the group R—$CH_2$—O— where R is a heteroaryl group, as defined herein.

"Heterocycle" or "heterocyclyl," as used herein, refers to a stable 5- to 7-membered monocyclic or bicyclic or 7- to 10-membered bicyclic heterocyclic ring, or radical thereof, that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. Preferably, the total number of S and O atoms in the heterocycle is not more than one. Examples of heterocycles include, but are not limited to, 1H-indazole, 2-pyrrolidonyl, 2H,6H-1,5,2 dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Sulfoxide," as used herein, refers to a compound or moiety containing the group —S(=O)—.

"Sulfonamido," as used herein, refers to a moiety containing the group —$S(O)_2NH$—.

"Sulfonyl," as used herein, refers to a moiety containing the group —$S(O)_2$—.

"Aliphatic linkage," as used herein, refers to any divalent alkylenyl group (e.g., methyleneyl, ethyleneyl, propyleneyl, etc.), including groups having the general formula —$(CH_2)_m$—, wherein m is an integer from 1 to 6.

"Aromatic linkage," as used herein, refers to any divalent aryl group, such as a —$(C_6H_4)$— group.

"Residue of an imageable moiety," or simply "imageable moiety," as used herein, refers to any moiety, as generally known in the art and as specifically defined herein, that comprises one or more groups capable of detection either directly or indirectly in an in vivo or in vitro diagnostic imaging procedure, and comprises, e.g., one or more moieties that emit or may be caused to emit detectable radiation (e.g., by radioactive decay, fluorescence excitation, spin resonance excitation, etc.), groups that affect local electromagnetic fields (e.g., paramagnetic, superparamagnetic, ferromagnetic, or ferromagnetic species), groups that absorb or scatter radiation energy (e.g., chromophores, particles (including gas or liquid containing vesicles), heavy elements and compounds thereof, etc.), and groups that generate a detectable substance (e.g., gas microbubble generators). Examples of imageable moieties may be selected from the group consisting of a gamma ray emitting radioisotopes, positron emitting radioisotopes, a magnetic resonance imaging contrast agents (e.g., gadolinium chelates), X-ray contrast agents (e.g., iodinated radiopaque aromatic compounds), or an ultrasound contrast agent (e.g., liposomes comprising an echogenic compound).

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes a selective inhibitor of arginase. In one embodiment, the compound of the invention comprises an alpha-amino acid, or a derivative thereof, with a first substituent and a second substituent on the alpha-carbon (Cα). The first substituent comprises a moiety selected from the group consisting of a boronic acid and N-hydroxy guanidine. The other substituent is a moiety comprising a proximal nitrogen, wherein the proximal nitrogen is basic and separated from the alpha-carbon by a linker of two to four carbon atoms.

In a non-limiting aspect, the presence of the proximal nitrogen, which is basic, linked through a $C_2$-$C_4$ chain to the alpha carbon imparts unexpected properties to the compound of the invention. In a non-limiting example, the compounds of the invention may inhibit both arginases (arginase I and arginase II) in a-pH insensitive manner. This is a significant improvement over known boronic acid-type inhibitors such as ABH (2(S)-amino-6-boronohexanoic acid) and BEC (S-(2-boronoethyl)-L-cysteine).

The physiological pH of the human body (i.e., the pH of the fluid in subcellular or cellular components, tissues, or organs) is 7.35 to 7.45. Although pH in certain cellular microenvironments (e.g., subcellular compartments such as mitochondria) may be more basic (with a pH as high as 8.5), most normal physiology is thought to occur at physiological pH (see Abad et al., 2004, J. Biol. Chem. 279:11521-11529). However, the optimal catalytic activity of arginase I or II occurs at a very basic pH of 9.5. Most in vitro arginase enzymatic assays are performed at the optimal catalytic activity pH (i.e., pH 9.5), even though this pH value is not particularly physiologically relevant. For a more physiologically relevant quantitation of arginase inhibition, the enzyme assay should be performed at or near a pH 7.5, but the inhibitory potency of known boronic acid-type inhibitors (such as ABH and BEC) is much lower at pH 7.5 than at pH 9.5 (Colleluori & Ash, 2001, Biochem. 40, 9356-9362).

In a non-limiting embodiment, the compounds of the invention do not exhibit a decrease in arginase inhibitory potency when the pH is changed from 9.5 to 7.5. In another non-limiting embodiment, the arginase inhibitory potency of the compounds of the invention is higher at pH <9.5 than at pH 9.5. For example, as the experimental pH was decreased from 9.5 to 7.5, Example 8 showed an increase in human arginase I inhibitory potency and did not show much change in human arginase II inhibitory potency. Based on their improved inhibitory potencies at physiological pH (as compared to the known boronic acid-type inhibitors), the compounds of the invention have unexpectedly improved biological effects on arginase in vivo. Thus, the compounds of the invention may more effectively modulate or control diseases characterized by abnormally high arginase activity or abnormally low nitric oxide levels than the known boronic acid-type inhibitors.

In a non-limiting embodiment, the inhibitors of the invention selectively inhibit arginase I over arginase II at a pH value lower than 9.5 (i.e., the $pIC_{50}$ for arginase I is higher than the $pIC_{50}$ for arginase II at a pH value lower than 9.5). In another non-limiting embodiment, the proximal nitrogen-containing moiety is selected so that the compound of the invention more selectively inhibits arginase I over arginase II (i.e., the $pIC_{50}$ for arginase I is higher than the $pIC_{50}$ for arginase). In another non-limiting example, if the proximal nitrogen in a compound of the invention is part of a heterocyclic group comprising an amide, urea or sulfonamide functionality, the selectivity of the compound for arginase I over arginase II is significantly higher than for a compound of the invention lacking such structural feature.

Compounds of the Present Invention

In one aspect, the invention includes a compound comprising an alpha-amino acid with two substituents on the alpha carbon. The first substituent comprises a moiety selected from the group consisting of a boronic acid and N-hydroxy guanidine. The second substituent comprises a moiety comprising a proximal nitrogen, wherein the proximal nitrogen is basic and linked to the alpha-carbon (Cα) by a two-to-four carbon chain ($C_2$-$C_4$ chain).

In one embodiment, the compound is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propylhexanoic acid, or 2-amino-6-borono-2-(3-(4-(3-methoxyphenylcarbamoyl)piperazin-1-yl)propyl hexanoic acid.

In a non-limiting embodiment, the first substituent is capable of interacting with arginase residues. The first substituent includes, for example, a boronic acid, N-hydroxyguanidine, and other known equivalents/substitutes. In one embodiment, the first substituent is a boronic acid. The invention contemplates boronic acids having backbones of different lengths. In another embodiment, the first substituent comprises a boronic acid linked to the alpha-carbon through a n-butyl group.

In a non-limiting embodiment, the second substituent is capable of establishing binding interactions in the outer active site cleft and the region flanking the outer active site clefts of parasitic arginase, bacterial arginase, arginase I or arginase II. To the extent this substituent may form strong interactions with the target arginase protein, compounds with increased potency or selectivity over the compounds disclosed in the prior art may be identified. The second substituent comprises a carbon chain and a proximal nitrogen. In one embodiment, the proximal nitrogen is attached to the alpha carbon via a two-to-four carbon chain. In another embodiment, the proximal nitrogen is attached to the alpha carbon by a three carbon chain. In yet another embodiment, the proximal nitrogen is basic. In yet another embodiment, the proximal nitrogen is part of a primary, secondary or tertiary amine group.

In a non-limiting aspect, if the carbon chain is less than 4 carbon atoms long, having the proximal nitrogen as part of a heterocyclic group facilitates compound synthesis and reduces the degree or possibility of cyclization of the proximal nitrogen with the alpha carboxylic acid. In one embodiment, the carbon chain is not branched. In another embodiment, the carbon chain is substituted with at least one $C_1$-$C_4$ alkyl group. In yet another embodiment, the carbon chain is part of the heterocyclic group comprising the proximal nitrogen.

In one embodiment, the invention includes a compound of formula (I) or (II), or a salt thereof:

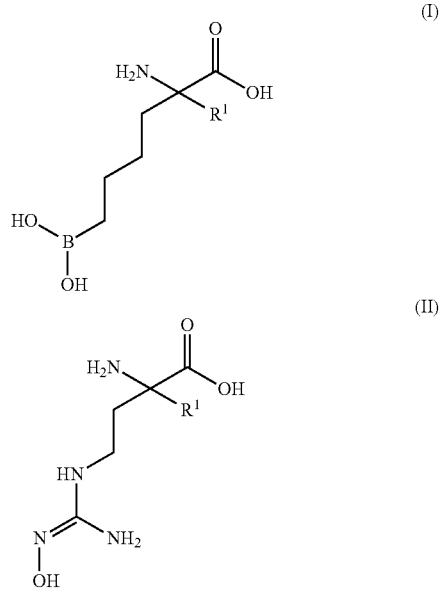

wherein:
$R^1$ is $(C_{2-4})$—N(Z)Y;
$C_{2-4}$ is a chain of two, three or four carbons;

N is a proximal nitrogen;

Z is H, alkyl, cycloalkyl, heterocycloalkyl, aryl, heteroaryl, arylalkyl, or alkoxyalkyl;

Y is H, alkyl, cycloalkyl, heterocycloalkyl, aryl, heteroaryl, arylalkyl, or alkoxyalkyl;

wherein, if Z and Y are cyclic, Z and Y may be discrete or linked to form bridged or fused groups; and wherein Z and Y may be discrete or bonded together with the N to form a common heterocycloalkyl group, which may contain one or more heteroatoms and may be optionally substituted with alkyl, amino, halo, alkylamino, dialkylamino, aryl, heteroaryl, amide, arylsulfonyl, alkylsulfonyl, sulfonamide, arylcarbonyl, alkylcarbonyl, urea, cyano, hydroxy, alkoxy, aralkoxy, aryloxy, aminocarboxy, arylalkyl, or heteroarylalkyl.

Suitable heterocyclic groups contemplated within the invention include, for example, aziridine, azetidine, pyrrolidine, piperidine, azepane, azocane, diazetidine imidazolidine, pyrazolidine, oxazolidine, isoxazolidine, thiazolidine, isothiazolidine, piperazine, morpholine, bridged analogs thereof, fused combinations thereof, and substituted versions thereof.

Substituents on the heterocyclic groups may comprise one or more of the following groups: $(C_1$-$C_6)$alkyl, halo, aryl and heteroaryl, aryl$(C_1$-$C_6)$alkyl, heteroaryl$(C_1$-$C_6)$alkyl, —C(=O)$R^3$, —SO$_2R^3$, —CONH$R^3$, COO$R^3$, O$R^2$ and N$R^3R^3$, with the proviso that if the at least one substituent is O$R^2$ or N$R^3R^3$, then the at least one substituent is not attached to the same carbon atom as the nitrogen atom of the heterocyclic group.

$R^2$ is H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O)(aryl), —C(=O)(heteroaryl), —SO$_2(C_1$-$C_6)$alkyl, —SO$_2$(aryl), —SO$_2$(heteroaryl), —CONH$(C_1$-$C_6)$alkyl, —CONH(aryl), or —CONH(heteroaryl).

Each occurrence of $R^3$ is independently H, $(C_1$-$C_6)$alkyl, aryl, heteroaryl, aryl$(C_1$-$C_6)$alkyl, or heteroaryl$(C_1$-$C_6)$alkyl.

In one subembodiment, the compound of formula (I) is not 2-amino-6-borono-2-(3-(piperazin-1-yl)propyl)hexanoic acid, 2-(3-(4-acetylpiperazin-1-yl)propyl)-2-amino-6-boronohexanoic acid, 2-amino-6-borono-2-(3-(4-(4-cyanobenzoyl)piperazin-1-yl)propylhexanoic acid, or 2-amino-6-borono-2-(3-(4-(3-methoxyphenylcarbamoyl)piperazin-1-yl)propyl hexanoic acid.

In one embodiment, the invention includes a compound of formula (III) or a salt thereof:

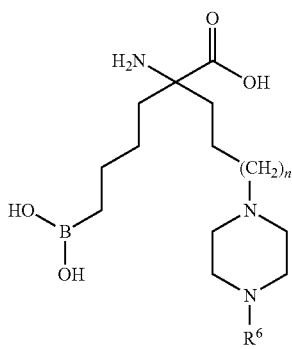

(III)

wherein, n is 0, 1 or 2; and, $R^5$ is H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O) (aryl), —C(=O)(heteroaryl), —SO$_2(C_1$-$C_6)$alkyl, —SO$_2$ (aryl), —SO$_2$(heteroaryl), —CONH$(C_1$-$C_6)$alkyl, —CONH (aryl), or —CONH(heteroaryl).

In one subembodiment, $R^5$ is phenyl, benzyl, acetamide, benzamide, or substituted benzamide.

In one embodiment, the invention includes a compound of formula (IV) or a salt thereof:

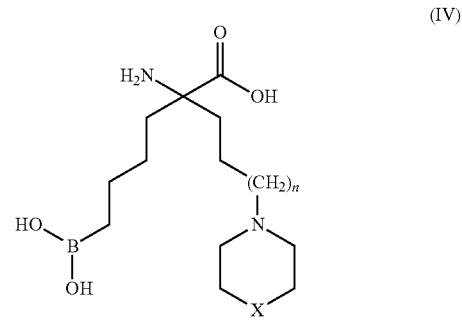

(IV)

wherein:

n is 0, 1 or 2;

X is N$R^5$, C$R^6R^7$, O, S, S(=O) or S(O)$_2$;

$R^7$ is H, OH, O$R^8$, CN or N$R^8R^9$; and $R^5$, $R^6$, $R^8$ and $R^9$ are independently H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O)(aryl), —C(=O)(heteroaryl), —SO$_2(C_1$-$C_6)$alkyl, —SO$_2$(aryl), —SO$_2$(heteroaryl), —CONH$(C_1$-$C_6)$alkyl, —CONH(aryl), or —CONH(heteroaryl).

In one subembodiment, X is N$R^5$. In another embodiment, $R^5$ is phenyl, benzyl, acetamide, benzamide, or substituted benzamide.

In one embodiment, the heterocyclic group is bridged. Non-limiting examples of compounds of the invention with bridged heterocyclic groups are as follows:

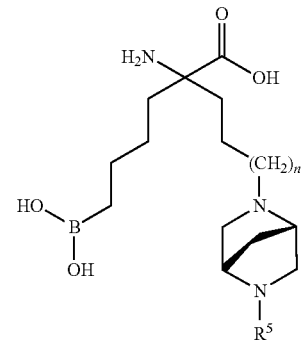

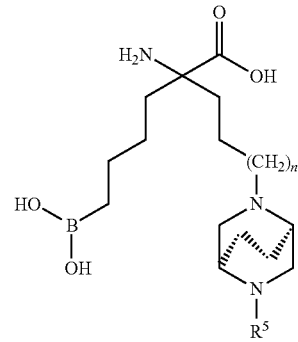

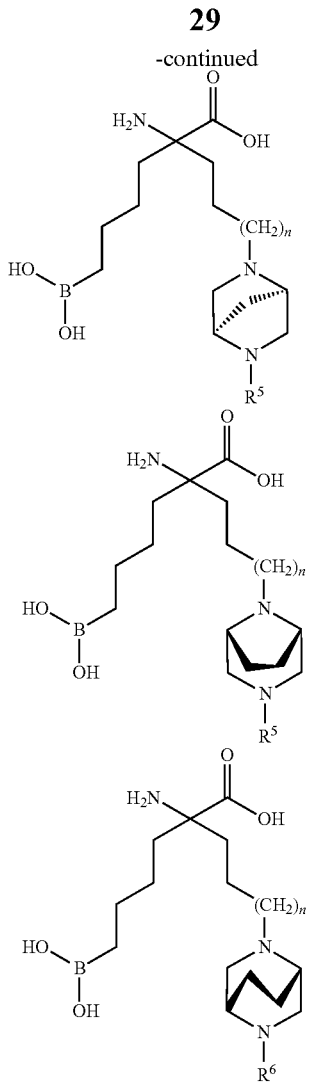

wherein:

n is 0, 1 or 2; and, $R^5$ is H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O)(aryl), —C(=O)(heteroaryl), —SO$_2$$(C_1$-$C_6)$alkyl, —SO$_2$(aryl), —SO$_2$(heteroaryl), —CONH$(C_1$-$C_6)$alkyl, —CONH(aryl), or —CONH(heteroaryl).

In one embodiment, the heterocyclic group is substituted with an amino group or comprises an amino group. Non-limiting examples of such compounds are illustrated below:

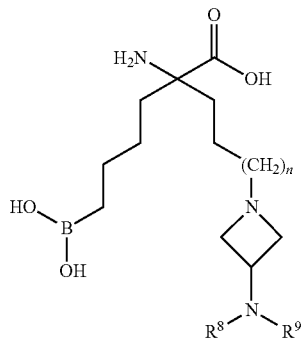

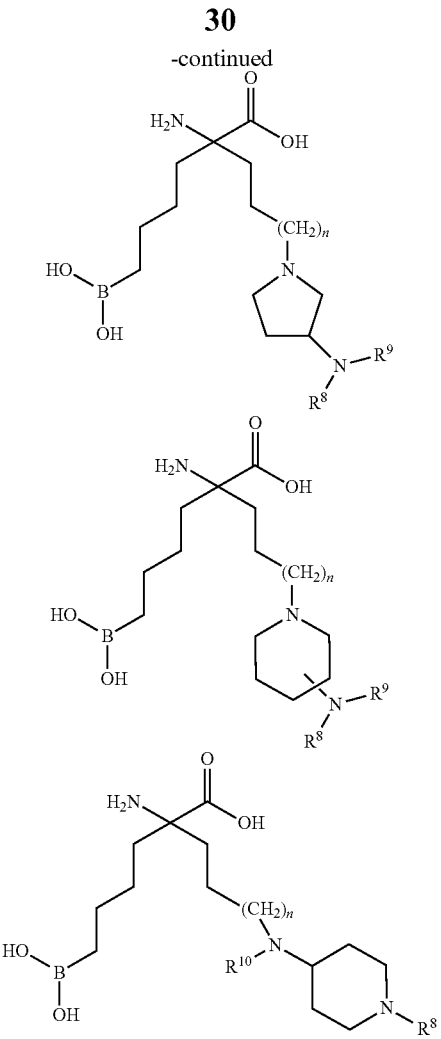

wherein:

n is 0, 1 or 2;

$R^8$ and $R^9$ are independently H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O)(aryl), —C(=O)(heteroaryl), —SO$_2$$(C_1$-$C_6)$alkyl, —SO$_2$(aryl), —SO$_2$(heteroaryl), —CONH$(C_1$-$C_6)$alkyl, —CONH(aryl), or —CONH(heteroaryl).; and $R^{10}$ is H, $(C_1$-$C_6)$ alkyl or arylalkyl.

In one embodiment, the invention includes a compound of formula (V) or a salt thereof:

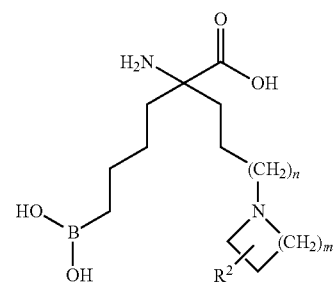

(V)

wherein:

m is 1, 2, 3 or 4;

n is 0, 1 or 2; and, $R^2$ is H, $(C_1$-$C_6)$alkyl, aryl, heteroaryl, aryl$(C_1$-$C_6)$alkyl, heteroaryl$(C_1$-$C_6)$alkyl, —C(=O)$(C_1$-$C_6)$alkyl, —C(=O)

(aryl), —C(=O)(heteroaryl), —SO₂(C₁-C₆)alkyl, —SO₂(aryl), —SO₂(heteroaryl), —CONH(C₁-C₆)alkyl, —CONH(aryl), or —CONH(heteroaryl).

Substituents on the heterocyclic groups may comprise one or more of the following groups: $(C_1-C_6)$alkyl, halo, aryl and heteroaryl, aryl$(C_1-C_6)$alkyl, heteroaryl$(C_1-C_6)$alkyl, —C(=O)$R^3$, —SO₂$R^3$, —CONH$R^3$, COO$R^3$, O$R^2$ and N$R^3R^3$, with the proviso that if the at least one substituent is O$R^2$ or N$R^3R^3$, then the at least one substituent is not attached to the same carbon atom as the nitrogen atom of the heterocyclic group.

$R^2$ is H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO₂$(C_1-C_6)$alkyl, —SO₂(aryl), —SO₂(heteroaryl), —CONH$(C_1-C_6)$alkyl, —CONH(aryl), or —CONH(heteroaryl).

Each occurrence of $R^3$ is independently H, $(C_1-C_6)$alkyl, aryl, heteroaryl, aryl$(C_1-C_6)$alkyl, or heteroaryl$(C_1-C_6)$alkyl.

In one embodiment, the invention includes a compound of formula (VI) or a salt thereof:

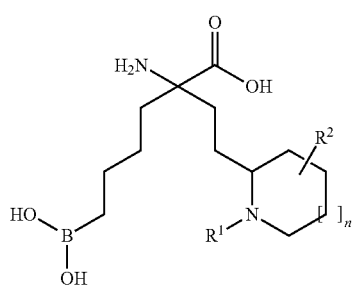
(VI)

wherein:

n is 0, 1 or 2; and $R^1$ is H, alkyl or arylalkyl; and, $R^2$ is H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO₂$(C_1-C_6)$alkyl, —SO₂(aryl), —SO₂(heteroaryl), —CONH$(C_1-C_6)$alkyl, —CONH(aryl), or —CONH(heteroaryl).

In one embodiment, the heterocyclic group is fused with another cyclic group. Non-limiting examples of such an embodiment are illustrated below:

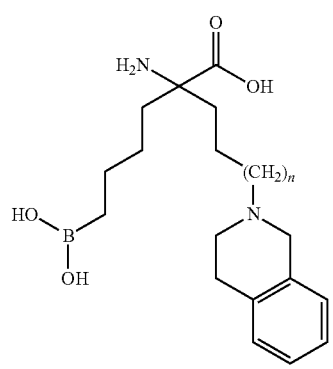

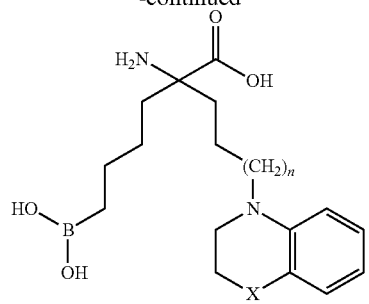

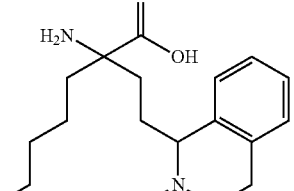

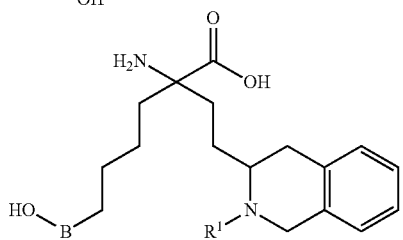

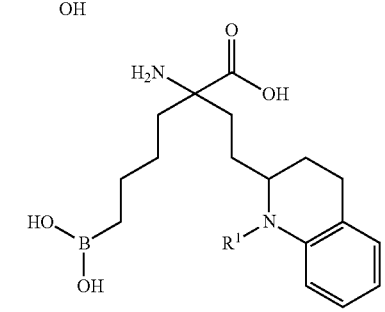

wherein:
n is 0, 1 or 2;
$R^1$ is H, alkyl or arylalkyl;
X is N$R^5$, C$R^6R^7$, O, S, S(O), or S(O)₂;
wherein, if X is C$R^6R^7$, then $R^7$ is H, OH, O$R^8$, CN or N$R^8R^9$; and,
$R^5$, $R^6$, $R^8$ and $R^9$ are independently H, $(C_1-C_6)$alkyl, aryl, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO₂$(C_1-C_6)$alkyl, —SO₂(aryl), —SO₂(heteroaryl), —CONH$(C_1-C_6)$alkyl, —CONH(aryl), or —CONH(heteroaryl).

The aryl ring may be optionally substituted with one or more of the following groups: H, $(C_1-C_6)$alkyl, aryl, halo, heteroaryl, aryl$(C_1-C_6)$alkyl, heteroaryl$(C_1-C_6)$alkyl, —C(=O)$(C_1-C_6)$alkyl, —C(=O)(aryl), —C(=O)(heteroaryl), —SO₂$(C_1-C_6)$alkyl, —SO₂(aryl), —SO₂(heteroaryl), —CONH$(C_1-C_6)$alkyl, —CONH(aryl), or —CONH(heteroaryl).

Substituents on the heterocyclic groups may comprise one or more of the following groups: $(C_1-C_6)$alkyl, halo, aryl and heteroaryl, aryl(C$_1$-C$_6$)alkyl, heteroaryl(C$_1$-C$_6$)alkyl, —C(=O)R$^3$, —SO$_2$R$^3$, —CONHR$^3$, COOR$^3$, OR$^2$ and NR$^3$R$^3$, with the proviso that if the at least one substituent is OR$^2$ or NR$^2$R$^3$, then the at least one substituent is not attached to the same carbon atom as the nitrogen atom of the heterocyclic group.

R$^2$ is H, (C$_1$-C$_6$)alkyl, aryl, heteroaryl, aryl(C$_1$-C$_6$)alkyl, heteroaryl(C$_1$-C$_6$)alkyl, —C(=O)(C$_1$-C$_6$)alkyl, —C(=O)(aryl), —C(=O)(heteroaryl), —SO$_2$(C$_1$-C$_6$)alkyl, —SO$_2$(aryl), —SO$_2$(heteroaryl), —CONH(C$_1$-C$_6$)alkyl, —CONH(aryl), or —CONH(heteroaryl).

Each occurrence of R$^3$ is independently H, (C$_1$-C$_6$)alkyl, aryl, heteroaryl, aryl(C$_1$-C$_6$)alkyl, or heteroaryl(C$_1$-C$_6$)alkyl.

In one embodiment, the proximal nitrogen atom is part of an aniline or pyridine group. Non-limiting examples of such an embodiment are illustrated below:

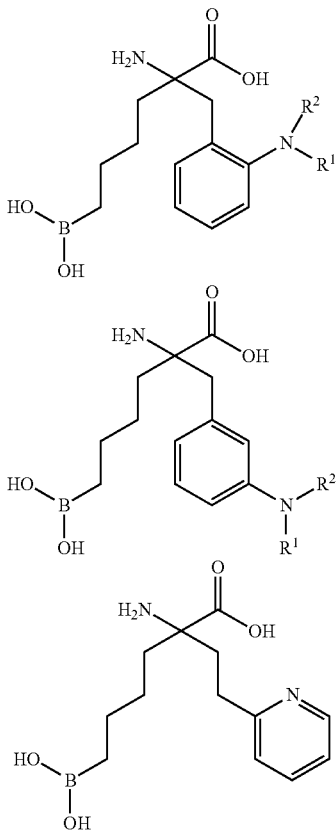

wherein R$^1$ and R$^2$ are independently H, C$_1$-C$_6$ alkyl or arylalkyl. In one embodiment, the compound is not 2-amino-6-(borono-2-(pyridine-3-ylmethyl)hexanoic acid.

The aryl or heteroaryl ring may be optionally substituted with one or more of the following groups: H, (C$_1$-C$_6$)alkyl, aryl, halo, heteroaryl, aryl(C$_1$-C$_6$)alkyl, heteroaryl(C$_1$-C$_6$)alkyl, C$_1$-C$_6$)alkyl, —C(=O)(aryl), —C(=O)(heteroaryl), —SO$_2$(C$_1$-C$_6$)alkyl, —SO$_2$(aryl), —SO$_2$(heteroaryl), —CONH(C$_1$-C$_6$)alkyl, —CONH(aryl), or —CONH(heteroaryl).

Substituents on the heterocyclic groups may comprise one or more of the following groups: (C$_1$-C$_6$)alkyl, halo, aryl and heteroaryl, aryl(C$_1$-C$_6$)alkyl, heteroaryl(C$_1$-C$_6$)alkyl, —C(=O)R$^3$, —SO$_2$R$^3$, —CONHR$^3$, COOR$^3$, OR$^2$ and NR$^3$R$^3$, with the proviso that if the at least one substituent is OR$^2$ or NR$^2$R$^3$, then the at least one substituent is not attached to the same carbon atom as the nitrogen atom of the heterocyclic group.

R$^2$ is H, (C$_1$-C$_6$)alkyl, aryl, heteroaryl, aryl(C$_1$-C$_6$)alkyl, heteroaryl(C$_1$-C$_6$)alkyl, —C(=O)(C$_1$-C$_6$)alkyl, —C(=O)(aryl), —C(=O)(heteroaryl), SO$_2$(C$_1$-C$_6$)alkyl, —SO$_2$(aryl), —SO$_2$(heteroaryl), —CONH(C$_1$-C$_6$)alkyl, —CONH(aryl), or —CONH(heteroaryl).

Each occurrence of R$^3$ is independently H, (C$_1$-C$_6$)alkyl, aryl, heteroaryl, aryl(C$_1$-C$_6$)alkyl, or heteroaryl(C$_1$-C$_6$)alkyl.

In one embodiment, the invention includes a compound of formula (VII) or a salt thereof:

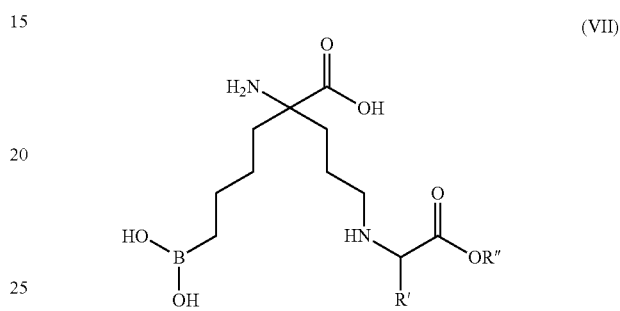

wherein:
R' is H, C$_1$-C$_6$ alkyl, benzyl, substituted benzyl, CH$_3$SCH$_2$CH$_2$—, CH$_3$S(=O)CH$_2$CH$_2$—, CH$_3$S(O)$_2$CH$_2$CH$_2$—, 3-indol-1H-yl-methyl, HSCH$_2$—, —CH$_2$CH$_2$C(=O)NH$_2$, —CH$_2$C(=O)NH$_2$, CH$_2$CH$_2$C(=O)OH, —CH$_2$C(=O)OH, —CH(OH)CH$_3$, —CH$_2$OH, —(CH$_2$)$_4$NH$_2$, —(CH$_2$)$_3$NHC(=NH)NH$_2$, or imidazole-4-yl-methyl;
R" is H or C$_1$-C$_6$ alkyl.

In one embodiment, the invention includes a compound of formula (VIII) or a salt thereof:

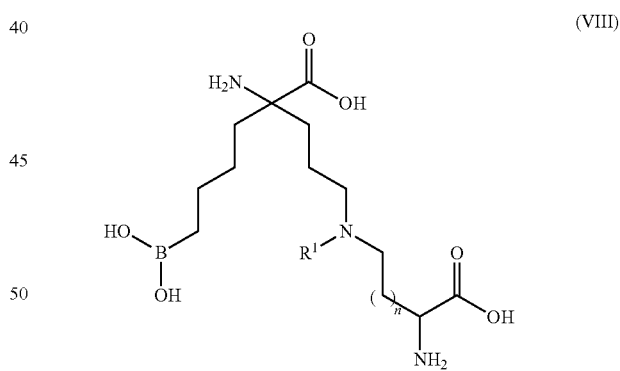

wherein:
n is 0, 1, 2 or 3;
R' is H or C$_1$-C$_6$ alkyl.

The compounds of the invention contain chiral centers, providing for various stereoisomeric forms such as diastereomeric mixtures, enantiomeric mixtures as well as optical isomers. The individual optical isomers can be prepared directly through asymmetric or stereospecific synthesis or by conventional chiral separation of optical isomers from the enantiomeric mixture.

Some of the compounds of the present invention may contain chiral centers beyond the Cα, and such compounds may exist in the form of stereoisomers (i.e. enantiomers or diastereoisomers). The present invention includes all such stereoisomers and any mixtures thereof including racemic mixtures. Racemic mixtures of the stereoisomers, as well as the substantially pure stereoisomers, are within the scope of the invention. The term "substantially pure," as used herein, refers to at least about 90 mole %, more preferably at least about 95 mole %, even more preferably at least about 98 mole %, and even more preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques et al., Enantiomers, Racemates and Resolutions (Wiley Interscience, New York, 1981); Wilen, S. H. et al., 1977, Tetrahedron, 33:2725; Eliel, E. L., Stereochemistry of Carbon Compounds, (McGraw-Hill, N.Y., 1962); Wilen, S. H. Tables of Resolving Agents and Optical Resolutions, p. 268 (E. L. Eliel, Ed., University of Notre Dame Press, Notre Dame, Ind. 1972).

In certain preferred embodiments, the compounds are the L-stereoisomer forms, similarly to the compounds illustrated below:

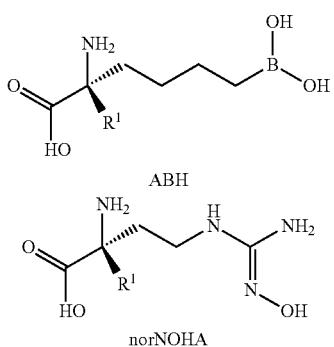

In one non-limiting aspect, structural and functional studies described herein have suggested that the "L" stereochemistry of each amino acid (as defined above) facilitates tight binding in the enzyme active site; "D" stereoisomers do not appear to bind as tightly or appear to be less efficacious. Alternatively stated, the preferred stereochemistry is analogous to the stereospecific replacement of the (R)-hydrogen in ABH by $R^1$. Depending on the relative priority of the two substituents at the alpha carbon, the compound may have either R- or S-stereochemistry. Typically the inhibitory activities of the R- and S-stereoisomers may differ, and therefore the preferred stereochemistry is the form that more effectively permits the molecule to function as an arginase inhibitor. In this regard, in one non-limiting aspect, structural and functional studies have suggested that the αC stereochemistry as defined above is preferred for tight binding in the enzyme active site; whereas stereoisomers with the opposite configuration do not bind as tightly or are less efficacious.

Alternatively, the stereoisomers may be defined where the ProS hydrogen of glycine depicted below is replaced by the $X^1$ that fits into the enzyme active site. The second substituent, $R^1$, replaces the ProR hydrogen of glycine. According to the Calm-Ingold-Prelog rules, the designation R or S for the stereoisomers depends upon the hierarchy based on the atoms connected to the chiral carbon. For the preferred compounds of the present invention where the ProS H is replaced with —$(CH_2)_4B$ and the ProR H is replaced with the functionalities —$(CH_2)_{2-4}N$— the stereochemistry at the αC is R. For the preferred compounds of the invention where the ProS H is replaced with the norNOHA functionality and the ProR H is replaced with the functionality —$(CH_2)_2N$—, the stereochemistry at the αC is R. However, if the Pro R H is replaced with the functionalities —$(CH_2)_{3-4}N$—, the stereochemistry at the αC is S.

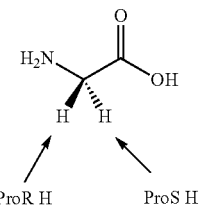

The invention includes prodrugs of the aminoacid of the invention or prodrugs of one of the binding moieties (such as the boronic acid or N-hydroxyguanidine, for example). "Prodrug," as used herein, means a compound which is convertible in vivo by metabolic means (e.g., by hydrolysis) to a compound of the present invention. Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed). "Design and Application of Prodrugs," Textbook of Drug Design and Development, Chapter 5, 113-191 (1991), Bundgaard et al., 1992, J. Drug Deliv. Rev. 8:1-38, Bundgaard, 1988, J. Pharm. Sci. 77:285 et seq.; and Higuchi and Stella (eds.), Prodrugs as Novel Drug Delivery Systems, American Chemical Society (1975). In a non-limiting embodiment, the esters of the alpha-carboxylic acid are prepared as prodrugs to improve oral bioavailability, whereby the ester is stable in the stomach and gastrointestinal tract, is optimally transported across the lining of the gastrointestinal tract into the bloodstream, and is then converted by the ubiquitous esterases in the blood and/or in the liver to the carboxylic acid moiety. A similar ester strategy could be performed on the boronic acid moiety. Indeed, a dual ester pro-drug strategy on both the carboxylic acid and the boronic acid moieties may be utilized.

Non-limiting examples of ester prodrugs contemplated within the invention are provided below:

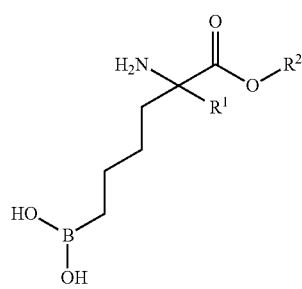

wherein:

$R^1$ may be defined as in any compound disclosed elsewhere herein;

$R^2$ is selected from the group consisting of $C_1$-$C_6$ alkyl, $C_3$-$C_7$ cycloalkyl, tetrahydrofuran-2-yl-methyl, tetrahydrofuran-3-yl-methyl, $C_3$-$C_7$ cycloalkyl-methyl, 2-($C_3$-$C_7$ cycloalkyl)-ethyl, dihydrofuran-2(3H)-one-4-yl-methyl, 2-hydroxyl-ethyl, 2-hydroxyl-2-methyl-ethyl, phenyl, 2-tolyl, 3-tolyl, 4-tolyl, 2-methoxy-phenyl, 3-methoxy-phenyl, 4-methoxy-phenyl, 2,3-dihydro-1H-inden-4-yl, 2,3-dihydro-1H-inden-5-yl, thiazol-2-yl-methyl, thiazol-4-yl-methyl, imidazole-2-yl-$(CH_2)_n$—, imidazole-4-yl-$(CH_2)_n$—, 2-methyl-1H-benzo[d]imidazole-2-yl-$(CH_2)_n$—, $R^5C(=O)OCH_2CH_2$—, $R^5C(=O)OCH(CH_3)CH_2$—, $R^5C(=O)OCH_2$—, or $R^5C(=O)OCH(CH_3)$—;

n is 1, 2, 3 or 4;

$R^5$ is H, $C_1$-$C_6$ alkyl, $C_3$-$C_7$ cycloalkyl, aryl, heteroaryl, or $CH(R^6)NH_2$; and $R^6$ is H, $C_1$-$C_6$ alkyl, benzyl, substituted benzyl, $CH_3SCH_2CH_2$—, $CH_3S(=O)CH_2CH_2$—, $CH_3S(O)_2CH_2CH_2$—, 3-indol-1H-yl-methyl, $HSCH_2$—, —$CH_2CH_2C(=O)NH_2$, —$CH_2C(=O)NH_2$, $CH_2CH_2C(=O)OH$, —$CH_2C(=O)OH$, —$CH(OH)CH_3$, —$CH_2OH$, —$(CH_2)_4NH_2$, —$(CH_2)_3NHC(=NH)NH_2$, or imidazole-4-yl-methyl.

The benzoimidazole may be optionally substituted with at least one substituent selected from the group consisting of ($C_1$-$C_6$)alkyl, halo and ($C_1$-$C_6$)alkoxy.

Further, the amino acid of the invention may exist in unsolvated as well as in solvated forms, with pharmaceutically acceptable solvents such as water, ethanol, and the like. In general, the solvated forms are considered equivalent to the unsolvated forms for the purpose of the present invention.

Synthesis of Compounds of the Invention

The compounds of the present invention may be prepared in a number of ways well known to those skilled in the art. The compounds may be synthesized, for example, by the methods described below, or variations thereon as appreciated by the skilled artisan. The reagents used in the preparation of the compounds of this invention may be either commercially obtained or may be prepared by standard procedures described in the literature. All processes disclosed in association with the present invention are contemplated to be practiced on any scale, including milligram, gram, multigram, kilogram, multikilogram or commercial industrial scale. One skilled in the art will appreciate that the syntheses of such second substituent groups at the α-position of an amino acid is a difficult synthetic process as judged by the lack of commercially available α,α-disubstituted amino acids. See, e.g., Vogt et al., 2007, Org. Biomol. Chem. 5:406-30.

FIGS. 1-14 illustrate selected general mechanisms for preparing the compounds of the present invention. FIG. 1 schematically illustrates the solution-phase syntheses of useful starting materials 4a (R=methyl), 4b (R=ethyl), and 4c (R=t-butyl). As illustrated in FIG. 1, the hydrochloride salt of a glycine alkyl ester 2a-c is reacted with benzophenone imine (O'Donnell, et al., 1982, J. Org. Chem. 47:2663) at room temperature to give the corresponding ketimine protected glycine ester 4a-c. This transimination is particularly useful for tert-butyl ester 4e. Alternatively, alkyl esters of α-bromoacetic acid 3a-c can be reacted with benzophenone in refluxing acetonitrile as shown in the second reaction resulting in 4a-c (O'Donnell, 2004, Acc. Chem. Res. 37:506).

Figure 2:
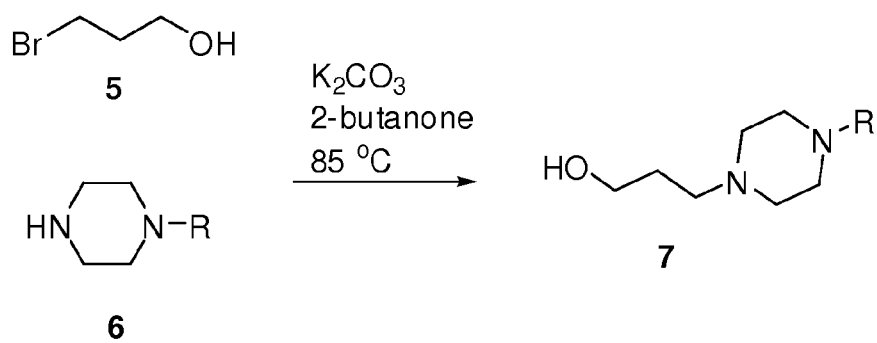
FIG. 2 is a scheme illustrating the synthesis of selected starting materials.
Figure 2:
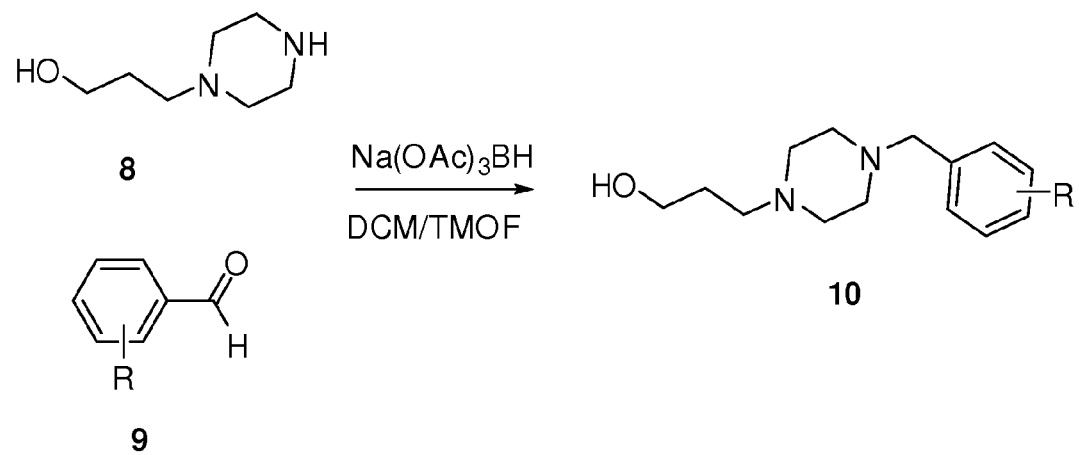
Figure 2:
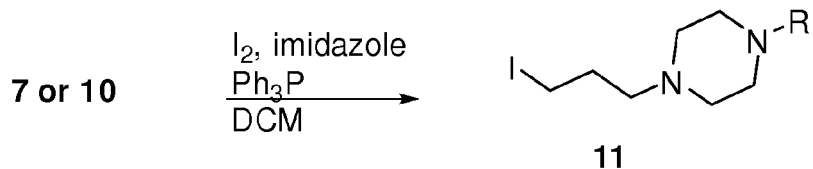

FIG. 2 illustrates the synthesis of additional selected starting materials. As illustrated in FIG. 2, compound 7 is prepared by reacting substituted or unsubstituted piperazines (6) with 3-bromo-1-propanol (5) in the presence of a base, such as potassium carbonate, at elevated temperature for several hours. When R is alkyl or arylalkyl, this starting material can be prepared by reacting 8 with an aldehyde 9 under reductive amination conditions to yield 10. Upon isolation of product 7 or 10, they may be converted to the alkyl iodide (11) by reaction with iodine in the presence of imidazole and triphenylphosphine (Garegg & Samuelsson, 1979, J. Chem. Soc. Chem. Commun. 978). Alternatively, resin-bound triphenylphosphine may also be used to generate compound 11, which may be used in alkylation steps as $R^1$—X in accordance with the methods herein (Classon et. al., 1988, J. Org. Chem., 53:6126).

Figure 3:
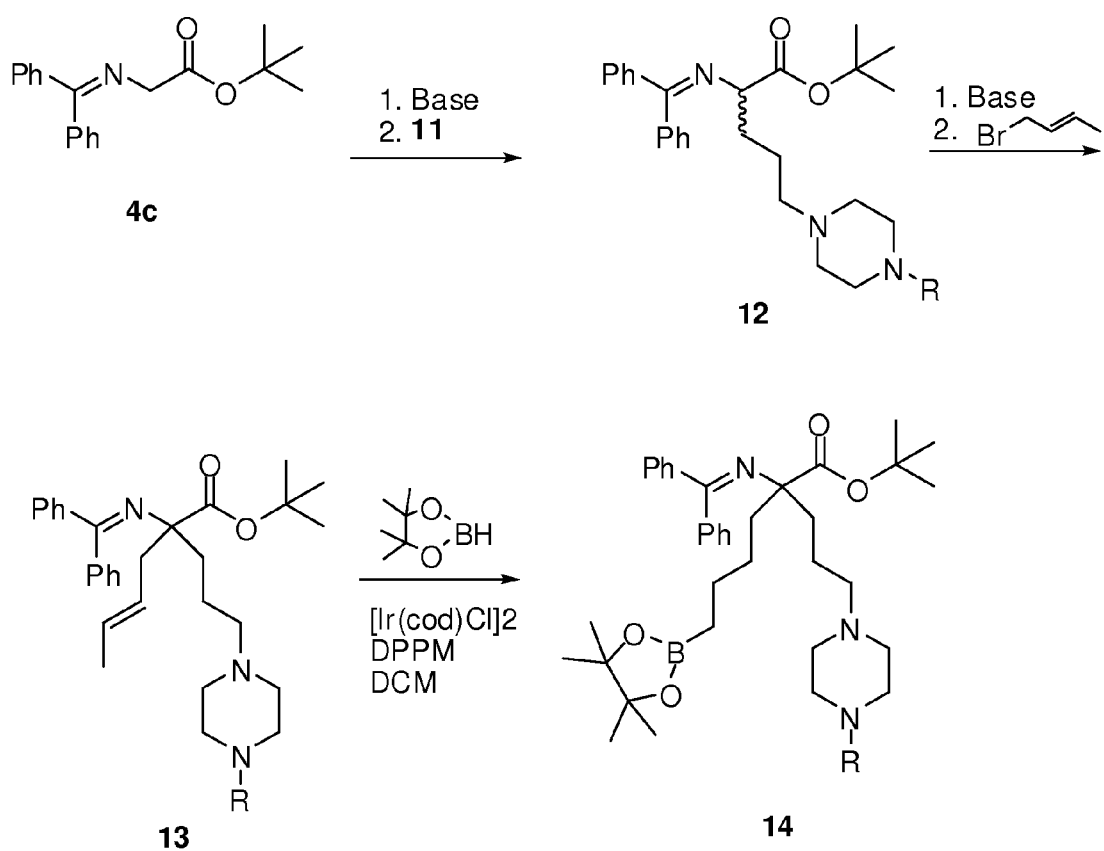
FIG. 3 is a scheme illustrating a non-limiting example of solution-phase synthesis of a compound of the invention.

FIG. 3 illustrates an exemplary solution-phase synthesis of compound 1 of the invention, where the $R^1$ side chain contains variously substituted piperazines. Compound 4c is reacted with LiHMDS at low temperature as described in Reddy et al., 2007, Org. Biomol. Chem. 5:889, and then one equivalent of 11 is added and allowed to react at room temperature for several hours to yield compound 12. The second side chain may be introduced by treating intermediate compound 12 with a strong base such as n-BuLi, LDA, or the preferred base KHMDS under anhydrous conditions at low temperature and then adding one equivalent of crotyl bromide to yield compound 13. Hydroboration of the crotyl side chain to give the boronate ester side chain is accomplished by treatment with pinacol borane in the presence of iridium catalyst (similar to procedure reported by Yamamoto et al., 2004, Tetrahedron 60:10695), to yield compound 14.

Figure 4:
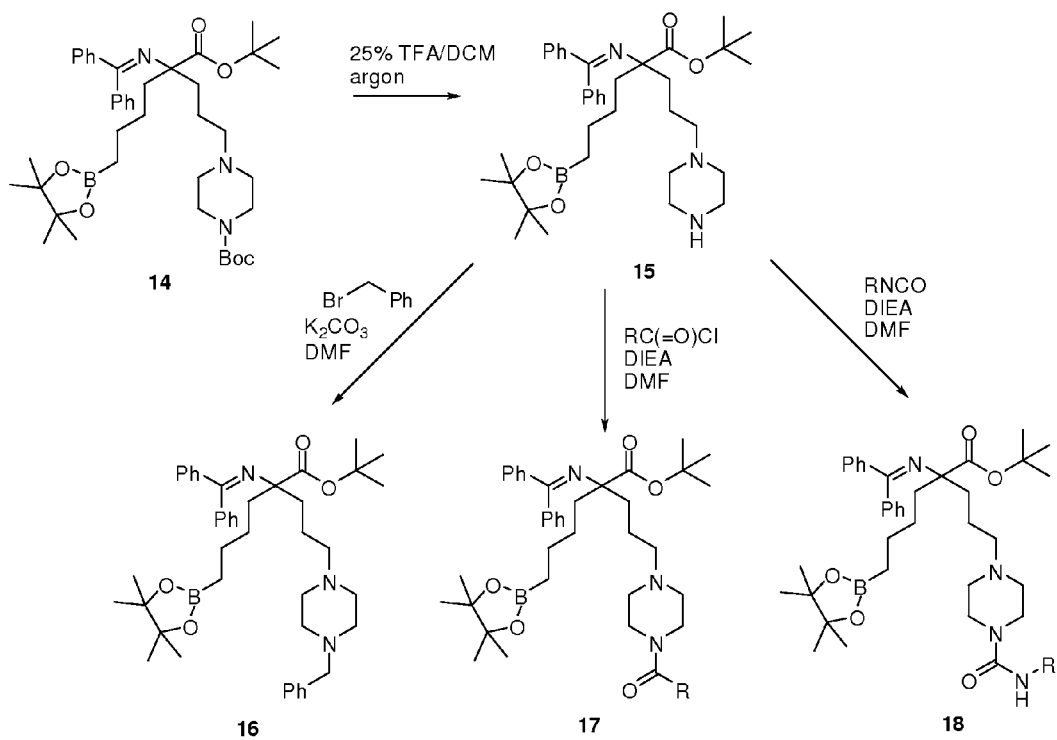
FIG. 4 is a scheme illustrating the synthesis of selected starting materials.

When R=Boc in compound 14 additional moieties may be introduced by the synthetic scheme outlined in FIG. 4. Compound 14 is treated with 25% TFA/DCM under anhydrous conditions under argon for 30 min to one hour resulting in compound 15. This intermediate can be reacted in anhydrous DMF with excess potassium carbonate and an alkyl or arylalkyl halide to give compound 16. Additionally, 15 can be acylated either with an acid chloride to give compound 17 or with an isocyanate to give urea 18.

Figure 5:
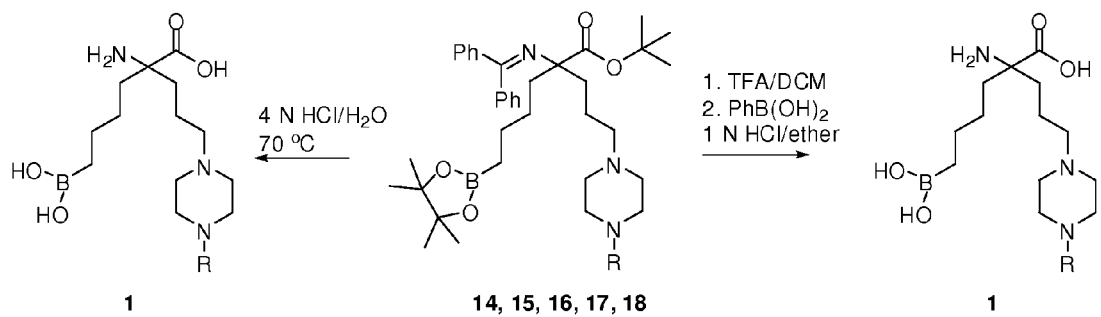
FIG. 5 is a scheme illustrating the deprotection of amino acids.

Compounds 14, 15, 16, 17, and 18 may be globally deprotected to give final products 1 as described in FIG. 5. Depending on the stability of the R group in compound 14-18, this compound may be treated with 4 N HCl at 70° C. for several hours or in a two step procedure where the t-butyl ester is removed first using 50-100% TFA in DCM for 1-2 hr, followed by reacting this intermediate with excess phenyl boronic acid in 1 N aqueous HCl and diethyl ether for several hours.

Figure 6:
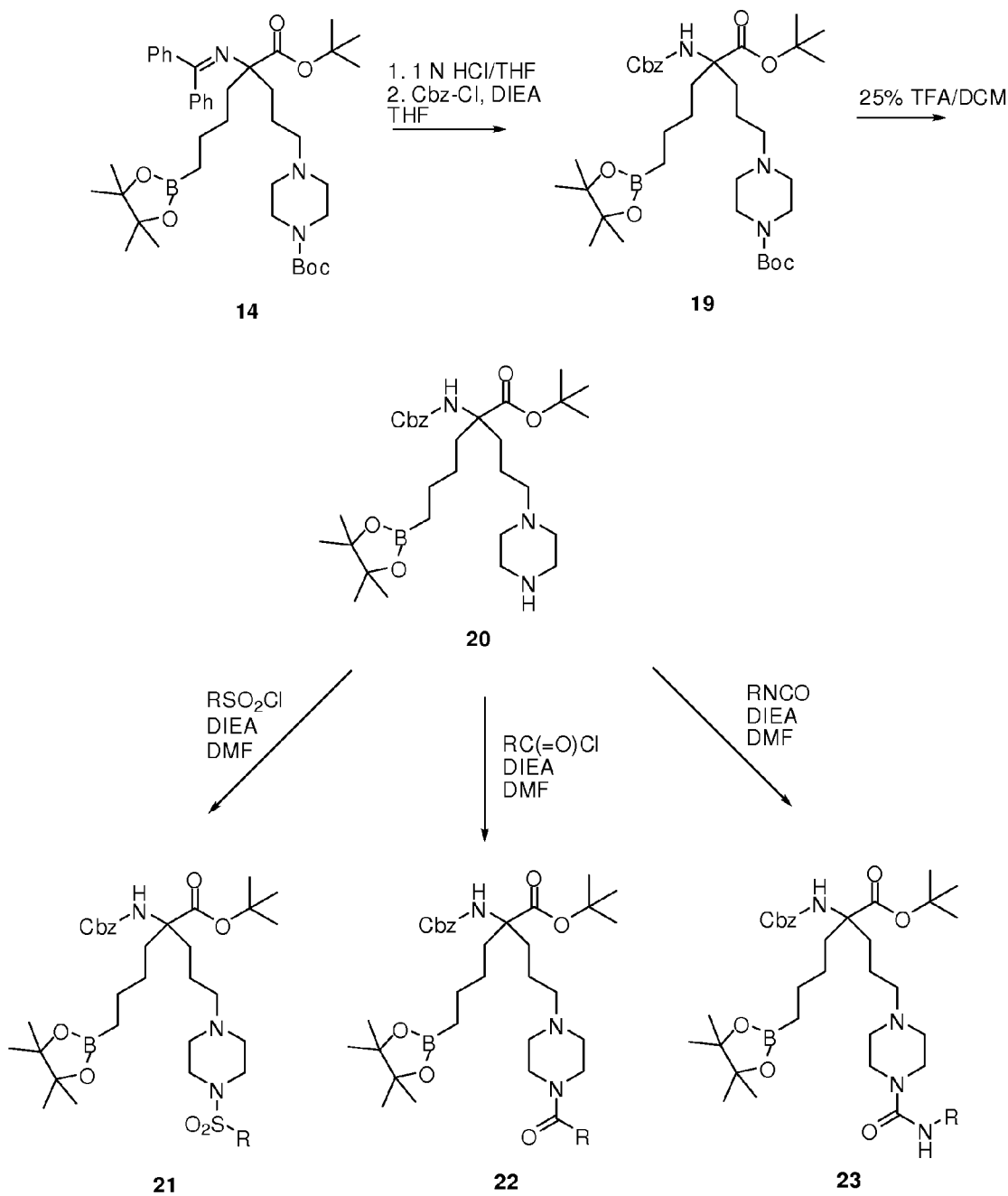
FIG. 6 is a scheme illustrating the synthesis of a compound of the invention.
Figure 7:
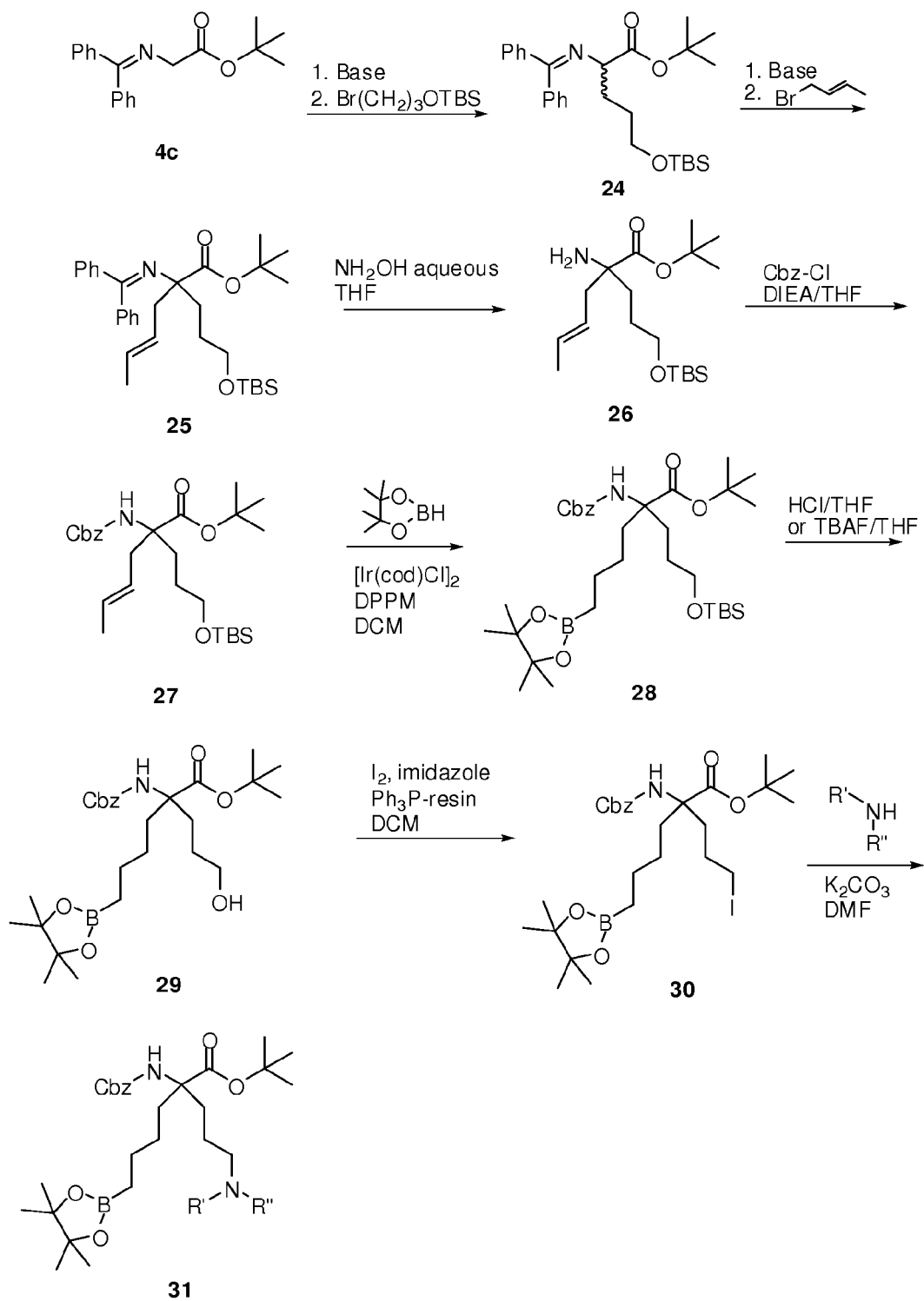
FIG. 7 is a scheme illustrating an alternative synthesis of a compound of the invention.

The compounds of this invention 1 may also be synthesized as outlined in FIGS. 6 and 7. The ketimine protecting group in compound 14 may be cleaved by treatment with 1 N HCl in THF at 0° C. or room temperature for 15 min to 1 hr and then this α-amine may be reprotected by reaction with benzyl chloroformate to yield compound 19. The Boc group on this intermediate may be removed by treatment with 25% TFA/DCM under for 30 min to yield compound 20, which may be acylated with sulfonyl chlorides to yield sulfonamides 21, acid chlorides to yield amides 22 or isocyanates to give urea 23.

The synthesis outlined in FIG. 7 starts with compound 4c being treated with LiHMDS at low temperature as described in Reddy et al., 2007, Org. Biomol. Chem. 5:889, and then 1 equivalent of 3-bromopropoxy-t-butyldimethylsilane is added and allowed to react at room temperature for several hours to give compound 24. The second side chain may be introduced by treating intermediate compound 24 with a strong base such as n-BuLi, LDA, or the preferred base KHMDS under anhydrous conditions at low temperature and then adding 1 equivalent of crotyl bromide to give compound 25. The ketimine protecting group on 25 is removed selectively by treating with 1 N hydroxyl amine hydrochloride in THF (1:2) for several hours and the resulting α-amine 26 is protected by treating with benzyl chloroformate under basic conditions to yield 27. Hydroboration of the crotyl side chain to give the boronate ester side chain is accomplished by treatment with pinacol borane in the presence of iridium catalyst similar to that reported by Yamamoto et al., 2004, Tetrahedron 60:10695, to yield compound 28. Removal of the TBS protecting group and functionalization of the hydroxyl group is achieved by treating 28 with mild aqueous acid in organic solution or TBAF to yield intermediate 29 followed by reacting with iodine in the presence of triphenylphosphine and imidazole to yield 30. Various nucleophilic amines maybe reacted with 30 under basic conditions in DMF to yield 31. These nucleophilic amines may include reagents leading to compounds 20-23 as well as many others leading to compound 1 of the invention.

Figure 8:
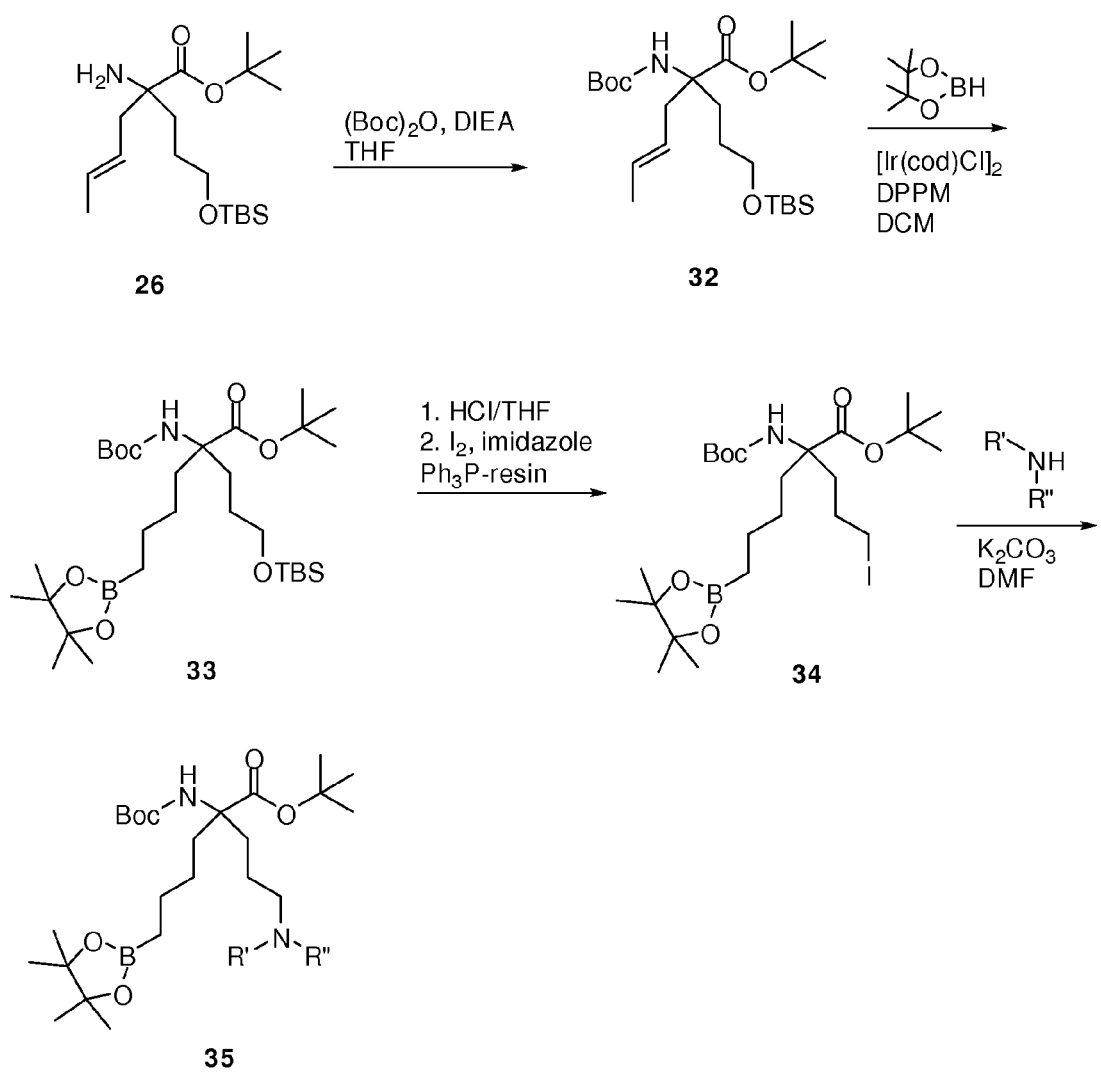
FIG. 8 is a scheme illustrating an alternative synthesis of a compound of the invention.
Figure 9:
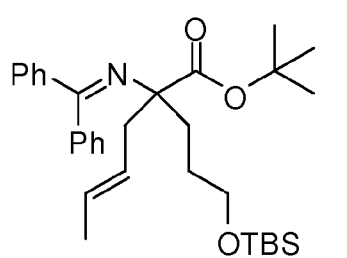
FIG. 9 is a scheme illustrating a protective group manipulation used in the synthesis of a compound of the invention.
Figure 9:
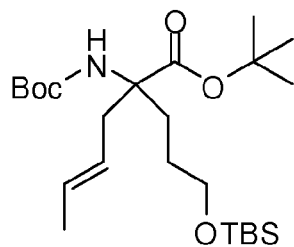
Figure 9:
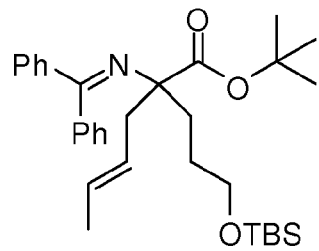
Figure 9:
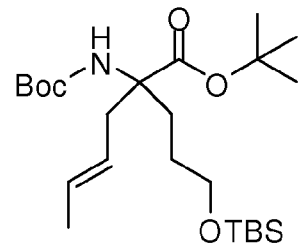

The compounds 1 of the invention, as well as additional examples, may also be synthesized according to FIGS. 8 and 9. These synthetic schemes allow for improved deprotection methodologies as described elsewhere herein. The α-amine of intermediate 26 may be protected with a Boc group as outlined in FIG. 8 by treating it with Boc anhydride in the presence of a base such as DIEA in THF, yielding intermediate 32. Hydroboration of the crotyl side chain is accomplished by treatment with pinacol borane in the presence of iridium catalyst (similar to that reported by Yamamoto et al., 2004, Tetrahedron 60:10695) to give compound boronate ester 33. Removal of the TBS protecting group and functionalization of the hydroxyl group is achieved by treating 33 with mild aqueous acid in organic solution or TBAF followed by reacting with iodine in the presence of triphenylphosphine and imidazole to yield 34. Various nucleophilic amines can be reacted with 34 under basic conditions in DMF to yield 35. These nucleophilic amines may include reagents leading to compound 1 of the invention. Intermediate 32 may also be prepared from intermediate 25 by two different strategies (FIG. 9) where the ketimine is removed first with mild acidic hydrolysis that spares the TBS ether and this product is subsequently treated with Boc anhydride as described above. Alternatively, intermediate 25 may be treated with acid to remove both the ketimine and TBS ether. This product is reprotected in a two-step process involving treatment with Boc anhydride followed by protection of the hydroxyl group with TBS (using TBSCl in DCM and DMAP as a base).

Figure 10:
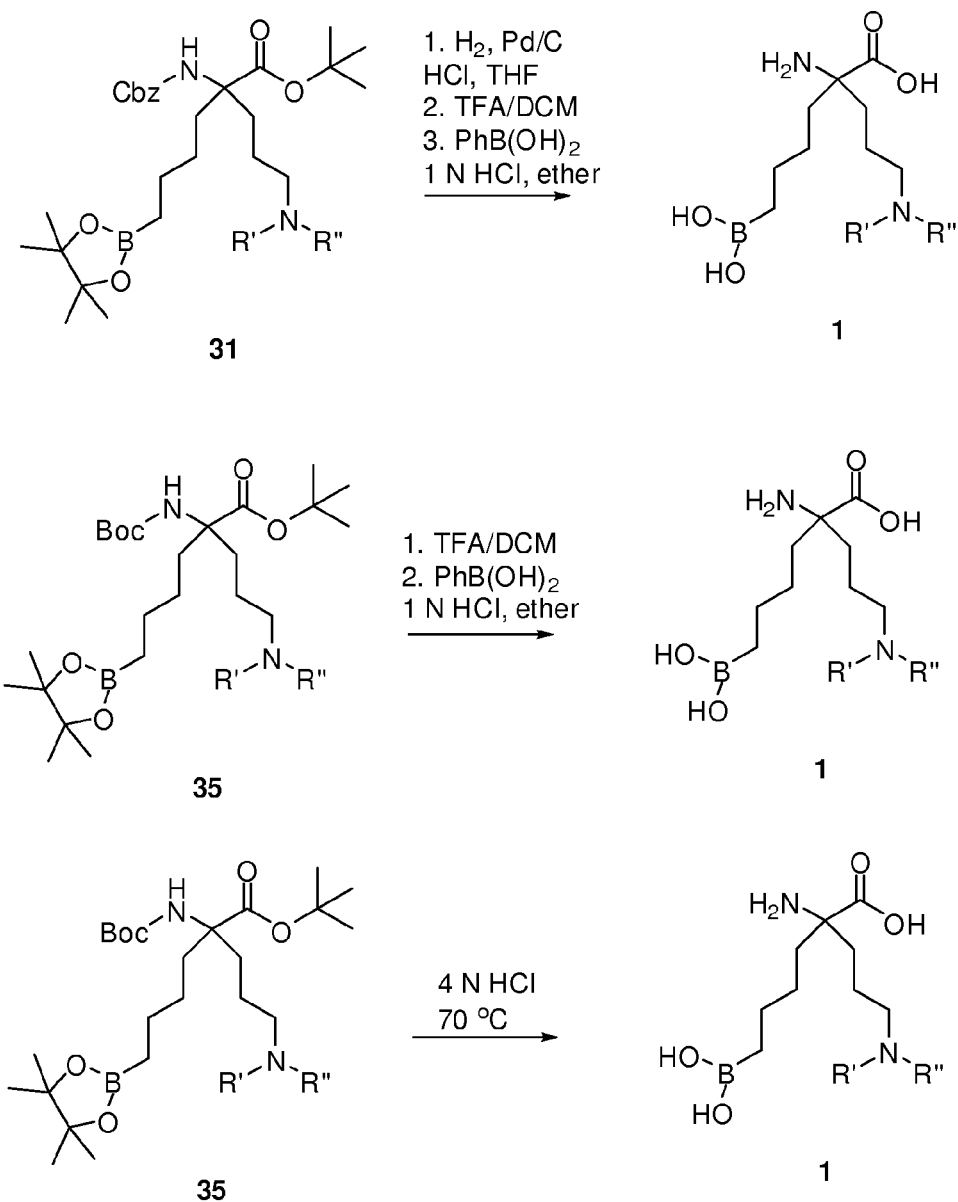
FIG. 10 is a scheme illustrating selected deprotection reactions used to generate a compound of the invention FIG. 11 a scheme illustrating selected chiral intermediates used to generate a compound 1.

FIG. 10 outlines the global deprotection schemes for compounds 20-23, 31, and 35 resulting in compound 1 of the present invention. Compounds 20-23, 31 are hydrogenolyzed in the presence of palladium on charcoal under acidic conditions with hydrogen at atmospheric pressure for a few hours to remove the Cbz protecting group. This intermediate is subsequently treated with 75-100% TFA in DCM for 1-2 hr followed by reacting with excess phenyl boronic acid in a mixture of 1 N aqueous HCl and diethyl ether to give compound 1. Compound 35 is globally deprotected in a two-step process involving Boc and t-butyl ester removal by treating it with 50-100% TFA for a few hours followed by reacting the product with excess phenyl boronic acid in a mixture of 1 N aqueous HCl and diethyl ether to give compound 1. Alternatively, compound 35 may be treated with 4 N aqueous HCl at 70-90° C. for a few hours resulting in compound 1. The choice of deprotection schemes illustrated in FIG. 10 is dependent on the stability of the NR'R" moieties to the corresponding reaction conditions.

As will be readily understood, functional groups present may contain protecting groups during the course of synthesis. Protecting groups are known per se as chemical functional groups that may be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., Protective Groups in Organic Synthesis 2d. Ed., Wiley & Sons, 1991.

The compounds of this invention contain chiral centers, providing for various stereoisomeric forms such as diastereomeric mixtures, enantiomeric mixtures as well as optical isomers. The individual optical isomers may be prepared directly through asymmetric or stereospecific synthesis or by conventional chiral separation of optical isomers from the enantiomeric mixture.

Figure 11:
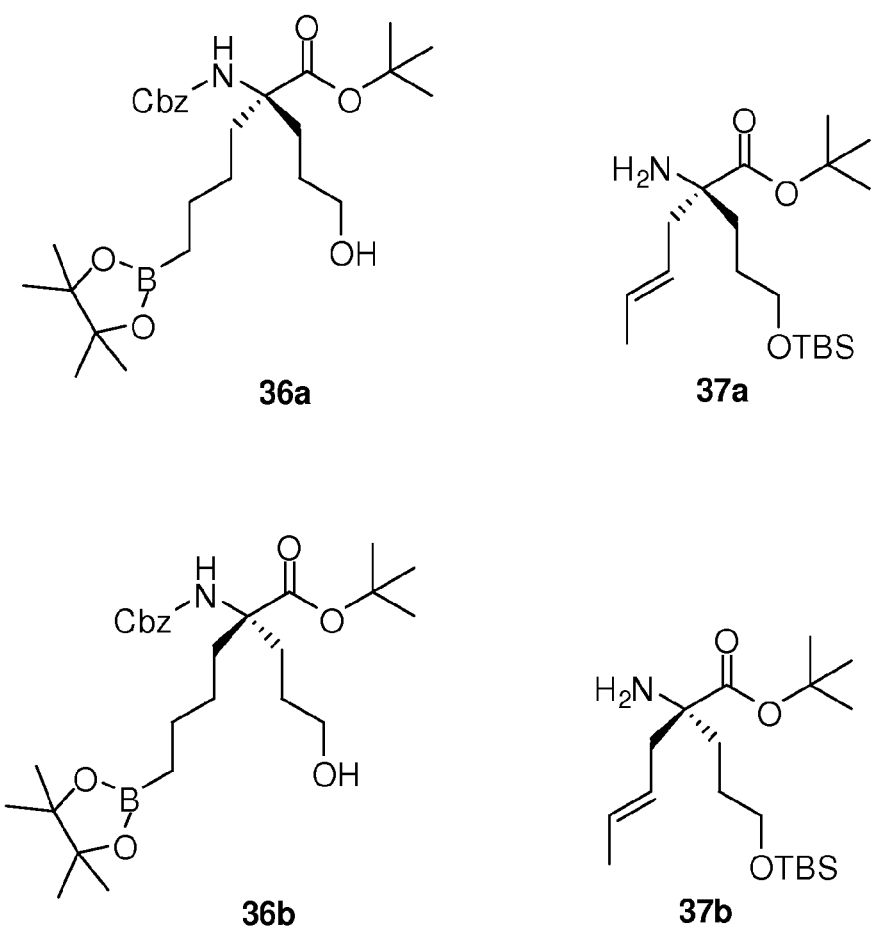

FIG. 11 illustrates selected intermediates from FIGS. 7-9 that may be used as enantiomeric intermediates to yield chiral compound 1. It is well known to those skilled in the art that chemistry outlined in FIGS. 7-10 may be used either with a racemic mixture or a single enantiomer with similar results. Thus, manipulation of 36a or 37a would lead to a single enantiomer of the desired compound 1. Additionally, 36b or 37b could be modified in a similar fashion leading to compound 1 with the opposite configuration. In a non-limiting embodiment, based on the chirality of the active enantiomer of ABH and how these molecules bind to the arginases, it is expected that the product 1 generated from enantiomers 36a or 37a would be active as an arginase inhibitor. Alternatively, chiral compounds 1 may be prepared via specific asymmetric synthesis or chiral resolution methods.

Figure 12:
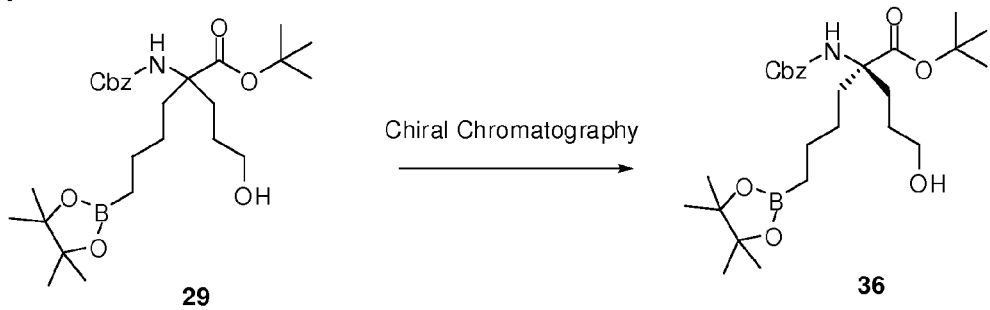
FIG. 12 is a scheme illustrating selected methods for resolving key racemic intermediates, and a chiral synthesis for compound 1.
Figure 12:
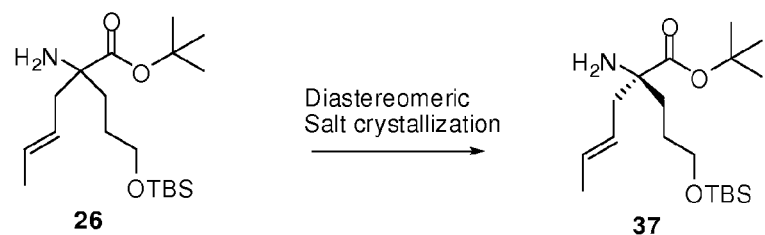
Figure 12:
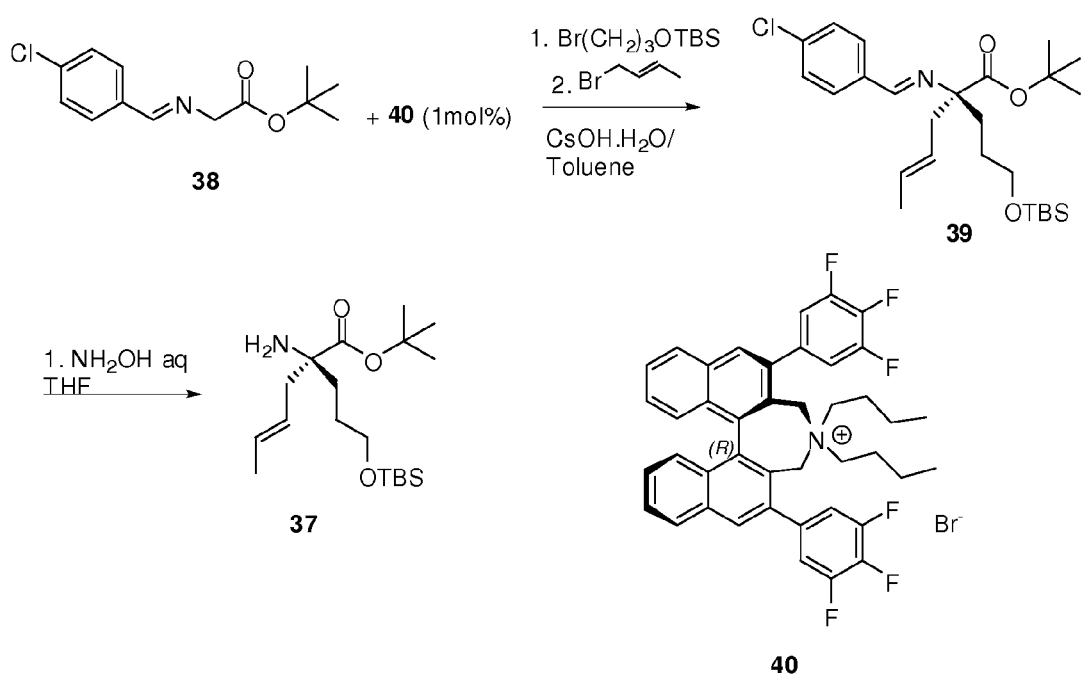

FIG. 12 illustrates methodologies to obtain the chiral intermediates in FIG. 11. For instance, as illustrated in scheme A in FIG. 12, HPLC or SFC methods using analytical and preparatory columns loaded with known chiral packing materials such as ChiralPak AD-H could be used to separate the racemic mixture 29 leading to chiral 36a and its enantiomer 36b. As illustrated in scheme B in FIG. 12, the amino ester 26 as a racemic mixture may be treated with an enantiomeric salt such as (+)-camphor sulfonic acid to yield diastereomeric salts. These salts may crystallize separately, and once the amino ester is freed from the crystalline salt the pure enantiomer (37a) is obtained.

Additional chiral acids could be utilized to prepare crystalline diastereomeric salts. These chiral acids would include (+) and (−) tartaric acid, (+) and (−) dibenzoyltartaric acid, (+) and (−) malic acid, (+) and (−) mandelic acid, (+) and (−) camphor sulphonic acid, (+) and (−) N-Boc phenylalanine, and (+) and (−) N-Boc valine among others. In one embodiment, the optimal diastereomeric salt has controllable crystallization kinetics and may be isolated in reproducibly high chiral purity.

Scheme C in FIG. 12 outlines a synthetic method reported in the literature to obtain α,α-disubstituted amino acids with a known chirality (Ooi et al., 2000, J. Am. Chem. Soc. 122: 5338, and Jiang et. al., 2008, Org. Proc. Res. Dev. 12:1164). Compound 38 is treated under phase transfer conditions sequentially with 3-bromopropoxy TBS ether and then crotyl bromide in the presence of a chiral catalyst (40) to give 39. The α-amine protecting group may then be hydrolyzed resulting in the desired chiral intermediate 37.

Figure 13:
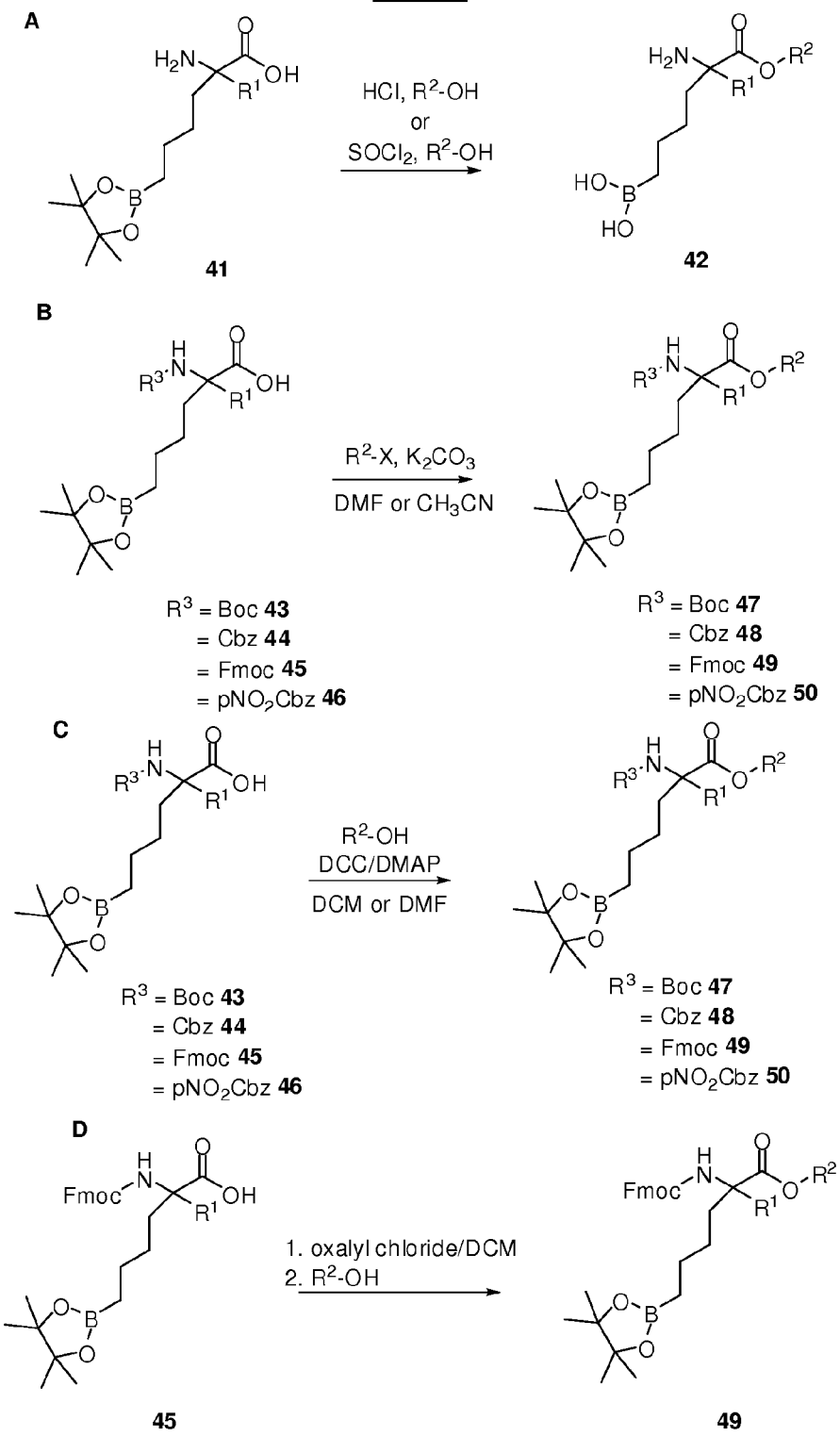
FIG. 13 is a scheme illustrating preparation of selected prodrug ester intermediates.
Figure 14:
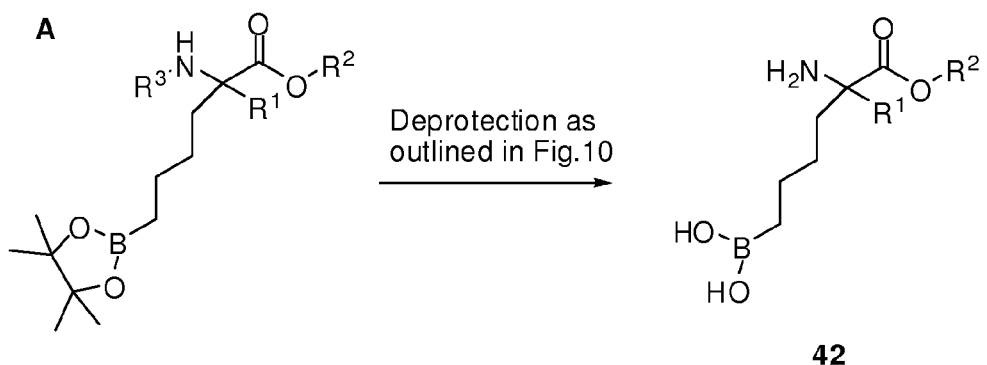
FIG. 14 is a scheme illustrating selected methods for global deprotection of prodrug esters.
Figure 14:
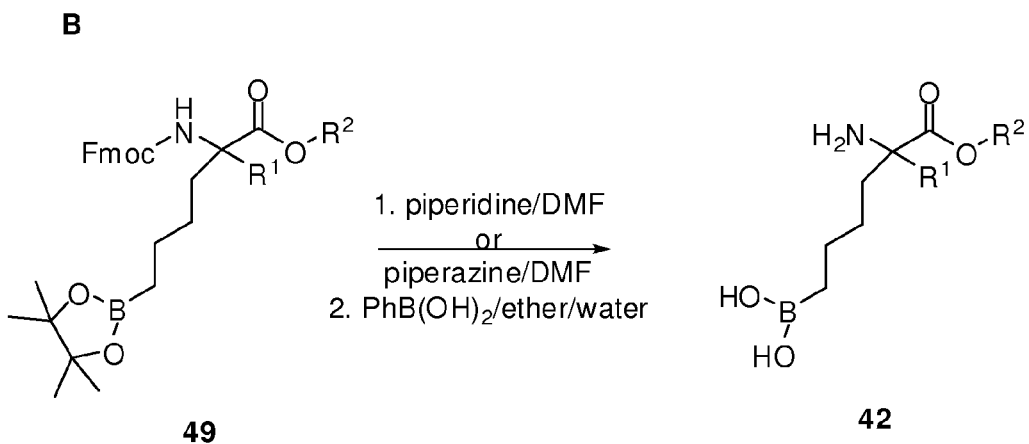

With the objective of improving the oral bioavailability of the compound 1 of this invention, various prodrug strategies could be pursued. In one embodiment, the α-carboxylic acid of 1 is converted to an ester. The ester is stable in the gastrointestinal tract, is optimally transported across the gastrointestinal lining into the bloodstream, and is then converted to the carboxylic acid moiety by the ubiquitous esterases in the blood or other tissues. FIGS. 13 and 14 illustrate selected methods to convert protected intermediates of 1 to various esters and then deprotect the α-amine and boronic acid to yield esters 42.

Compound 41 may be prepared from compound 35 (which is illustrated in FIGS. 8 and 10) by treatment with 50-100% TFA/DCM at room temperature for 1-6 hr. As illustrated in scheme A in FIG. 13, Compound 41 may subsequently be treated with an alcoholic HCl solution (using an alcohol such as but not limited to methanol), at elevated temperature for a few hours resulting in compound 42. Similar results may be obtained by treating 41 with thionyl chloride in an alcohol at reflux for 12-16 hr.

Compounds 43, 44, 45 and 46 may be prepared from compound 41 by reprotecting the amine with a reagent such as benzyl chloroformate or 9-fluorenyl chloroformate. Alternatively, these protecting groups could be introduced at an earlier stage of the synthesis as illustrated in FIG. 7 for the Cbz protection strategy. As illustrated in scheme B in FIG. 13, compounds 43-46 may be esterified by treatment with a halogenated reagent such as ethyl iodide under mildly basic condition in DMF or acetonitrile to yield the respective product 47-50. Alternatively, as illustrated in scheme C in FIG. 13, compounds 43-46 may be esterified by treatment with an alcohol in the presence of DCC to yield the respective product 47-50. Alternatively, as illustrated in scheme D in FIG. 13, compounds 43-46 may be esterified by treatment with oxalyl chloride and subsequence alcoholysis to yield the respective product 47-50.

As illustrated in scheme A in FIG. 14, compound 42 may be prepared by deprotecting compounds 47, 48, and 50 as outlined in FIG. 10. Alternatively, as illustrated in scheme B in FIG. 14, compound 42 may be prepared by deprotecting compound 49 in a two-step manner, first using piperazine or piperidine in DMF to remove the Fmoc group and then transesterifying the product with phenylboronic acid to remove the pinacol from the boronic acid. Compound 42 may be purified by reverse phase HPLC using gradients of acetonitrile/water.

Uses of the Compounds of the Invention

In a non-limiting aspect, the compounds of the invention have good arginase inhibitory potency at pHs lower than 9.5. In contrast, the prototypical boronic acid-type arginase inhibitor, ABH, shows a decrease in inhibitory potency for both arginases at pH 7.5 as compared to pH 9.5. This appears to be a common property of boronic acid-type inhibitors that do not contain a proximal nitrogen located at an appropriate distance on the side-chain-substituent on the α-carbon of the amino acid.

To illustrate the importance of the proximal nitrogen, compounds which do not have a proximal nitrogen, such as Comparative Example 1 (illustrated in Table 1), to compounds that have a proximal nitrogen such as Comparative Example 4. As illustrated in Table 2, Comparative Example 1 has lower potencies at pH 7.5 than at pH 9.5 for both arginase types, while Comparative Example 4 shows increased potency at human arginase I. It should be appreciated that Comparative Example 4 differs from Comparative Example 1 only in the replacement of the proximal nitrogen by a carbon atom. Likewise, a comparison of Example 8 and Comparative Example 2 (Table 1) and Example 11 and Comparative Example 3 (Table 1), which also differ only by the presence of a proximal nitrogen, show the same pH effect. In particular, the piperazines (Examples 8 and 11) containing the proximal nitrogen show increased potencies for at least one of the arginases at pH 7.5 as compared to pH 9.5, while the piperidines (Comparative Examples 2 and 3) show decreased potencies at pH 7.5 as compared to pH 9.5. Examples 17 and 28 are analogs that contain the proximal nitrogen while the distal nitrogen of the piperazine has been replaced by a carbon atom. Thus, the presence of a proximal nitrogen at a preferred distance on the side-chain-substituent on the α-carbon of the amino acid is associated with this "pH effect."

TABLE 1

Structures of Comparative Examples 1-3

| Comparative Example No. | Structure |
|---|---|
| 1 | 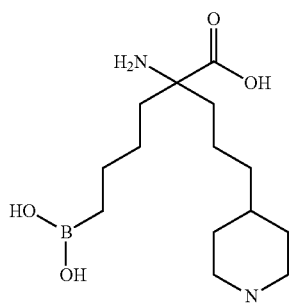 |
| 2 | 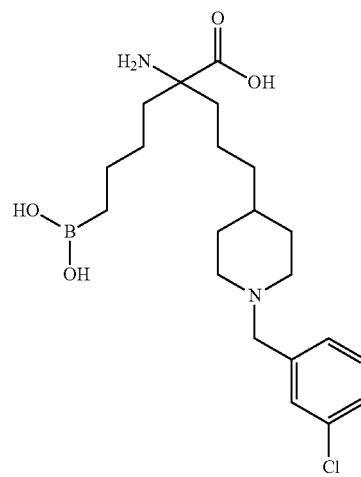 |
| 3 | 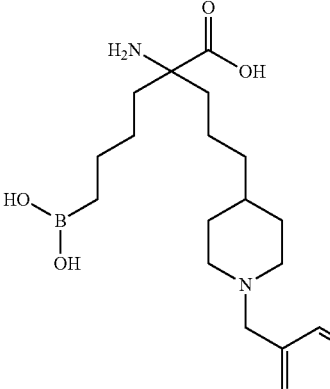 |

TABLE 2

SAR Data

| | human arginase I | | human arginase II | | increased potency for at least one |
| Example | pH 9.5 | pH 7.5 | pH 9.5 | pH 7.5 | isozyme |
|---|---|---|---|---|---|
| ABH | 2 | 3[b] | 2 | 4[b] | no[b] |
| Comparative Example 4 | 3 | 2[a] | 2 | 6[b] | yes[a] |

TABLE 2-continued

| | | | | | |
|---|---|---|---|---|---|
| Comparative Example 1 | 2 | 4[b] | 1 | 6[b] | no[b] |
| 8 | 2 | 1[a] | 2 | 2[a] | yes[a] |
| Comparative Example 2 | 2 | 4[b] | 2 | 4[b] | no[b] |
| 11 | 2 | 1[a] | 2 | 2[a] | yes[a] |
| Comparative Example 3 | 2 | 5[b] | 2 | 5[b] | no[b] |
| 17 | 2 | 1[a] | 2 | 4[b] | yes[a] |
| 28 | 1 | 1[a] | 1 | 3[b] | yes[a] |

Codes for Table 2:
[a] equal to or more potent at pH 7.5 than pH 9.5
[b] less potent at pH 7.5 than pH 9.5

| Ki values | Assigned value |
|---|---|
| <10 nM | 1 |
| 11-50 nM | 2 |
| 51-100 nM | 3 |
| 101-250 nM | 4 |
| 251-400 nM | 5 |
| >400 nM | 6 |

Table 3 illustrates piperazine-containing derivatives compared with the prototypical boronic acid-type arginase inhibitor ABH. The data presents therein illustrates the "pH effect" as a function of side-chain length. For example, Example 2 has a 2-carbon side-chain linker, Example 1 (Table 2) has a 3-carbon side-chain linker, and Example 93 has a 4-carbon linker side-chain linker. The 2-carbon side-chain linker benzyl piperazine, Example 15, may also be compared to the 3-carbon side-chain linker benzyl piperazine, Example 8 (Table 2). Even though the compounds demonstrate a "pH effect", it is apparent that the 3-carbon linker is optimal.

In Examples 20 and 21, the proximal nitrogen was constrained in a piperidine ring. Each of these compounds was found to be more active against arginine I over arginine II even at pH 7.5, indicating that both examples display some selectivity for arginase I over arginase II.

Examples 7, 9 and 10, all of which show the "pH effect", have differentially substituted benzyl groups on the distal nitrogen. Examples 16 and 41, which also exhibit the "pH effect," each have an aromatic substituent on the distal nitrogen. Additionally, Example 14, which exhibits the "pH effect," has a phenethyl group on the distal nitrogen, suggesting that aromatic groups may be placed at different distances from the distal nitrogen without suppressing the "pH effect."

Table 3 also lists piperazine derivative compounds are in which the distal nitrogen has been rendered neutral by acylation or sulfonylation. Example 129 has a benzamido group, Example 142 is a urea analog, and Example 151 has a sulfonamido group. Each compound showed the "pH effect" for human arginase I, with selectivity for arginase I over arginase II at lower pHs. Further analysis also showed that the acylated distal nitrogen does not need to be in the heterocyclic ring in order to allow for the "pH effect." Examples 31, 60, 112, 114 have an acylated nitrogen outside of the heterocyclic ring and these compounds possess the "pH effect" with high inhibition activity against one or both of the human arginases—note that the proximal nitrogen is still basic.

As discussed earlier, Example 28 (Table 2) suggests that the distal nitrogen can be replaced by a carbon atom. Additional analogs (Examples 26, 27, 31, 32, 34, 36, 37, 39, 40, 44, 46, 101, 102, 103, and 106 in Table 3), where the proximal nitrogen is contained in a piperidine ring, suggest that this piperidine ring can be substituted at a variety of positions with a variety of moieties and still possess the "pH effect" for either of the arginases.

The piperidine ring may be replaced by unsubstituted or substituted pyrrolidine or azetidine and still possess the "pH effect" as long as the basic nitrogen is in the proximal position as shown by the activity for Examples 50, 51, 54, 56, 57, 58, 60, 112, and 114.

The basic nitrogen may be contained in heterocyclic rings such as tetrahydroisoquinoline (Example 45), morpholine (Example 64), and benzimidazole (Example 116), where the proximal nitrogen would be expected to be less basic than when it is contained in a piperazine or piperidine ring.

Additionally, the proximal basic nitrogen does not need to be in a heterocyclic ring to possess this "pH effect." Examples 67, 68, 77, 78, 85, 86, 88, 90, 117, 120 correspond a variety of substituted secondary or tertiary amines with either alkyl or arylalkyl moieties.

This proximal basic nitrogen can also be part of an α-amino acid or α-amino ester as illustrated in Examples 98, 125 and 126. The activity of these examples is reduced at both pHs, but they still possess the "pH effect" with at least one of the arginases.

TABLE 3

Biological Testing Data.

| | human Arginase I | | human Arginase II | | increased potency for at least one isozyme |
|---|---|---|---|---|---|
| Example | pH 9.5 | pH 7.5 | pH 9.5 | pH 7.5 | |
| 2 | 4 | 4 | 4 | 6 | Y |
| 7 | 2 | 1 | 3 | 2 | Y |
| 9 | 3 | 1 | 2 | 2 | Y |
| 10 | 2 | 1 | 2 | 2 | Y |
| 14 | 2 | 1 | 2 | 1 | Y |
| 15 | 4 | 4 | 3 | 6 | Y |
| 16 | 3 | 2 | 2 | 3 | Y |
| 20 | 2 | 2 | 4 | 4 | Y |
| 21 | 2 | 2 | 3 | 3 | Y |
| 26 | 2 | 1 | 2 | 1 | Y |
| 27 | 2 | 1 | 2 | 1 | Y |
| 31 | 2 | 1 | 3 | 1 | Y |
| 32 | 1 | 2 | 3 | 1 | Y |
| 34 | 1 | 1 | 2 | 1 | Y |
| 36 | 1 | 1 | 2 | 1 | Y |
| 37 | 1 | 1 | 2 | 1 | Y |
| 39 | 1 | 1 | 2 | 1 | Y |
| 40 | 1 | 1 | 2 | 1 | Y |
| 41 | 2 | 1 | 2 | 1 | Y |
| 44 | 2 | 1 | 2 | 1 | Y |
| 45 | 2 | 1 | 2 | 1 | Y |
| 46 | 2 | 2 | 1 | 2 | Y |
| 50 | 2 | 2 | 2 | 2 | Y |
| 51 | 3 | 2 | 4 | 2 | Y |
| 54 | 2 | 2 | 3 | 2 | Y |
| 56 | 2 | 2 | 4 | 3 | Y |
| 57 | 2 | 1 | 3 | 2 | Y |
| 58 | 2 | 1 | 2 | 2 | Y |
| 60 | 1 | 1 | 2 | 1 | Y |
| 64 | 2 | 1 | 3 | 2 | Y |
| 65 | 3 | 2 | 6 | 2 | Y |
| 67 | 1 | 1 | 1 | 1 | Y |
| 68 | 2 | 2 | 2 | 2 | Y |
| 77 | 1 | 1 | 2 | 1 | Y |
| 78 | 2 | 2 | 2 | 3 | Y |
| 85 | 2 | 2 | 4 | 2 | Y |
| 86 | 1 | 1 | 2 | 2 | Y |
| 88 | 2 | 3 | 3 | 3 | Y |
| 89 | 1 | 1 | 2 | 1 | Y |
| 90 | 3 | 2 | 2 | 2 | Y |
| 93 | 2 | 2 | 2 | 6 | Y |
| 94 | 2 | 2 | 2 | 1 | Y |
| 95 | 1 | 3 | 1 | 2 | Y |
| 96 | 2 | 2 | 2 | 2 | Y |
| 98 | 4 | 6 | 6 | 6 | Y |
| 101 | 2 | 1 | 2 | 1 | Y |
| 102 | 2 | 1 | 2 | 1 | Y |

TABLE 3-continued

| | | | | | |
|---|---|---|---|---|---|
| 103 | 2 | 1 | 2 | 1 | Y |
| 106 | 2 | 2 | 5 | 2 | Y |
| 112 | 1 | 1 | 2 | 1 | Y |
| 114 | 2 | 1 | 2 | 1 | Y |
| 116 | 2 | 5 | 2 | 2 | Y |
| 117 | 2 | 2 | 2 | 3 | Y |
| 120 | 2 | 1 | 1 | 1 | Y |
| 125 | 4 | 4 | 5 | 4 | Y |
| 126 | 4 | 4 | 2 | 5 | Y |
| 129 | 3 | 2 | 3 | 5 | Y |
| Comparative Example 5 | 4 | 2 | 4 | 5 | Y |
| 142 | 2 | 2 | 2 | 3 | Y |
| 151 | 4 | 2 | 3 | 6 | Y |

| Ki values | Assigned value |
|---|---|
| <10 nM | 1 |
| 11-50 nM | 2 |
| 51-100 nM | 3 |
| 101-250 nM | 4 |
| 251-400 nM | 5 |
| >400 nM | 6 |

Without wishing to be bound by the theory, the SAR developed for this class of arginase inhibitors suggests that at least one additional interaction is made between $R^1$ side chain and the enzyme. X-ray crystal structures of the complexes with Example 8 and human arginase I and human arginase II have been solved. In these structures it was noted that the "ABH" portion of Example 8 binds in a similar fashion as reported for ABH itself. Specifically, the α-amine and α-carboxylic acid moieties fit into their respective pockets on the two enzymes in a well-defined hydrogen bonding and ion pairing array as observed for these moieties in ABH. Additionally, the boronic acid of Example 8 was bound with the catalytic water molecule in a very similar fashion as ABH was observed to have. The proximal basic nitrogen, which is separated by three carbons from the α-carbon of Example 8, was observed to ion pair with aspartic acid side chains near the active site. Most notably, the side chains of Asp181 and 183 in human arginase I were in close contact with this basic nitrogen. We hypothesize that this basic nitrogen would be mostly ionized to form a positively charged species at pH 7.5, whereas at pH 9.5 this atom would mostly be un-ionized; thus, the ion pairing with the negatively charged carboxylic acids of these aspartates would be minimized at the latter pH value. Some ligands tested, such as Examples 98 and 116, are expected to have lower pKa values for the proximal N and are not as active as examples with proximal nitrogens with higher pKa values.

As described above, Examples 2 and 93 (ethyl and butyl spacers for proximal nitrogen) have lowered inhibition compared to Example 1. The ion pairing interaction observed in Example 8 would be expected to be less significant in these examples since the proximal basic nitrogen is not optimally placed.

In a non-limiting aspect, the pH insensitivity demonstrated by these amino acids makes them particularly useful as arginase inhibitors.

Pharmaceutical Compositions of the Invention

In one embodiment, the invention is directed to a composition comprising at least one compound of the invention or a pharmaceutically acceptable salt thereof; and a pharmaceutically-acceptable carrier.

In another embodiment, the invention is directed to a pharmaceutical composition comprising at least one compound of the invention or pharmaceutically acceptable salt thereof; and at least one pharmaceutically acceptable carrier.

In one embodiment, the compound or pharmaceutically acceptable salt thereof is present in an effective amount in the composition. In another embodiment, the compound or a pharmaceutically acceptable salt thereof is present at a level of from about 0.1% by weight to about 90% by weight, based on the total weight of the pharmaceutical composition. Preferably, the compound or a pharmaceutically acceptable salt thereof is present at a level of at least about 1% by weight, based on the total weight of the pharmaceutical composition. More preferably, the compound or a pharmaceutically acceptable salt thereof is present at a level of at least about 5% by weight, based on the total weight of the pharmaceutical composition. Even more preferably, the compound or a pharmaceutically acceptable salt thereof is present at a level of at least about 10% by weight, based on the total weight of the pharmaceutical composition. Yet even more preferably, the compound or a pharmaceutically acceptable salt thereof is present at a level of at least about 25% by weight, based on the total weight of the pharmaceutical composition.

The invention includes combination formulations, which include formulations comprising at least one compound of the invention and a second therapeutic agent, wherein the at least one compound of the invention and the second therapeutic agent are co-formulated. The invention also includes combination therapies, which include co-administration of an arginase inhibitor hereof with another pharmaceutically active compound or medication. More particularly, the term "combination therapy" refers to the administration of two or more therapeutic agents or compounds to treat at least one therapeutic condition or disorder described in the present disclosure. Such administration includes use of each type of therapeutic agent in a concurrent or simultaneous manner. Such administration includes the use of each type of therapeutic agent in the same unit dosage form or in separate unit dosage forms. In either case, the treatment regimen provides beneficial effects of the drug combination in treating the conditions or disorders described herein.

Accordingly, in certain embodiments, the invention is directed to compositions comprising a compound of the invention or a pharmaceutically acceptable salt thereof; and an inhibitor selected from the group consisting of a phosphodiesterase-1 (PDE1) inhibitor, a phosphodiesterase-2 (PDE2) inhibitor, a phosphodiesterase-3 (PDE3) inhibitor, a phosphodiesterase-4 (PDE4) inhibitor, a phosphodiesterase-5 (PDE5) inhibitor, a non-specific PDE inhibitor that inhibits at least two enzymes selected from the group consisting of PDE1, PDE2, PDE3, PDE4 and PDE5, and a combination thereof; and an optional pharmaceutically-acceptable excipient.

In one embodiment, the compounds of the invention are useful in the treatment of patients who do not respond to PDE5 inhibitors. Without wishing to be bound by the theory, arginase inhibitors are effective in the treatment of patients that do not respond to PDE5 inhibitors because arginase operates at an earlier stage in the pathway leading to NO-dependent relaxation of genital smooth muscle tissue required for sexual arousal.

Non-limiting suitable phosphodiesterase-1 (PDE1) inhibitors include SE3623 (available from Eisai), BAY 38304S (available from Bayer), HFV 1017 (7-benzenesulfonylamino-3a-ethyl-1,2,3,3a,10,11b-hexahydro-11H-5a,11a-diaza-benzo[cd]fluoranthene-S-carboxylic acid ethyl ester 2,3-dihydroxy-succinate available from Oaiichi Fine Chemical), KF 19S14 (5-phenyl-3-(3-pyridyl)-methyl-3H-imidazo[4,5-c][1,8]naphthyridin-4(5H)-one available from Kyowa Hakko) and SCH 51866 ((cis-5,6a,7,8,9,9a-hexahydro-2-[4-(trifluoromethyl)phenylmethyl]-5-methyl-cyclopent[4,5]imidazo[2,1-b]purin-4(3H)-one) available from Schering-Plough).

Non-limiting suitable phosphodiesterase-2 (PDE2) inhibitors include BAY 607550 (2-(3,4-dimethoxy-benzyl)-7-[1-(1-hydroxy-ethyl)-4-phenyl-butyl]-5-methyl-3H-imidazo[5,1-f][1,2,4]triazin-4-one available from Bayer).

Non-limiting suitable phosphodiesterase-5 (PDE5) inhibitors include sildenafil (sold under the tradename Viagra™), vardenafil (sold under the tradename Levitra™), tadalafil (sold under the tradename Cialis™), mirodenafil, udenafil, avanafil, dasantafil, NM 702 (4-bromo-6-[3-(4-chloro-phenyl)-propoxy]-5-[(pyridin-3-ylmethyl-amino]-2H-pyridazin-3-one hydrochloride available from Nissan Chemical Industries), SLx-2101 (available from Surface Logix) and UK 369003 (available from Pfizer).

Non-limiting suitable non-specific PDE inhibitors that inhibit at least two enzymes selected from the group consisting of PDE 1, PDE2, PDE3, PDE4 and PDE5, or a combination thereof include amlexanox, caffeine citrate, doxofylline, levosimendan, mopidamol, pentoxifylline, pemobendan, propentofylline, vesnarinone, and ibudilast.

Such compositions are prepared in accordance with acceptable pharmaceutical procedures, such as described in Remington's Pharmaceutical Sciences, 17th edition, ed. Alfonoso R. Gennaro, Mack Publishing Company, Easton, Pa. (1985). Pharmaceutically acceptable carders are those that are compatible with the other ingredients in the formulation and biologically acceptable.

In certain embodiments, compounds of the invention may be administered orally or parenterally, neat or in combination with conventional pharmaceutical carriers. Applicable solid carriers may include one or more substances that may also act as flavoring agents, lubricants, solubilizers, suspending agents, fillers, glidants, compression aids, binders or tablet disintegrating agents or an encapsulating material. In powders, the carrier is a finely divided solid in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Liquid carriers may be used in preparing solutions, suspensions, emulsions, syrups, and elixirs. The active ingredient of this invention may be dissolved or suspended in a pharmaceutically acceptable liquid carrier such as water, an organic solvent, a mixture of both or pharmaceutically acceptable oils or fat. The liquid carrier may contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier may also be an oily ester such as ethyl oleate and isopropyl myristate. Sterile liquid carriers are used in sterile liquid form compositions for parenteral administration.

Liquid pharmaceutical compositions, which are sterile solutions or suspensions, may be administered by, for example, intramuscular, intraperitoneal, or subcutaneous injection. Sterile solutions may also be administered intravenously. Oral administration may be either liquid or solid composition form.

Preferably, the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form may be, for example, a capsule or tablet itself, or it may be the appropriate number of any such compositions in package form.

In another embodiment of the present invention, the compounds useful in the present invention may be co-administered to a mammal with one or more other pharmaceutical active agents, such as those agents being used to treat any other medical condition present in the mammal. Examples of such pharmaceutical active agents useful for such combination therapies include pain relieving agents, anti-angiogenic agents, anti-neoplastic agents, anti-diabetic agents, anti-infective agents, gastrointestinal agents, or combinations thereof.

The one or more other pharmaceutical active agents may be administered in a therapeutically effective amount simultaneously (such as individually at the same time, or together in a pharmaceutical composition), or successively with one or more compounds of the invention.

The route of administration may be any route, such as oral, nasal, pulmonary, transdermal, such as passive or iontophoretic delivery, or parenteral, e.g., rectal, depot, subcutaneous, intravenous, intraurethral, intramuscular, intranasal, ophthalmic solution or an ointment, that effectively transports the active compound of the invention to the appropriate or desired site of action. Furthermore, the administration of compound of invention with other active ingredients may be concurrent or simultaneous.

In one embodiment, a formulation of the invention is administered to a mammal via at least one route selected from the group consisting of oral, nasal, pulmonary, transdermal, intranasal, ophthalmological, rectal, and parenteral, wherein said parenteral administration comprises subcutaneous, intravenous, intraurethral, or intramuscular.

It is especially advantageous to formulate the compositions in dosage unit form for ease of administration and uniformity of dosage. Dosage unit form, as used herein, refers to physically discrete units suited as unitary dosages for the patient to be treated; each unit containing a predetermined quantity of the peptide calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of the patients.

The pharmaceutical compositions can be included in a container, pack, or dispenser together with instructions for administration.

Typically, dosages of the compounds of the invention that may be administered to an animal, preferably a human, range in amount from 1 microgram to about 100 milligrams per kilogram of body weight of the animal. The precise dosage administered varies depending upon any number of factors, including but not limited to, the type of animal and type of disorder being treated, the age of the animal and the route of administration. Preferably, the dosage of the compound varies from about 10 micrograms to about 10 milligrams per kilogram of body weight of the animal. More preferably, the dosage varies from about 100 micrograms to about 5 milligrams per kilogram of body weight of the animal.

Typically, the compounds of the invention may be administered to an animal as frequently as several times daily, or it may be administered less frequently, such as once a day, once a week, once every two weeks, once a month, or even less frequently, such as once every several months or even once a year or less. The frequency of the doses is readily apparent to the skilled artisan and depends upon any number of factors, such as but not limited to, the type and severity of the disorder being treated, the type and age of the animal.

Diagnostic Uses of Compounds of the Invention

Diagnostic medical imaging is a critical element of modern health care. Ultrasound, radionuclide, X-ray, and magnetic resonance imaging techniques facilitate the diagnosis of disease. Diagnostic pharmaceuticals, frequently called contrast agents, may be administered to a patient in place of therapeutic arginase inhibitors, or they may be simultaneously administered with a therapeutic agent to a patient to augment the usefulness of the imaging technique itself. Such imaging agents act by altering the energy or the way that energy interacts with tissues. Diagnostic medical imaging frequently uses targeted contrast agents that, in binding or localizing at sites selectively within the body, help to resolve an image of diagnostic interest.

Targeted diagnostic imaging contrast agents generally consist of a targeting moiety labeled with a traceable imaging moiety. Such traceable imaging moieties include fluorescent tags; radio-opaque dyes (e.g., iodinated aromatics), radioactive elements such as $^3$H, $^{18}$F, $^{125}$I, $^{129}$I; or diagnostically useful chelated radioactive or paramagnetic metals such as Gd(III), Mn(II), Tc-99m, Re-186, Re-188, In-111 or Ga-67. Examples of useful diagnostic imaging agents of the invention include compounds in which at least one hydrogen atom of the first and/or second substituents has been substituted with one of the foregoing imaging moieties.

The targeting moiety carries the label to the site of diagnostic interest where it is detected. e.g. by MRI, US, CT, or radionuclide imaging (including SPECT and PET). In certain preferred embodiments of compounds of the invention, the compound of the invention has a residue of an imageable moiety selected from the group consisting of a gamma ray emitting radioisotope, a positron emitting radioisotope, a magnetic resonance imaging contrast agent, an X-ray contrast agent, and an ultrasound contrast agent.

By using such an arginase inhibitor suitable conjugated to an imageable moiety, endogenous arginase activity may be visually observed in a patient's body in real time. In order to be effective, the imageable moiety should not significantly interfere with the binding of the derivatized arginase inhibitor to its substrate. For example, the arginase-inhibitor imageable-moiety conjugate may have a $K_i$ or less than about 1000 nM.

The invention includes a derivatized compound labeled with a fluorescent label. The invention also includes a derivatized arginase inhibitor labeled with a fluorescent label. For example, in an embodiment, a spectroscopic probe, such as a fluorescent moiety or an NMR or MRI sensitive moiety or complex is covalently attached as a substituent group through a flexible linker sufficiently long so that the probe does not make unfavorable interactions with the protein surface. Such spectroscopic probe is a useful diagnostic tool for noninvasive determination of arginase overexpression, as observed in certain disease states, such as, for example, asthma (over expression of airway arginase), cancer (overexpression of arginase in certain breast cancers, colon cancers, and the like), or certain internal bacterial infections (e.g., *H. pylori* overexpresses bacterial arginase in order to evade the immune response in human stomach ulcers).

In one aspect, the invention includes a method of diagnosing arginase overexpression in a patient, comprising the steps of administering to the patient a diagnostically-effective amount of a compound of the invention or a pharmaceutically acceptable salt thereof; where the compound comprises a second substituent, wherein the second substituent allows for in vivo imaging of the compound; and imaging the patient.

In one embodiment, the arginase overexpression is associated with asthma, cancer, bacterial infections, or combinations thereof.

In another aspect, the invention includes a method of diagnosing arginase overexpression in a patient, comprising administering to said patient a diagnostically-effective amount of a compound of the invention or a pharmaceutically acceptable salt thereof; wherein the compound comprises an imageable moiety; and imaging said patient.

In one embodiment, the arginase overexpression is associated with asthma, cancer, bacterial infections, or combinations thereof.

In yet another aspect, the invention is directed to a method for radioimaging a patient, comprising administering to the patient an effective amount of a compound of the invention, wherein the compound has an radioimageable moiety; and scanning the patient using a radioimaging device.

In yet another aspect, the invention includes a method of inhibiting arginase, comprising contacting the arginase with a compound of the invention or a salt thereof.

In one embodiment, the arginase is yeast, bacterial, parasitic, or mammalian. In another embodiment, the mammalian arginase is a human type I arginase or a human type II arginase (e.g., human penile arginase).

In yet another aspect, the invention includes a diagnostic composition, comprising a diagnostically-effective amount of the compound of the invention or a pharmaceutically acceptable salt thereof; and a pharmaceutically acceptable carrier; where the compound is labeled with a diagnostic label.

In yet another aspect, the invention includes a diagnostic composition, comprising a diagnostically-effective amount of the compound of the invention or a pharmaceutically acceptable salt thereof; and a pharmaceutically acceptable carrier; where the compound is labeled with an imageable moiety.

Therapeutic Uses of Compounds of the Invention

The invention includes compounds that inhibit the enzymatic activity of arginase. These compounds, which were not previously known to inhibit this enzyme (and not previously known to have any use), are useful for a variety of applications in medicine and research.

The compounds, compositions, and methods of the invention are useful for inhibiting the activity of arginase including, but not limited to, mammalian (e.g., human), yeast, and bacteria (such as *H. pylori*) arginase. The compounds, compositions, and methods described herein may be used to inhibit arginase activity in vitro or in vivo, for example, in a human. These compositions may also be used to treat a disorder characterized either by abnormally high arginase activity in a tissue of a mammal or by abnormally low nitric oxide synthase activity in a tissue of the mammal, preferably a human, "Inhibition" of arginase by an arginase inhibitor, as used herein, means reduction in the level of arginase activity in the presence of the inhibitor, compared with the level of arginase activity in the absence of the inhibitor.

To alleviate an arginase-related disorder in a mammal, an arginine inhibitor described herein is administered to a mammal afflicted with the disorder. The inhibitor is preferably administered in combination with one or more pharmaceutically acceptable carriers, as described in further detail herein. The inhibitor (preferably in combination with a carrier) can also be administered to a mammal afflicted with a disorder characterized by aberrant NO synthase activity, or to one which exhibits normal (i.e. non-diseased) levels of arginase and NO synthase activities, but in which inhibition of arginase activity is desired.

There are several arginase-linked diseases, some of which are listed below. They are linked with the one, two, or all of the three phenomena related to constitutive or upregulated arginase activity described elsewhere herein. Many of these diseases are characterized by two or even three of the phenomena simultaneously or sequentially, e.g., cellular proliferation and accumulation of fibrotic tissue can stiffen airway or vascular tissue in a constricted state so that it is more difficult to achieve NO-dependent relaxation.

The compounds of the invention may be used to treat conditions or diseases of mammal. In one embodiment, the diseases or disorders are associated with abnormally high level of arginase activity or abnormally low level of NO synthase activity. An "abnormally high level of arginase activity," as used herein, means a level of arginase activity that exceeds the level found in normal tissue when the normal tissue does not exhibit an arginase related disorder phenotype. An "abnormally low level of NO level," as used herein, means a level of NO which is lower than that found in normal tissue.

In one embodiment, the compounds disclosed herein may be used in the treatment, prevention, management, or diagnosis of one or more of the following diseases, conditions, or maladies: conditions associated with ischemia reperfusion injury (myocardial ischemia-reperfusion injury, organ transplantation, acute renal failure, vaso-occlusive crises in sickle cell disease), idiopathic pulmonary fibrosis, pulmonary arterial hypertension, acute coronary vasodilation, asthma, acute respiratory distress syndrome, chronic obstructive pulmonary disease (COPD), bronchopulmonary dysplasia, hypoxic respiratory failure, cystic fibrosis, subarachnoid hemorrhage, thrombosis, microbial infections, cancer, wound healing, blood preservation, cardiac hypertrophy, gastrointestinal disease, pulmonary inflammatory disease, sexual arousal disorder, cardiovascular disorder, disease caused by a pathogenic microorganism, immunological disorder, cancer, pre-term labor, Reynaud's disease, psoriasis, rheumatoid arthritis, and Peyronie's Disease.

In one embodiment, the compounds disclosed herein may be used in the treatment, prevention, management, or diagnosis of one or more of the following diseases, conditions, or maladies, each of which is discussed individually below: (1) gastrointestinal diseases, (2) pulmonary inflammatory diseases, (3) sexual arousal disorders, (4) cardiovascular disorders, (5) diseases caused by a pathogenic microorganisms, (6) immunological disorders, (7) cancer, (8) pre-term labor, (9) Reynaud's disease, (10) psoriasis, (II) rheumatoid arthritis, and (12) Peyronie's Disease, among others.

1. Gastrointestinal Diseases

An increase in arginase activity has been associated with the pathophysiology of a number of conditions including impairment in non-adrenergic and non-cholinergic (NANC) nerve-mediated relaxation of gastrointestinal smooth muscle. An arginase inhibitor may be used to alleviate such impairment by administering the inhibitor to a mammal experiencing such impairment or a mammal which is anticipated to experience such impairment (e.g., a human afflicted with a gastrointestinal motility disorder).

Accordingly, the compounds of the invention may be useful in the treatment or prevention of gastrointestinal motility disorders, which is based on the observation that arginase is present in opossum internal anal sphincter muscle and the known arginase inhibitor, ABH, has been shown to relax this muscle. See, e.g., Baggio et al., 1999, J. Pharm. Exp. Then 290, 1409-16.

The compounds of the invention may also be useful in the treatment or prevention of inflammatory bowel disease (e.g., Crohn's disease and ulcerative colitis). In fact, IBD has been shown to be characterized by increased arginase activity and endothelial dysfunction. See, e.g., Horowitz et al., 2007, Am. J. Physiol. Gastrointest. Liver Physiol. 292, G 1323-36.

Likewise, the compounds of the invention may be useful in the treatment or prevention of gastric ulcers, because the bacterium that causes stomach ulcers, *Helicobacter pylori*, exhibits increased arginase activity upon colonization in order to evade the human immune response. See, e.g., Gobeli et al., 2001, Proc. Natl. Acad. Sci, (USA) 98,13844-49.

2. Pulmonary Inflammatory Diseases

The compounds of the invention may be useful in the treatment or prevention of asthma based on the observation that arginase is upregulated in the asthmatic airway. See, e.g., Zimmermann and Rothenberg, 2006, Eur. J. Pharmacol. 533: 253-62. Furthermore, nebulizer treatment of guinea pigs with ABH in an allergic asthma model prevents airway hyperresponsiveness. See, e.g., Maarsingh, "Arginase: A Novel Key Enzyme in the Pathophysiology of Allergic Asthma," Ph.D. dissertation, Chapter 9, University of Groningen, Netherlands (2006); Maarsingh et al., 2008, Am. J. Respir. Crit. Care Med. 178:565-73. The asthma phenotype is characterized by airway constriction, airway smooth muscle hyperplasia, and the chronic accumulation of fibrotic tissue; an arginase inhibitor can relax airway smooth muscle and attenuate cellular hyperplasia and fibrosis.

Additionally, the compounds of the invention may be useful in the treatment or prevention of chemically-induced lung fibrosis because arginase I and II are induced in bleomycin-induced lung fibrosis in order to provide more L-ornithine for collagen biosynthesis. See, e.g., Endo et al., 2003, Am. J. Physiol. Lung Cell Mol. Physiol. 285, L313-21.

The compounds of the invention may also be useful in the treatment or prevention of idiopathic pulmonary fibrosis, based on the observation that virus-induced upregulation of arginase I is observed in an animal model. See, e.g., Mora et al., 2006, Am. J. Respir. Cell Mal. Biol. 35:466-73.

Furthermore, the compounds of the invention may be useful in the treatment or prevention of cystic fibrosis. Increased sputum arginase activity contributes to NO deficiency in cystic fibrosis lung disease; arginase activity also contributes to fibrosis. See, e.g., Graseman et al., 2005, Am. J. Respir. Crit. Care Med. 172:1523-28

3. Sexual Arousal Disorders

Erectile dysfunction afflicts one-half of the male population over the age of forty. This malady often results from defects in the complex cascade of enzyme-catalyzed reactions governing blood flow into and out of the corpus cavernosum, a chamber of muscular, spongy tissue that becomes engorged with blood in the erect penis. Defects that compromise cavernosal blood flow often occur as secondary complications related to other health conditions, such as heart disease, hypertension, diabetes, use of certain medications, and the like.

In an important embodiment, the invention relates to use of an arginase inhibitor described herein for enhancing penile erectile function in a mammal (preferably a male human) or for alleviating erectile dysfunction in a mammal. NO is an important regulator of erectile function and mediates NANC neurotransmission in penile corpus cavernosum smooth muscle, leading to rapid relaxation, which in turn leads to erection. NO synthase, which catalyzes oxidation of L-arginine to form L-citrulline and NO, is for this reason a key enzyme in penile smooth muscle physiology. Arginase catalyzes hydrolysis of L-arginine to form L-ornithine and urea. Arginase regulates NO synthase activity by affecting the amount of L-arginine available for oxidation catalyzed by NO synthase activity. Thus, inhibition of arginase activity can enhance NO synthase activity, thereby enhancing NO-dependent smooth muscle relaxation in the corpus cavernosum and enhancing penile erection.

Arginase is present in rabbit and human penile corpus cavernosum and ABH enhances the NO-dependent relaxation of this tissue. See, e.g., Cox et al., 1999, Nature Struct. Biol. 6:1043-47. The arginase inhibitor, ABH, enhances the erectile response in live male rabbits. See, e.g., Cama et al., 2003, Biochemistry 42; 8445-51. Arginase II is upregulated in the corpus cavernosum of the diabetic man, resulting in reduced NO biosynthesis which, in turn, leads to erectile dysfunction; administration of ABH in ex vivo experiments restores NO biosynthesis. See, e.g., Bivalacqua et al., 2001, Biochem. Biophys. Res. Commun. 283:923-27. Arginase I is upregulated in the penis of aged mice and impairs erectile function. See, e.g., Bivalacqua et al., 2007, Am. J. Physiol. Heart Circ. Physiol. 292:H1340-51.

The compounds of the invention may also be useful in the treatment or prevention of female sexual arousal disorder. The arginase inhibitor, ABH, enhances the engorgement response in the genitalia of female rabbits. See, e.g., Cama et al., 2003, Biochemistry 42:8445-51.

4. Cardiovascular Disorders

The compounds of the invention may be useful in the treatment or prevention of endothelial vascular dysfunction in atherosclerosis, hypertension, hypercholesterolemia, and diabetes. Arginase modulates NOS activity by regulation of L-arginine availability, and the deleterious effects of arginase can be blocked by an arginase inhibitor. See, e.g., Berkowitz et al., 2003, Circulation 108:2000-06 (2003); Yang and Ming, 2006, Um Med. Res. 4:53-65. Increased arginase activity in diabetes contributes to vascular endothelial dysfunction by decreasing L-arginine availability to NO synthase. See, e.g., Romero et al., 2008, Circ. Res. 102:95-102. Arginase inhibition attenuates hypertension in spontaneously hypertensive rats. See, e.g., Bagnost et al., 2010, Cardiovasc. Res. 87:569-577. Arginase inhibition has been demonstrated to mediate cardioprotection during ischemia-reperfusion. See, e.g., Jung et al., 2010, Cardiovasc. Res. 85:147-154. Other vascular conditions include peripheral vascular disease (PVD), peripheral arterial disease (PAD), and subarachnoid hemorrhage. Arginase has been identified as a new drug target for the treatment of atherosclerosis. See, e.g., Yang and Ming, 2006, Curr. Hypertension Rep, 8:54-59.

The compounds of the invention may be useful in the treatment or prevention of pulmonary arterial hypertension. Elevated arginase activity contributes to vascular endothelial dysfunction by compromising L-arginine availability to NO synthase. See, e.g., Morris et al., 2007, Adv. Pulmonary Hypertension 5:31-36. Arginase II has also been shown to be upregulated in the arteries of women with pre-eclampsia, a condition with increased hypertension. See Sankaralingam et al., 2010, Cardiovasc. Res. 85:194-201.

5. Diseases Caused by Pathogenic Microorganisms

The compounds of the invention may be useful in the treatment or prevention of African sleeping sickness, Chagas' disease, leishmaniasis, malaria, and other diseases caused by pathogenic microorganisms. Polyamine biosynthetic enzymes are essential for growth and survival of protozoa. See, e.g., Heby et al., 2003, Biochem. Soc. Trans. 31:415-19. Arginase is essential for viability. See, e.g., Roberts et al., 2004, J. Biol. Chem. 279:23668-78. Therefore, inhibitors of protozoan arginases can kill the protozoa.

Arginase can be inhibited in yeast by contacting the yeast with the composition of the invention. Inhibition of arginase in yeast serves to minimize urea production during fermentation of alcoholic beverages.

6. Immunological Disorders

The compounds of the invention may be useful in the treatment or prevention of multiple sclerosis, and possibly other autoimmune diseases, based upon the observation that arginase I is upregulated in an animal model of multiple sclerosis (experimental autoimmune encephalomyelitis) and administration of the arginase inhibitor ABH improves the disease score of animals. See, e.g., Xu et al., 2003, Immunology 110:141-48.

7. Cancer

Tumor-induced tolerance impairs the therapeutic efficacy of immunotherapy; one mechanism leading to T-cell tolerance is the generation of myeloid-derived suppressor cells (MDSCs), which produce arginase, thereby depleting the tumor microenvironment of L-arginine, which impairs T-cell signal transduction and function. T-cell anergy results. Notably, arginase activity is a mechanism of immune system evasion that is also shared by certain bacteria, e.g., *Helicobacter pylori*. MDSCs are regarded as "cancer's bulwark against immune attack." See, e.g., Marx, 2008, Science 319:154-56.

Accordingly, arginase is upregulated in the following types of cancers, which may be treated with an arginase inhibitor described herein: Renal cell carcinoma (see, e.g., Zea et al., 2005, Cancer Res. 65:3044-48; Ochoa et al., 2007, Clin. Cancer Res. 13:721s-726s); prostate cancer (see, e.g., Bronte et al., 2005, J. Exp. Med. 201:1257-68) (arginase inhibition with N-hydroxy-L-arginine facilitates tumor immunotherapy); colorectal cancer (see, e.g., Len and Wang, 1992, Cancer 70:733-36; Bronte and Zanovello, 2005, Nature Rev. Immunol. 5:641-54); breast cancer (see, e.g., Singh et al., 2000, Cancer Res. 60:3305-12; Bronte and Zanovello, 2005, Nature Rev. Immunol. 5:641-54) (the arginase inhibitor N-hydroxy-L-arginine inhibits cell proliferation and induces apoptosis); skin cancer (squamous cell and basal cell cancers) (see, e.g., Gokmen et al., 2001, J. Lab. Clin. Med. 137:340-44; Bronte and Zanovello, 2005, Nature Rev. Immunol. 5:641-54); lung cancer (see, e.g., Rodriguez et al., 2005, J. Exp. Med. 202:931-39; Bronte and Zanovello, 2005, Nature Rev. Immunol. 5:641-54); ovarian cancer (see, e.g., Melichar et al., J. Translational Med. 1, 1-5 (2003) (doi: 10.11861479-5876-1-5); and gastric cancer (see, e.g., Wu et al., 1992, Life Sci. 51, 1355-61); among others.

8. Management of Pre-Term Labor

Enhancement of uterine smooth muscle relaxation with an arginase inhibitor may be useful in the management of pre-term labor.

9. Reynaud's Disease

Reynaud's disease is a disease of the microvasculature. Because subcutaneous administration of the arginase inhibitor BEC (which is an analogue of ABH) in humans is vasodilatory and enhances circulation, an arginase inhibitor may be useful in treating Reynaud's disease. See, e.g., Holowatz et al., 2006, J. Physiol. 574:573-81.

10. Psoriasis

Arginase I is highly overexpressed in the hyperproliferative psoriatic epidermis in human skin, and therefore arginase inhibitors may be useful in the treatment of psoriasis. See, e.g., Bruch-Gerharz et al., 2003, Am. J. Pathology 162:203-11.

11. Rheumatoid Arthritis

Arginase II is upregulated in synovial fluid from human patients, and therefore arginase inhibitors may be useful in the treatment of arthritis. See, e.g., Huang & Kaohsiung, 2001, J. Med. Sci. 17:358-63; Corraliza and Moncada, 2002, J. Rheumatol. 29:2261-65.

12. Peyronie's Disease

The compounds of the invention may be useful in the treatment or prevention of Peyronie's disease. Arginase II is upregulated in the rat penis in an animal model for this disease. See, e.g., Bivalacqua et al., 2001, J. Andrology 22:497-506. While this disorder can contribute to erectile dysfunction, it is principally an inflammatory condition in which fibrotic tissue builds up in the penis.

13. General

The composition of the invention can be used to treat a disorder in a mammal, wherein the disorder is associated with expression of an abnormally high level of arginase activity in a tissue of the mammal. Because NO synthase activity is regulated in a reciprocal fashion with respect to arginase activity in mammals, more particularly humans, the compounds and compositions of the invention can be used to treat a disorder in a mammal, wherein the disorder is associated with expression of an abnormally low level of NO synthase activity in a tissue of the mammal. Since the reciprocal interaction of arginase and NO synthase has implications for the function of smooth muscle, the use of the compounds described herein for the regulation of smooth muscle activity in an animal is also contemplated in the invention. A compound of the invention or a composition comprising the compound of the invention which comprises an arginase inhibitor described herein can also be used to inhibit arginase in a mammal having normal levels of arginase and NO synthase activity, particularly where the physiology which is desired to be effected is one which is affected by arginase or NO synthase activity, or where a disorder which is not caused by aberrant arginase or NO levels can nonetheless be alleviated or inhibited by inhibiting arginase activity (e.g., certain forms of erectile dysfunction).

The invention includes methods of inhibiting arginase in a mammal, comprising administering to the mammal an effective amount of a compound of the invention or a pharmaceutically acceptable salt thereof.

The invention further includes methods of treating an arginase-related disorder in a mammal, comprising administering to the mammal an effective amount of a compound of the invention or a pharmaceutically acceptable salt thereof. In another embodiment, the arginase-related disorder is a disorder associated with an abnormally low level of nitric oxide synthase activity in a tissue of the human, a disorder associated with an abnormally high level of arginase activity in a tissue of the human, or combinations thereof, including heart disease, systemic hypertension, pulmonary hypertension, erectile dysfunction, autoimmune encephalomyelitis, chronic renal failure, gastrointestinal motility disorders, gastric cancers, reduced hepatic blood flow, insufficient hepatic blood flow, cerebral vasospasm, or a combination thereof.

The invention also includes methods of providing relief from immune suppression in a mammal, comprising administering to the mammal an effective amount of a compound of the invention or a pharmaceutically acceptable salt thereof; wherein said mammal is suffering from a disease or condition selected from the group consisting of a chronic infectious disease, a bacterial infection, a parasitic infection, trauma, leprosy, tuberculosis, liver transplantation, a cancer, and combinations thereof.

The invention further includes methods of inhibiting the production of ornithine in a mammal suffering from at least one tumor, comprising administering to the mammal an effective amount of a compound of the invention or a pharmaceutically acceptable salt thereof.

The invention also includes methods of enhancing smooth muscle relaxation or relaxing smooth muscle comprising contacting the smooth muscle with an arginase inhibitor. The smooth muscle is preferably within the body of an animal. The invention further includes methods of relaxing smooth muscle in a mammal, comprising administering to the mammal an effective amount of a compound of the invention or a pharmaceutically acceptable salt thereof. The type of smooth muscle to be relaxed includes, but is not limited to, gastrointestinal smooth muscle, anal sphincter smooth muscle, esophageal sphincter muscle, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle. When the smooth muscle is gastrointestinal smooth muscle, the type of gastrointestinal smooth muscle includes, but is not limited to, the internal anal sphincter muscle.

When the smooth muscle in within the body of the animal, the invention includes a method of alleviating (e.g., reducing the incidence or severity) or inhibiting (e.g., reducing the likelihood of developing, or preventing) an arginase-related disorder in an animal. In a preferred embodiment, the animal is a human.

The invention also contemplates use of an arginase inhibitor in an in vitro arginase inhibition/smooth muscle relaxation functional assay, for the purpose of identifying compounds which affect smooth muscle function. Compounds so identified are considered to be candidate arginase inhibitor antagonists, in that these compounds are identified by their ability to counteract the inhibition of arginase activity. For example, these compounds may be identified by using an assay for smooth muscle activity using the internal anal sphincter muscle and one on the arginase inhibitors of the invention. In this assay, strips of the internal anal sphincter muscle obtained from a mammal (e.g., an adult opossum) are induced to relax by NANC nerve-mediated relaxation using electrical field stimulation (EFS); relaxation is reversed by contacting the muscle strips with arginase; and reversal of relaxation is accomplished by contacting the muscle with an arginase inhibitor. The effect of the test compound on subsequent reversal of muscle relaxation is assessed. Any significant reversal of the relaxation state of the muscle in the presence of the test compound, compared with the relaxation state of the muscle in the absence of the test compound, is an indication that the test compound is an arginase inhibitor antagonist.

The invention also includes methods of treating a disease or condition associated with upregulation of arginase in a mammal, comprising administering to the mammal an effective amount of a compound of the present invention or a pharmaceutically acceptable salt thereof; wherein the disease or condition is a gastrointestinal disease, a pulmonary inflammatory disease, a sexual arousal disorder, a cardiovascular disorder, a hemolytic disorder, an autoimmune disease, wound healing, a disease caused by parasitic protozoa, a disease caused by bacteria, a cancer, pre-term labor, psoriasis, or a combination thereof.

Inhibiting arginase impacts cancer in two ways. The first way is relief from immune-suppression that leads to tolerance of the tumor and the second way is by restricting the production of ornithine and subsequent polyamines, which have a role in proliferation.

In one embodiment, the gastrointestinal disease is a gastrointestinal motility disorder, inflammatory bowel disease, Crohn's disease, ulcerative colitis, gastric ulcer, adenotonsilar disease or a combination thereof.

In one embodiment, the pulmonary inflammatory disease is asthma, chemically-induced lung fibrosis, idiopathic pulmonary fibrosis, cystic fibrosis, chronic obstructive pulmonary disease (COPD) or a combination thereof.

In one embodiment, the sexual arousal disorder is male erectile dysfunction, Peyronie's Disease, or a female sexual arousal disorder.

In one embodiment, the cardiovascular disorder is endothelial vascular dysfunction in atherosclerosis, hypertension, ischemia reperfusion injury, peripheral vascular disease, peripheral arterial disease, subarachnoid hemorrhage, hypercholesterolemia, diabetes, diabetic cardiovascular disease, pulmonary arterial hypertension, Reynaud's disease, or a combination thereof.

In one embodiment, the hemolytic disorder is paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, malaria, cardiopulmonary bypass, mechanical heart valve-induced anemia, chemical induced anemia, or a combination thereof.

In one embodiment, the autoimmune disease is encephalomyelitis, multiple sclerosis, anti-phospholipid syndrome 1, autoimmune hemolytic anemia, chronic inflammatory demyelinating polyradiculoneuropathy, dermatitis herpetiformis ("Celiac Disease"), dermatomyositis, myasthenia gravis, pemphigus, rheumatoid arthritis, stiff-person syndrome, type 1 diabetes, ankylosing spondylitis, or a combination thereof.

In one embodiment, the condition is wound healing.

In one embodiment, the disease caused by parasitic protozoa is African sleeping sickness, Chagas' disease, leishmaniasis, malaria, or a combination thereof.

In one embodiment, the cancer is renal cell carcinoma, prostate cancer, colorectal cancer, breast cancer, skin cancer, lung cancer, ovarian cancer, gastric cancer, or a combination thereof. In another embodiment, the skin cancer is a squamous cell cancer, basal cell cancer, or a combination thereof.

In one embodiment, the condition is pre-term labor.

In one embodiment, the condition is Reynaud's disease.

In addition, the compounds and compositions of the invention are useful as anti-fungicides in agriculturally or otherwise economically important plant life. The compounds and compositions of the invention can be therapeutically administered to a plant by spraying or other means well known in the art of plant biology.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

Compounds of the invention may be prepared by one or more of the following general methods. All parts and percentages are by weight, unless otherwise stated. When ranges are used herein for physical properties, such as molecular weight, or chemical properties, such as chemical formulae, all combinations and subcombinations of such ranges therein are intended to be included as specific embodiments hereof. It should be understood that these examples, while indicating preferred embodiments of the invention, are given by way of illustration only. From the above discussion and these examples, one skilled in the art may ascertain the essential characteristics of this invention, and without departing from the spirit and scope thereof, may make various changes and modifications of the invention to adapt it to various usages and conditions. So that these synthetic methods may be more fully understood, some examples of solution-phase protocols for making specific compounds are also presented. All of the starting materials are commercially available or may be prepared by procedures described in these schemes or by procedures that would be well known to one of ordinary skill in organic chemistry.

General Procedure A. Preparation of Amino Ester Ketimine from a-Bromo Acetate

As illustrated in FIG. 1, benzophenone inline (6.68 mL, 40.0 mmol) and tert-butyl bromoacetate 3c (5.9 mL, 40.0 mmol) were dissolved in 40 mL acetonitrile. DIEA (6.95 mL, 40.0 mmol) was added and the reaction mixture heated to reflux for 14 hr. The reaction mixture was cooled to room temperature, neutralized by the addition of 50% aqueous acetic acid, and cooled to 0° C. The solids were collected by filtration and then washed with cold ethanol. Product 4c was dried in vacuo to give 9.05 g (77%) which was used without further purification. MS (LC/MS, ESI): 296 (M+H), 240 (M−tBu+H). $^1$H NMR (300 MHz, CDCl$_3$, δ): 7.5-8.0 (m, 10H), 4.5 (s, 2H), 1.4 (s, 9H). (see O'Donnell, 2004, Acc. Chem. Res. 37, 506)

General Procedure B. Synthesis of Alkyl Iodide Reagents

As illustrated in FIG. 2, piperazine 6 (3.0 mmol) and 3-bromo-1-propanol (3.75 mmol) were dissolved in 15 mL of 2-butanone. Solid K$_2$CO$_3$ (6.0 mmol) was added and the reaction stirred at reflux for 18-24 hr. The mixture was allowed to cool to room temperature and diluted with EtOAc, washed 3× with water and 1× with brine. The organic solution was dried over magnesium sulfate and concentrated in vacuo to give 7. Product compound 7 was assayed by LC/MS and $^1$H NMR, and used without further purification.

As illustrated in FIG. 2, compound 8 (1.03 g, 7.1 mmol) was mixed with an aldehyde 9 (7.1 mmol) in 30 mL DCM/TMOF 1:1 for about 5 min. Triacetoxyborohydride (4.15 g, 19.6 mmols) was added in four portions to the mixture and the reaction stirred for 1.5 hr. The reaction mixture was diluted with EtOAc and 1 N NaOH was added. The layers were separated and the organic solution washed 2× with 1 N NaOH solution and 1× with brine. The organic solution was dried over magnesium sulfate and concentrated in vacuo to give of 10. Product compound 10 was assayed by LC/MS and $^1$H NMR, and it used without further purification.

As illustrated in FIG. 2, imidazole (960 mg, 14.2 mmols) and triphenylphosphine-resin (3.30 g, 3.0 mmol/g, 9.9 mmol) were suspended in 50 mL DCM under argon. Iodine (2.52 g, 10.0 mmol) was added to this mixture and stirred for 10-15 minutes. Compound 10 was added in 10 mL DCM then stirred for 12-18 hr. The reaction mixture was filtered and washed with 3 portions of DCM of 10 mL each to remove the resin and then 25 mL of saturated sodium thiosulfate solution was added along with 10-15 mL water and the mixture was stirred for 10-15 minutes. The mixture was separated and the organic layer washed 3× with water and 1× with brine. The organic solution was dried over magnesium sulfate and concentrated in vacuo to give an oil 11.

General Procedure C. Alkylation of Glycine Ketimine with Unactivated Alkyl Halides As illustrated in FIGS. 3 and 7, compound 4c (1 mmol) was dissolved in 5 mL dry THF (tetrahydrofuran) under argon and cooled to −78° C. A 1 M solution of base, LiHMDS (lithium hexamethyldisilazane), in THF (1.05 mL) was added to the reaction mixture and stirred at −78° C. for 45 minutes, and then an alkyl halide such as compound 11 (1.05 mmol) in 3 mL dry THF was added. The reaction mixture was stirred at −78° C. for 30 minutes and then allowed to warm to room temperature and stirred for 8-18 hr. The reaction mixture was diluted with 20 mL EtOAc (ethyl acetate) and washed with water and then brine. The organic solution was filtered over a bed of Hydromatrix brand diatomaceous earth and concentrated to dryness. This residue was dissolved in a small amount of DCM, applied to a dry silica gel column, and eluted with mixtures of EtOAc/hexane (1-5%) to yield compound 12 or 24.

General Procedure D. Alkylation of Amino Ester Ketimine with Crotyl Bromide

As illustrated in FIGS. 3 and 7, compound 12 or 24 (1 mmol) was dissolved in 5 mL dry THF under argon and cooled to −78° C. A 0.5 M solution of KHMDS (potassium hexamethyldisilazane) in toluene (1.05 mL) was added to the reaction mixture and stirred at −78° C. for 45 minutes, and then crotyl bromide (1.05 eq) was added. The reaction mixture was stirred at −78° C. for 30 minutes and then allowed to warm to room temperature and stirred for 8-18 hr. The reaction mixture was diluted with 20 mL EtOAc and washed with water and then brine. The organic solution was filtered over a bed of Hydromatrix brand diatomaceous earth and concentrated to dryness. This residue was dissolved in a small amount of DCM, applied to a dry silica gel column, and eluted with mixtures of EtOAc/hexane (1-5%) to yield compound 13 or 25.

General Procedure E. Hydroboration of Crotyl Sidechain As illustrated in FIGS. 3 and 7-8, under an argon atmosphere [Ir(cod)Cl]$_2$ (34 mg, 0.05 mmol, 5 mol %) and DPPM (bis (diphenylphosphino)methane, 38 mg, 0.10 mmol, 10 mol %) were dissolved in 5 mL dry DCM. Pinacol borane (175 μL, 1.20 mmol) and compound 13, 27, or 32 (1 mmol) were dissolved in 5 mL dry DCM and added. The reaction mixture was stirred at room temp for 24 hr. One mL of MeOH/H$_2$O (1:1) was added to quench the reaction. The mixture was concentrated in vacuo, dissolved with 20 mL EtOAc, and washed with water and then brine. The organic solution was filtered over a bed of Hydromatrix brand diatomaceous earth and concentrated to dryness. This residue was dissolved in a small amount of DCM, applied to a dry silica gel column, and eluted with mixtures of EtOAc/hexane (5-10%) to yield pure compound 14, 28 or 33.

General Procedure F. Selective Boc Removal

As illustrated in FIGS. 4 and 6, compound 14 or 19 is converted to compound 15 or 20 by treatment with 25-50% TFA (trifluoroacetic acid)/DCM under argon for 12-16 hr. The reaction mixture is concentrated to dryness in vacuo, a few mL of DCM added and this solution is reconcentrated to dryness and then the residue dried in vacuo for several hr and then placed under an argon atmosphere.

General Procedure G. Alkylation of Piperazine Side Chain

As illustrated in FIG. 4, compound 15 was dissolved in anhydrous DMF under argon and 2.5 eq of potassium carbonate was added followed by 1-2 eq of an alkyl halide such as benzyl bromide. The reaction was stirred at room temperature for 12-18 hr. The reaction mixture was diluted with EtOAc and washed 2× with 1 N NaOH, 1× with water, and 1× with brine. The organic solution was filtered over a bed of Hydromatrix brand diatomaceous earth and concentrated to dryness and compound 16 was used as is for the subsequent global deprotection step.

General Procedure H. Acylation of Piperazine Side Chain

As illustrated in FIGS. 4 and 6, compound 15 or 20 was dissolved in anhydrous DMF under argon and DIEA was added until the solution was basic. The acylating agent (sulfonyl chloride, acid chloride, or isocyanate) (1.2 eq) was added and the reaction stirred for 12-18 hr. The reaction mixture was diluted with EtOAc and washed 2× with 1 N NaOH, 1× with water, and 1× with brine. The organic solution was filtered over a bed of Hydromatrix brand diatomaceous earth and concentrated to dryness to give compound 17, 18, 21, 22 or 23 that was used as is for the subsequent global deprotection step.

General Procedure I. Ketimine Removal and Reprotection of α-Amine with Cbz Group As illustrated in FIG. 6, compound 14 was treated with 1 N HCl/THF (1:2) for 30 min to 1 hr at room temperature. The reaction mixture was diluted with EtOAc and 1 N NaOH and the layers separated. The organic layer was washed 1× with 1 N NaOH, 1× with H$_2$O and 1× with brine. The organic solution was dried over MgSO$_4$, filtered, and concentrated to dryness. This residue was dissolved in anhydrous THF under argon, 1.2 eq of DIEA was added followed by 1.2 eq of benzyl chloroformate, and this mixture was stirred at room temperature for 12-18 hr. The mixture was diluted with EtOAc, washed 3× with 0.1 N HCl, and 1× with brine. The organic solution was dried over MgSO$_4$, filtered, and concentrated to dryness. This residue was dissolved in a small amount of DCM, applied to a dry silica gel column, and eluted with mixtures of EtOAc/hexane (5-10%) to give pure compound 19.

General Procedure J. Neutral Conditions for Ketimine Removal and Reprotection of α-Amine with Cbz Group As illustrated in FIG. 7, 6.37 g (12.2 mmols) of 25 was dissolved in 60 mL dry THF under argon and 30 mL of 1 M hydroxylamine hydrochloride was added to this solution. The reaction was rapidly mixed at room temperature until the starting material was completely consumed (24-48 hr). Ethyl acetate (100 mL) and 1 N NaOH (50 mL) was added to the reaction mixture. The layers were separated and the aqueous solution was washed 3× with EtOAc. The organic solutions were combined, washed 1× with brine, dried over MgSO$_4$, filtered and concentrated in vacuo to an oil. This residue was dissolved in a small amount of DCM, applied to a dry silica gel column, and eluted with mixtures of EtOAc/hexane (5-50%) to give pure compound 26. Compound 26 was dissolved in 40 mL dry THF under argon and 2.4 mL DIEA (13.8 mmols) was added followed by 2.0 mL of benzyl chloroformate (13.8 mmols) and the reaction stirred at room temperature overnight. The reaction mixture was diluted with 100 mL EtOAc washed with 3×0.1 N HCl and 1× with brine, dried over MgSO$_4$, filtered and concentrated in vacuo to give an oil that was eluted over a silica gel column with mixtures of EtOAc/hexane (5-10%) to yield 3.28 g (59%) of pure compound 27, General Procedure K Boc Protection of α-Amine As illustrated in FIG. 8, Compound 26 was dissolved in THF/water (1:1) and 3.5 eq of NaHCO$_3$ and 2 eq of di-tert-butyl dicarbonate were added to this solution. After 36 hr the reaction mixture was diluted with EtOAc and washed 3× with water and 1× with brine. The organic layer was dried over MgSO$_4$, filtered and concentrated in vacuo to yield an oil that was purified by eluted over a silica gel column with mixtures of EtOAc/hexanes (2-50%) to yield pure compound 32.

General Procedure L. TBS Ether Removal and Conversion of Hydroxyl to Iodide

As illustrated in FIGS. 7 and 8, 0.8 mmol of compound 28 or 33 was dissolved in 5 mL dry THF under argon and 4 mL 0.2 N HCl was added to this solution. The mixture was stirred rapidly at room temperature overnight. The mixture was diluted with 50 mL EtOAc, washed 1× with water, 1× with sat NaHCO$_3$ solution and 1× with brine, dried over MgSO$_4$, filtered and concentrated in vacuo to yield 0.411 g of a tan oil (29) that could be used as is in the next reaction or it could be eluted over a silica gel column with mixtures of EtOAc/hexanes (10-25%). Imidazole (0.11 g, 1.62 mmols) and 0.375 g Ph$_3$P-resin (3.0 mmols/g, 1.12 mmols) were placed under argon and 5 mL dry DCM was added. Iodine (0.290 g, 1.15 mmols) was added and the mixture sonicated 2-3 min to dissolve the iodine. Then compound 29 in 2 mL dry DCM was added to the reaction mixture followed by 2 mL DCM as a rinse and this mixture was stirred overnight at room temperature. The resin was filtered and washed well with DCM. The DCM solution was washed 1× with sat sodium thiosulfate solution and then 1× with water and 1× with brine, dried over MgSO$_4$, filtered and concentrated in vacuo to yield 459 mg (93%) of an oil characterized as compound 30 or 34.

General Procedure M. Chiral Chromatography of Compound 29

As illustrated in FIGS. 11 and 12, the enantiomers of compound 29 was separated on a CHIRALCEL®OZ 20µ AD-H chromatography column with 10% isopropanol/hexane to yield pure compounds 36a and 36b. On an analytical column Peak 1 eluted at 6.34 min and Peak 2 eluted at 13.52 min.

General Procedure N. Nucleophilic Addition to Alkyl Iodides

As illustrated in FIGS. 7 and 8, Compound 30 or 34 (0.149 mmols) in 0.5 mL DMF was added to a mixture of a nucleophile, such as but not limited to a substituted piperidine hydrochloride (1.1 eq), and dry potassium carbonate (0.080 g, 0.58 mmols). This mixture was rapidly stirred overnight at room temperature. The reaction mixture was diluted with 10 mL EtOAc, washed 2× with 1 N NaOH, 1× with water and 1× with brine. The EtOAc solution was filtered over a column of Hydromatrix and the solution concentrated in vacuo to yield crude 31 or 35. These compounds could be used as is or were eluted over a silica gel column with mixtures of EtOAc/hexanes (20-50%).

General Procedure O. Global Deprotection Procedure (1)

As illustrated in FIG. 5, compound 14 was dissolved in 6 N HCl/DCM 2:1 and stirred overnight at 70° C. This reaction mixture was cooled and extracted 3× with ether. The aqueous layer was lyophilized and the residue was purified by prep HPLC using acetonitrile/water gradients containing 0.075% TFA on C18 silica prep columns.

General Procedure P. Global Deprotection Procedure (2)

As illustrated in FIGS. 5, 10 and 14, compound 14, 35 or 47 was dissolved in 50-100% TFA/DCM under argon and stirred at room temperature for 1-2 hr. The reaction mixture was concentrated to dryness in vacuo and the residue placed under argon. This residue was dissolved in 3-5 mL 1 N HCl plus an equal amount of diethyl ether. Phenyl boronic acid (5 eq) was added and the reaction mixture was rapidly stirred at room temperature for 12-18 hr. The layers were separated and the aqueous solution was washed 5× with diethyl ether. The aqueous layer was lyophilized and the residue was purified by prep HPLC using acetonitrile/water gradients containing 0.075% TFA on C18 silica prep columns.

General Procedure Q. Global Deprotection Procedure (3)

As illustrated in FIGS. 10 and 14, compound 31, 48 or 50 was dissolved in THF and 2-3 eq of 1 N HCl was added. Pd/C (10%, 0.1 eq) was added to this mixture and the reaction was placed under a hydrogen atmosphere for 1-2 hr. The reaction was filtered over Celite and washed with acetonitrile 2-3×. The reaction mixture was concentrated to dryness in vacuo and the residue placed under argon and General Procedure P was followed for the complete removal of protecting groups. The order of reaction may change depending upon the specific chemical compatibility of the groups in R$^1$ of these compounds.

General Procedure R. Esterification by Acidic Methods

As illustrated in scheme A in FIG. 13, Compound 41 (75-100 mg) was added to 6 mL of an alcohol (R$^2$OH) and 0.5 mL thionyl chloride was added. The reaction mixture was refluxed for 16 hr, cooled and concentrated in vacuo. Compound 42 was purified by prep HPLC using an acetonitrile/water gradient.

General Procedure S. Esterification by Basic Methods

As illustrated in scheme B in FIG. 13, 100 mg of Compound 43, 44, 45, or 46 was dissolved in 5 mL DMF and 2.5 eq of $K_2CO_3$ was added followed by 1.2 eq of an alkyl halide such as isopropyl bromide. If an alkyl chloride was used, an equivalent of NaI was also added to the reaction mixture. The reaction mixture was stirred at 25-50° C. for 4-16 hr. The product was isolated by dilution with EtOAc, washed 3× with water, and concentrated in vacuo to give compound 47, 48, 49 or 50. These products were eluted over a silica gel column using mixtures of EtOAc/Hexanes (20-100%) or purified by reverse phase HPLC using acetonitrile/water gradients.

General Procedure T. Esterification by DCC/DMAP

As illustrated in FIG. 13, Compound 43, 44, 45 or 46 was dissolved in DCM and triethylamine (3 eq), DCC (2 eq), DMAP and 1.2 eq of an alcohol ($R^2OH$). The reaction mixture was stirred at room temperature for 16 h and then it was concentrated in vacuo. The residue was eluted over a silica gel column with mixtures of EtOAc/Hexanes (20-50%) or purified by reverse-phase HPLC using acetonitrile/water gradients to give compound 47, 48, 49 or 50.

General Procedure U. Esterification by Preformed Acid Chloride

As illustrated in scheme D in FIG. 13, compound 45 was dissolved in DCM and 1-2 drops of DMF was added followed by 1.5 eq of oxalyl chloride at 0° C. The reaction was allowed to warm to room temperature and then stirred for 1-2 hr. The reaction mixture was concentrated in vacuo and dry DCM was added and then reconcentrated in vacuo. The residue was dried in vacuo for 1-2 hr. This residue was dissolved in DMF and 1.5-3 eq of $R^2OH$ was added and the reaction mixture stirred for 16 hr and then it was concentrated in vacuo. The residue was eluted over a silica gel column with mixtures of EtOAc/Hexanes (20-50%) or purified by reverse-phase HPLC using acetonitrile/water gradients to give compound 49.

General Procedure V. Global Deprotection of Prodrug Esters

As illustrated in scheme A in FIG. 14, compound 47, 48, or 50 were deprotected at the α-amine and boronic ester to give compounds of this invention 42 by the procedures outlined in FIG. 10 and General Procedures O, P, or Q. Additionally, the Cbz protecting group on compound 48 was removed by refluxing in TFA for 16 hr.

As illustrated in scheme B in FIG. 14, the Fmoc group of compound 49 was cleaved after treatment with 5-20% piperidine or piperazine in DMF for 30 min-4 hr at room temperature.

The pinacol boronate esters intermediates were dissolved in 3-5 mL 1 N HCl plus an equal amount of diethyl ether. Phenyl boronic acid (5 eq) was added and the reaction mixture was rapidly stirred at room temperature for 12-18 hr. The layers were separated and the aqueous solution was washed 5× with diethyl ether. The aqueous layer was lyophilized and the residue was purified by prep HPLC using acetonitrile/water gradients containing 0.075% TFA on C18 silica prep columns to give compound 42.

Comparative Example 4

2-Amino-6-borono-2-(3-(piperazine-1-yl)propyl) hexanoic acid trifluoroacetate salt (1a)

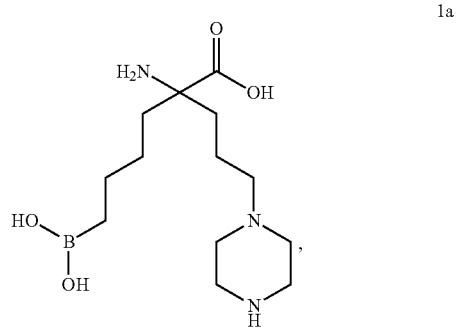 [SMILES: NC(CCCCB(O)O)(CCCN1CCNCC1)C(=O)O]

1a tert-Butyl 4-(5-tert-butoxy-4-(diphenylmethylene-amino)-5-oxopentylpiperazine-1-carboxylate

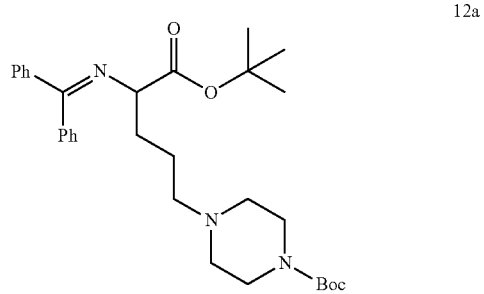 [SMILES: CC(C)(C)OC(=O)C(CCCN1CCN(C(=O)OC(C)(C)C)CC1)N=C(c1ccccc1)c1ccccc1]

12a

Compound 12a, 10.0 g, (85%) was obtained after reaction of 4c and 11 (where R=Boc) using General Procedure C described above, MS (LC/MS, ESI): 522 (M+H), 466 (M−tBu+H). $^1$H NMR (300 MHz, CDCl$_3$, δ): 7.4-8.0 (m, 10H), 4.9 (m, 1H), 3.2 (m, 4H), 2.4-2.5 (m, 6H), 2.0 (m, 2H), 1.4 (s, 18H), 1.3 (m, 2H).

tert-Butyl 4-(4-tert-butoxycarbonyl)-4-(diphenylm-
ethyleneamino)oct-6-enyl)piperazine-1-carboxylate

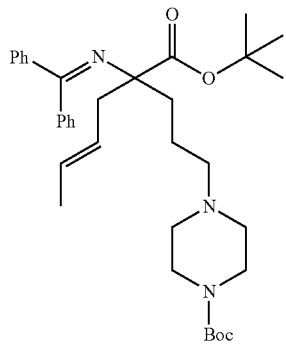
13a

Compound 13a, 10.4 g (94%), was obtained using General Procedure D described above. MS (LC/MS, ESI): 576.5 (M+H), 520.5 (M−tBu+H). $^1$H NMR (300 MHz, CDCl$_3$, δ): 7.4-8.0 (m, 10H), 5.5 (m, 2H), 3.2 (m, 4H), 2.4-2.5 (m, 6H), 2.05 (d, 3H), 2.0 (m, 4H), 1.4 (s, 18H), 1.3 (m, 2H).

tert-Butyl 4-(4-tert-butoxycalbonyl)-4-(diphenylm-
ethyleneamino)-8-(4,4,5,5-tetramethyl-1,3,2-diox-
aborolan-2-yl)octyl)piperazine-1-carboxylate

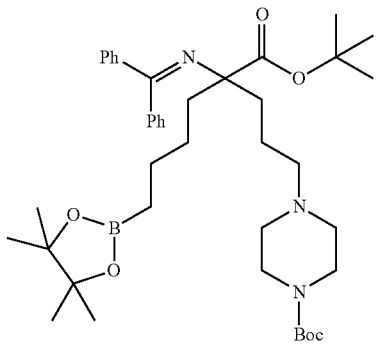
14a

Compound 14a, 9.0 g (71%), was obtained using General Procedure E described above. MS (LC/MS, ESI): 704.7 (M+H), 648.6 (M−tBu+H), $^1$H NMR (300 MHz, CDCl$_3$, δ): 7.4-8.0 (m, 10H), 3.2 (m, 4H), 2.4-2.5 (On, 6H), 2.0 (m, 4H), 1.4 (s, 18H), 1.3 (m, 4H), 1.25 (s, 12H), 0.8 (t, 2H).

Compound 1a, 20 mg (45%), was obtained as the TFA salt by using General Procedure O described above after purification by prep HPLC. MS (LC/MS, ESI): 284 (M−H$_2$O+H). $^1$H NMR (300 MHz, D$_2$O, δ): 2.8 (m, 4H), 2.4-2.5 (m, 6H), 2.0 (m, 4H), 1.3 (m, 4H), 0.8 (t, 2H).

Example 2

The following compound listed in Table 4, below, was synthesized in analogous manner as described above for compound 1a,

TABLE 4

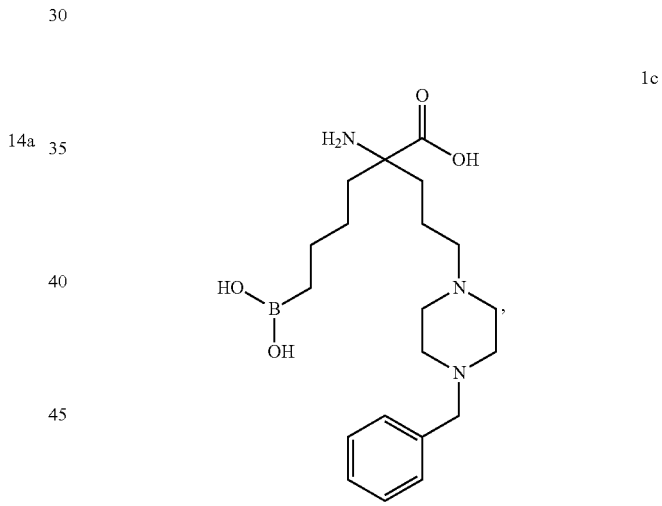

| Example No. | Cmpd No. | R$^1$ | Amt Isolated | MS Data | Physical Appearance |
|---|---|---|---|---|---|
| 2 | 1b | | 7 mg | 426 408 | White flocculent powder |

Example 3

2-amino-2-(3-(4-benzylpiperazin-1-yl)propyl)-6-
boronohexanoic acid trifluoroacetate salt (1c)

1c

Compound 14a was treated with 20% TFA/DCM under argon as described above in General Procedure F to yield compound 15c, which was treated with benzyl bromide as described above in General Procedure G to yield compound 16c. This compound was used as is in General Procedure P to yield 13 mg of 1c (19% for 3 steps) after purification by prep HPLC as the trifluoroacetate salt. MS (LC/MS, ESI): 374 (M−H$_2$O+H). $^1$H NMR (300 MHz, D$_2$O, δ): 7.2-7.4 (m, 5H), 3.8 (s, 2H), 3.2 (m, 4H), 2.4-2.5 (m, 6H), 2.0 (m, 4H), 1.3 (m, 4H), 0.8 (t, 2H).

Examples 4-15

The following compounds listed in Table 5, below, were synthesized in analogous manner as described above for compound 1c. In Table 5, each compound has the following chemical structure (each example in the Table has a different R$^1$ group):

TABLE 5
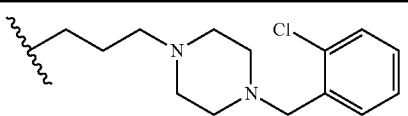
| Example No. | Cmpd No. | R¹ | Amt Isolated | MS Data | Physical Appearance |
|---|---|---|---|---|---|
| 4 | 1d | 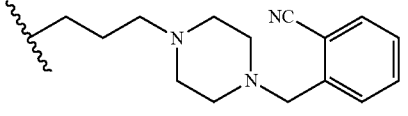 [SMILES: *CCCN1CCN(Cc2ccccc2C#N)CC1] | 7 mg | 426 408 | White flocculent powder |
| 5 | 1e | 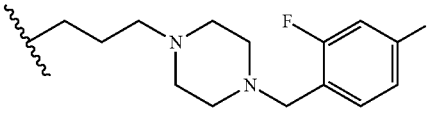 | 10 mg | 417 399 | White flocculent powder |
| 6 | 1f | 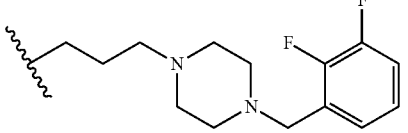 | 12 mg | 428 410 | White flocculent powder |
| 7 | 1g | 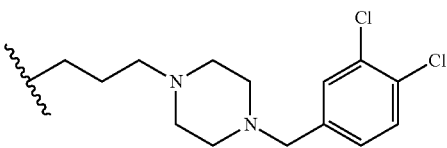 [SMILES: *CCCN1CCN(Cc2ccc(Cl)c(Cl)c2)CC1] | 14 mg | 428 410 | White flocculent powder |
| 8 | 1h | 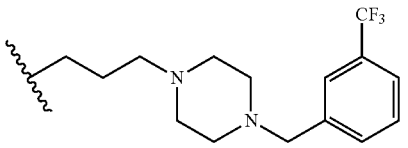 [SMILES: *CCCN1CCN(Cc2cccc(C(F)(F)F)c2)CC1] | 10 mg | 460 442 | White clear glass |
| 9 | 1i | 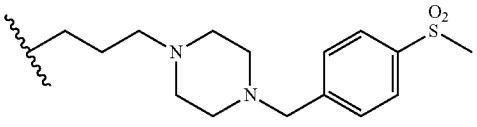 [SMILES: *CCCN1CCN(Cc2ccc(S(C)(=O)=O)cc2)CC1] | 9 mg | 460 442 | White flocculent powder |
| 10 | 1j | 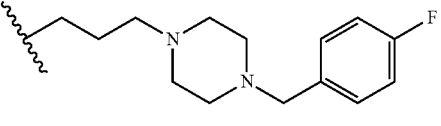 [SMILES: *CCCN1CCN(Cc2ccc(F)cc2)CC1] | 6 mg | 470 452 | White flocculent powder |
| 11 | 1k | 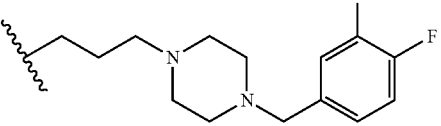 | 6 mg | 410 392 | White flocculent powder |
| 12 | 1l | | 17 mg | 428 410 | White flocculent powder |

TABLE 5-continued

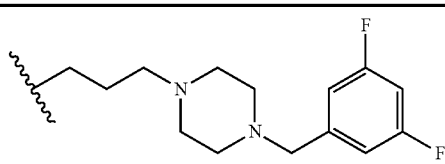

| Example No. | Cmpd No. | R¹ | Amt Isolated | MS Data | Physical Appearance |
|---|---|---|---|---|---|
| 13 | 1m | 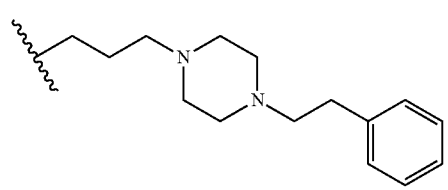 [SMILES: *CCCN1CCN(CCc2ccccc2)CC1] | 23 mg | 428 410 | White flocculent powder |
| 14 | 1n | 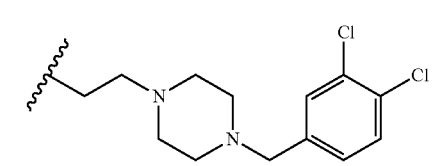 [SMILES: *CCN1CCN(Cc2ccc(Cl)c(Cl)c2)CC1] | 15 mg | 406 388 | Colorless glass |
| 15 | 1o | 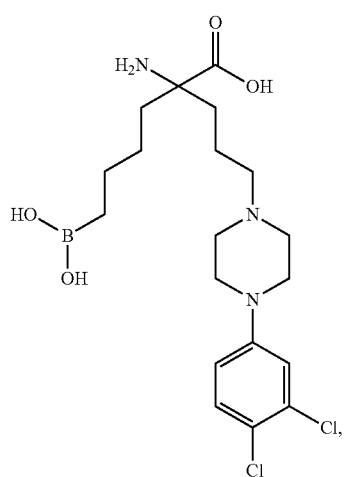 | 2 mg | 446 428 | White flocculent powder |

Example 16

2-amino-6-borono-2-(3-(4-(3,4-dichlorophenyl)piperazine-1-yl)propylhexanoic acid (1p)

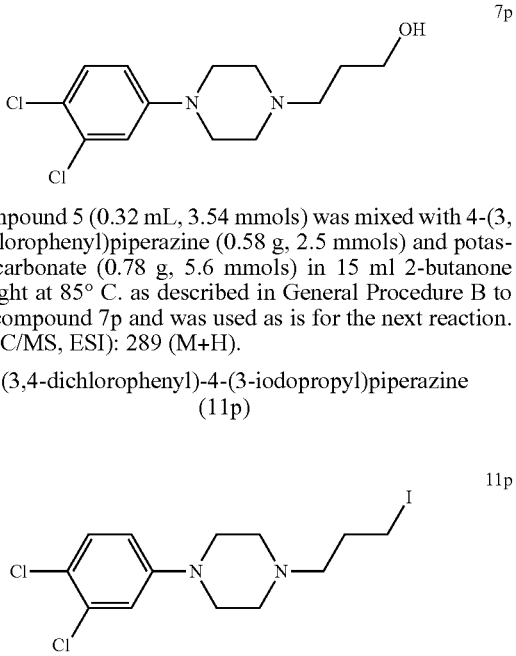

3-(4-(3,4-dichlorophenyl)piperazine-1-yl)propan-1-ol(7p)

Compound 5 (0.32 mL, 3.54 mmols) was mixed with 4-(3,4-dichlorophenyl)piperazine (0.58 g, 2.5 mmols) and potassium carbonate (0.78 g, 5.6 mmols) in 15 ml 2-butanone overnight at 85° C. as described in General Procedure B to yield compound 7p and was used as is for the next reaction. MS (LC/MS, ESI): 289 (M+H).

1-(3,4-dichlorophenyl)-4-(3-iodopropyl)piperazine (11p)

Compound 7p was mixed with triphenylphosphine resin, imidazole and iodine in DCM as described in General Procedure B. The product compound 11p was used without further purification for the next reaction, MS (LC/MS, ESI): 399 (M+H).

tert-Butyl 5-(4-(3,4-dichlorophenyl)piperazine-1-yl-2-(diphenylmethyleneamino) pentanoate (12p)

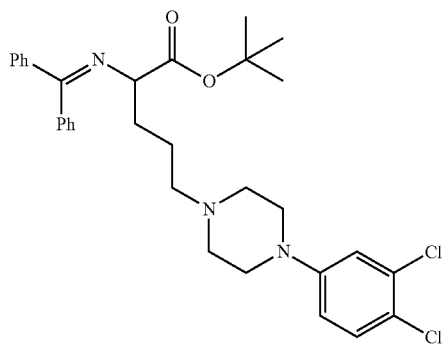

12p

Compound 12p, 0.497 g (37%), was obtained using General Procedure C described above. MS (LC/MS, ESI): 566 (M+H), 510 (M–tBu+H). $^1$H NMR (300 MHz, CDCl$_3$, δ): 7.4-8.0 (m, 10H), 6.8-7.2 (m, 3H), 4.1 (t, 1H), 3.2-3.6 (m, 8H), 2.4-2.5 (t, 2H), 1.7-2.0 (m, 4H), 1.4 (s, 9H).

tert-Butyl 2-(3-(4-(3,4-dichlorophenyl)piperazine-1-yl)propyl)-2-(diphenylmethyleneamino)hex-4-enoate (13p)

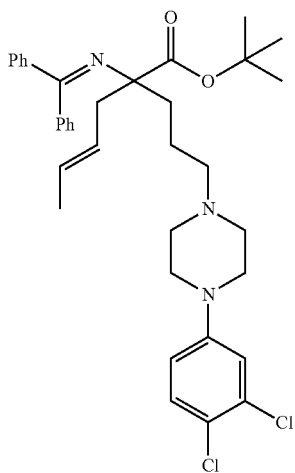

13p

Compound 13p, 0.359 g (94%), was obtained using General Procedure D described above. MS (LC/MS, ESI): 620 (M+H), 564 (M–tBu+H). $^1$H NMR (300 MHz, CDCl$_3$, δ): 7.4-8.0 (m, 10H), 6.8-7.2 (m, 3H), 5.4-5.6 (m, 2H), 3.2-3.6 (m, 8H), 2.4-2.5 (m, 4H), 1.7-2.0 (m, 4H), 1.6 (d, 3H), 1.4 (s, 9H).

tert-Butyl-2-(3-(4-(3,4-dichlorophenyl)piperazin-1-yl)propyl-2-(diphenylmethylene amino)-6-(4,4,5,5-tetramethyl-1,3,2-dioxaborolan-2-yl)hexanoate (14p)

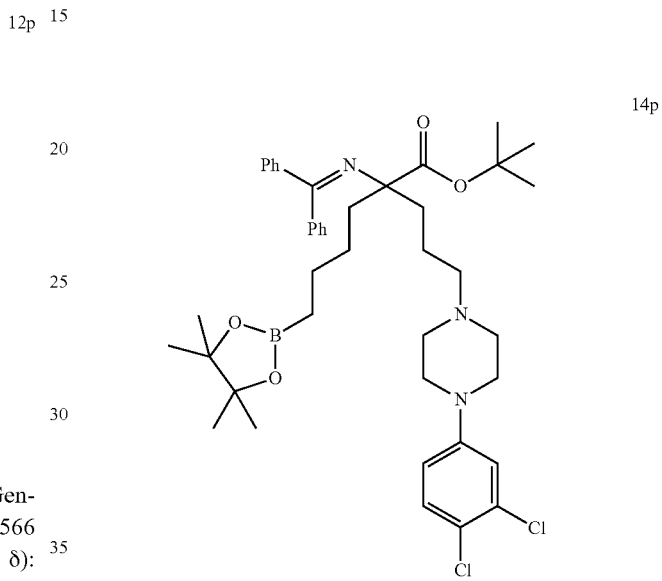

14p

Compound 14p, 0.302 g (70%), was obtained using General Procedure E described above, MS (LC/MS, ESI): 748 (M+H), 692 (M–tBu+H). $^1$H NMR (300 MHz, CDCl$_3$, δ): 7.4-8.0 (m, 10H), 6.8-7.2 (m, 3H), 3.2-3.6 (m, 8H), 2.4-2.5 (m, 4H), 1.6-2.0 (m, 8H), 1.4 (s, 9H), 1.25 (s, 12H), 0.8 (t, 2H).

Finally, 128 mg (54%) of compound 1p, the structure of which is illustrated above, was obtained using General Procedure O, described above. MS (LC/MS, ESI): 427 (M–H$_2$O+H). $^1$H NMR (300 MHz, D$_2$O, δ): 7.4 (m, 1H), 6.9 (m, 2H), 3.2-3.6 (m, 8H), 2.4-2.5 (m, 4H), 2.0 (m, 4H), 1.3 (m, 4H), 0.8 (t, 2H).

Examples 17-25

The following compounds listed in Table 6, below, were synthesized in analogous manner as described above for compound 1p. In Table 6, each compound has the following chemical structure (each example in the Table has a different R$^1$ group):

TABLE 6
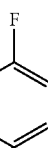
| Example No. | Cmpd No. | R¹ | Amt Isolated | MS Data | Physical Appearance |
|---|---|---|---|---|---|
| 17 | 1q | 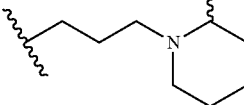 | 27 mg | 395 377 | White flocculent powder |
| 18 | 1r |  | 7 mg | 287 269 | Colorless glass |
| 19 | 1s | 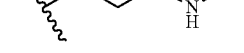 | 5 mg | 445 427 | White flocculent powder |
| 20 | 1t | 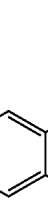 | 4 mg | 413 395 | White flocculent powder |
| 21 | 1u | 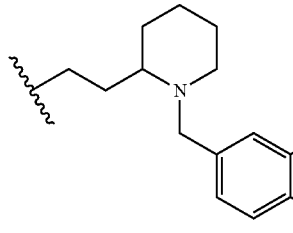 | 5 mg | 413 395 | White flocculent powder |

TABLE 6-continued
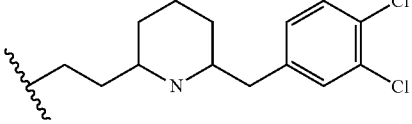
| Example No. | Cmpd No. | R¹ | Amt Isolated | MS Data | Physical Appearance |
|---|---|---|---|---|---|
| 22 | 1v | 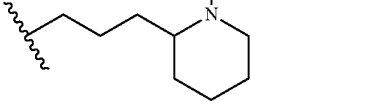 | 4 mg | 445 427 | White flocculent powder |
| 23 | 1w | 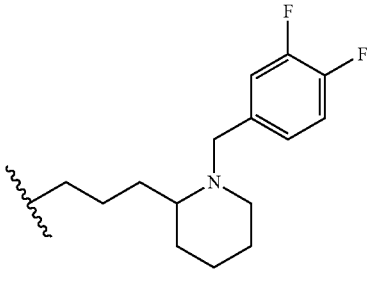 [SMILES: *CCCC1CCCCN1Cc1ccc(F)c(F)c1] | 5 mg | 459 441 | White flocculent powder |
| 24 | 1x | 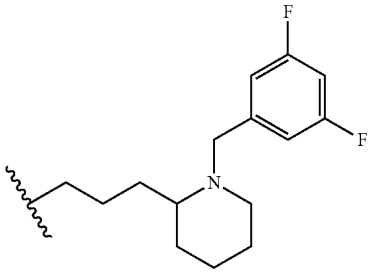 [SMILES: *CCCC1CCCCN1Cc1cc(F)cc(F)c1] | 4 mg | 427 409 | White flocculent powder |
| 25 | 1y | | 7 mg | 427 409 | White flocculent powder |

Example 26

2-amino-6-borono-2-(3-(3-phenylpiperidin-1-yl)propyl)hexanoic acid (1z)

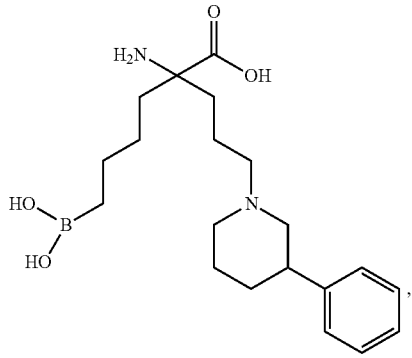

tert-Butyl 5-(tert-butyldimethylsilyloxy)-2-(diphenylmethyleneamino)pentanoate (24)

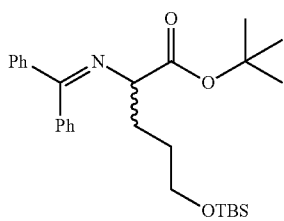

Compound 24, 13.43 g (82%) was obtained using General Procedure C described above. MS (LC/MS, ESI): 468.5 (M+H) NMR (300 MHz, CDCl$_3$, δ): 7.2-8.0 (m, 10H), 3.9 (m, 1H), 3.6 (t, 2H), 2.0 (m, 2H), 1.4-1.6 (m, 2H), 1.4 (s, 9H), 0.9 (s, 9H), 0.05 (s, 6H).

tert-Butyl 2-(3-(tert-butyldimethylsilyloxy)propyl)-2-(diphenylmethyleneamino)hex-4-enoate (25)

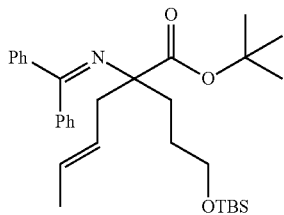

Compound 25, 11.23 g (75%) was obtained using General Procedure D described above. MS (LC/MS, ESI): 522.6 (M+H), 466.5 (M−tBu+H). $^1$H NMR (300 MHz, CDCl$_3$, δ):7.3-7.8 (m, 10H), 5.4-5.5 (m, 2H), 3.6 (t, 2H), 2.4-2.6 (m, 2H), 1.7-1.9 (m, 4H), 1.6 (d, 3H), 1.4 (s, 9H), 0.9 (s, 9H), 0.05 (s, 6H).

tert-Butyl 2-(benzyloxycarbonylamino)-2-(3-(tert-butyldimethylsilyloxy)propyl)hex-4-enoate (27)

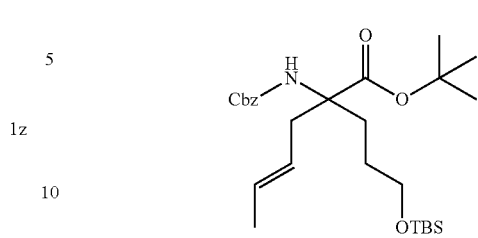

Compound 27, 3.28 g (59%) was obtained using General Procedure J described above. MS (LC/MS, ESI): 436.5 (M−tBu+H). $^1$H NMR (300 MHz, CDCl$_3$, δ): 7.3 (s, 5H), 5.8 (bs, 1H), 5.4-5.5 (m, 1H), 5.2-5.3 (m, 1H), 5.0-5.2 (q, 2H), 3.5-3.6 (m, 2H), 3.0-3.1 (m, 1H), 2.4-2.5 (m, 1H), 2.2-2.3 (m, 1H), 1.8-1.9 (m, 1H), (1.6 (d, 3H), 1.4 (s, 9H), 0.9 (s, 9H), 0.05 (s, 6H).

tert-Butyl 2-(benzyloxycarbonylamino)-2-(3-(tert-butyldimethylsilyloxy)propyl)-6-(4,4,5,5-tetramethyl-1,3,2-dioxaborolan-2-yl)hexanoate (28)

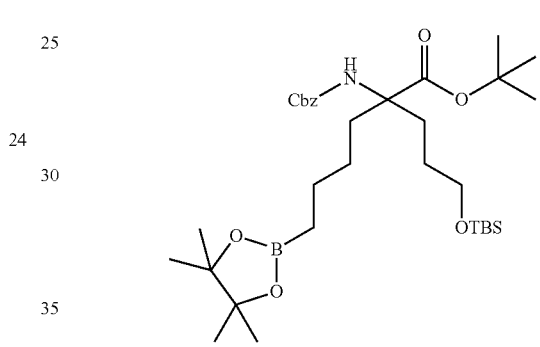

Compound 28, 2.44 g (59%) was obtained using General Procedure E described above. MS (LC/MS, ESI): 620.7 (M+H), 564.6 (M−tBu+H). $^1$H NMR (300 MHz, CDCl$_3$, δ): 7.4 (s, 5H), 5.9 (bs, 1H), 5.1 (s, 2H), 3.5-3.6 (m, 2H), 2.2-2.3 (m, 2H), 1.7-1.9 (m, 2H), 1.4 (s, 9H), 1.3-1.5 (m, 6H), 1.25 (s, 12H), 0.9 (s, 9H), 0.7 (t, 2H), 0.05 (s, 6H).

tert-Butyl 2-(benzyloxycarbonylamino)-2-(3-iodopropyl)-6-(4,4,5,5-tetramethyl-4,3,2-dioxaborolan-2-yl)hexanoate (30)

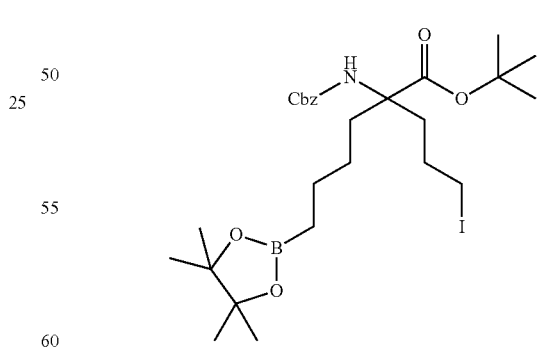

Compound 30, 0.459 g (93%) was obtained using General Procedure L described above. MS (LC/MS, ESI): 616 (M+H), 560 (M−tBu+H). $^1$H NMR (300 MHz, CDCl$_3$, δ): 7.2 (s, 5H), 5.8 (bs, 1H), 5.0 (s, 2H), 2.9-3.2 (m, 2H), 2.1-2.3 (m, 2H), 1.7-1.9 (m, 3H), 1.4 (s, 9H), 1.3-1.5 (m, 5H), 1.25 (s, 12H), 0.6 (t, 2H).

tert-Butyl 2-(benzyloxylcarbonylamino)-2-(3-(3-phenylpiperidin-1-yl)propyl)-6-(4,4,5,5-tetramethyl-1,3,2-dioxaborolan-2-yl)hexanoate (31z)

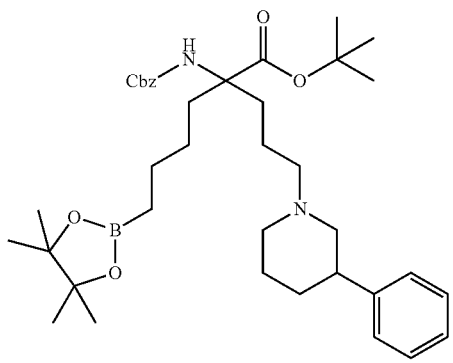

31z

Compound 31z, 0.134 g as a crude mixture was obtained using General Procedure N described above. MS (LC/MS, ESI): 649 (M+H).

Finally, 38 mg (42%) of compound 1z, the structure of which is illustrated above, was obtained using General Procedure Q, described above. MS (LC/MS, ESI): 359 (M−H$_2$O+H). $^1$H NMR (300 MHz, D$_2$O, δ): 7.2-7.4 (m, 5H), 2.8 (m, 1H), 2.4-2.5 (m, 6H), 2.0 (m, 4H), 1.4-1.8 (m, 6H), 1.3 (m, 4H), 0.8 (1, 2H).

Examples 27-98

The following compounds listed in Table 7, below, were synthesized in analogous manner as described above for compound 1z. The global deprotection schemes may be different for specific examples due to the chemical compatibility with R$^1$ groups and the protecting groups. In Table 7, each compound has the following chemical structure (each example in the Table has a different R$^1$ group):

TABLE 7

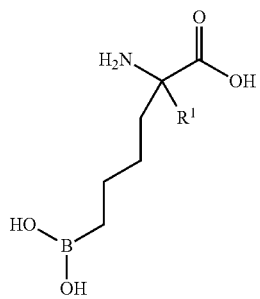

| Example No. | Cmpd No. | R$^1$ | Amt Isolated | MS Data | Physical Appearance |
|---|---|---|---|---|---|
| 27 | 1aa | 5-fluoro-1H-benzimidazol-2-yl-piperidinyl-propyl | 28 mg | 445, 427 | White flocculent powder |
| 28 | 1ab | 3,4-difluorobenzyl-piperidinyl-propyl | 17 mg | 427, 409 | White flocculent powder |
| 29 | 1ac | pyrimidin-2-ylmethyl-piperidinyl-propyl | 5 mg | 393, 375 | White flocculent powder |
| 30 | 1ad | spiro-isobenzofuran-piperidinyl-propyl | 4 mg | 405, 387 | Colorless glass |

TABLE 7-continued

| Example No. | Cmpd No. | R¹ | Amt Isolated | MS Data | Physical Appearance |
|---|---|---|---|---|---|
| 31 | 1ae | | 12 mg | 447 429 | White flocculent powder |
| 32 | 1af | | 50 mg | 478 460 | White flocculent powder |
| 33 | 1ag | | 26 mg | 445 427 | White flocculent powder |
| 34 | 1ah | | 22 mg | 461 443 | White flocculent powder |
| 35 | 1ai | | 19 mg | 435 417 | White flocculent powder |
| 36 | 1aj | | 42 mg | 395 377 | White flocculent powder |

TABLE 7-continued

| Example No. | Cmpd No. | R¹ | Amt Isolated | MS Data | Physical Appearance |
|---|---|---|---|---|---|
| 37 | 1ak | 4-(4-methoxyphenyl)piperidin-1-yl-butyl | 13 mg | 407, 389 | White flocculent powder |
| 38 | 1al | 4-(4-chlorophenyl)-3,6-dihydro-2H-pyridin-1-yl-butyl | 8 mg | 409, 391 | Colorless glass |
| 39 | 1am | 4-benzyl-4-hydroxypiperidin-1-yl-butyl | 25 mg | 407, 389 | White flocculent powder |
| 40 | 1an | 4-(4-chlorophenyl)-4-hydroxypiperidin-1-yl-butyl | 8 mg | 427, 409 | Colorless glass |
| 41 | 1ao | 4-[5-(trifluoromethyl)pyridin-2-yl]piperazin-1-yl-butyl | 9 mg | 447, 429 | Colorless glass |
| 42 | 1ap | 4-hydroxypiperidin-1-yl-butyl | 25 mg | 317, 299 | White solid |
| 43 | 1aq | 4-(valinyloxy)piperidin-1-yl-butyl | 43 mg | 416, 398 | Yellowish solid |

TABLE 7-continued
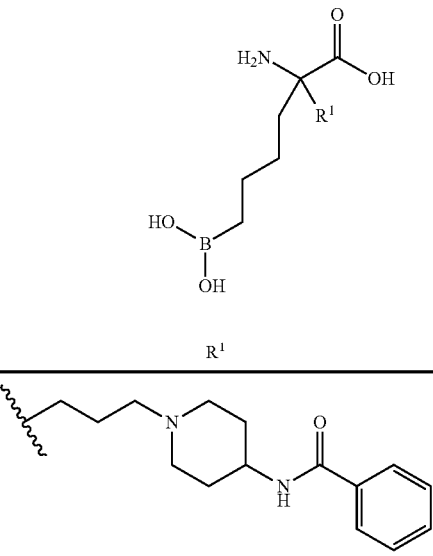
| Example No. | Cmpd No. | R¹ | Amt Isolated | MS Data | Physical Appearance |
|---|---|---|---|---|---|
| 44 | 1ar | 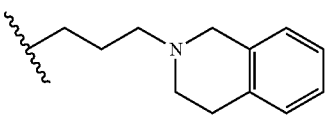 [SMILES: *CCCN1CCc2ccccc2C1] | 12 mg | 420<br>402 | White flocculent powder |
| 45 | 1as | 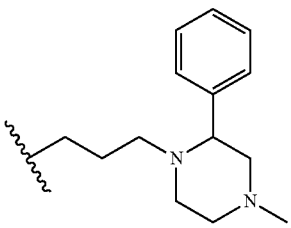 [SMILES: *CCCN1CCN(C)CC1c1ccccc1] | 9 mg | 349<br>331 | White flocculent powder |
| 46 | 1at | 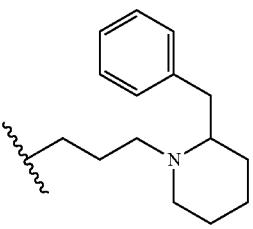 [SMILES: *CCCN1CCCCC1Cc1ccccc1] | 8 mg | 392<br>374 | White flocculent powder |
| 47 | 1au | 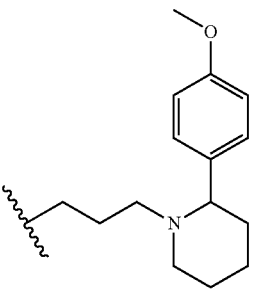 [SMILES: *CCCN1CCCCC1c1ccc(OC)cc1] | 15 mg | 391<br>373 | White flocculent powder |
| 48 | 1av | 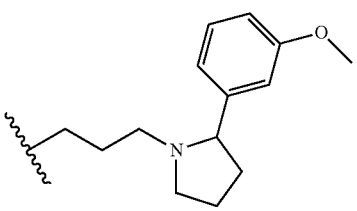 [SMILES: *CCCN1CCCC1c1cccc(OC)c1] | 45 mg | 407<br>389 | White flocculent powder |
| 49 | 1aw |  | 21 mg | 393<br>375 | White flocculent powder |

TABLE 7-continued
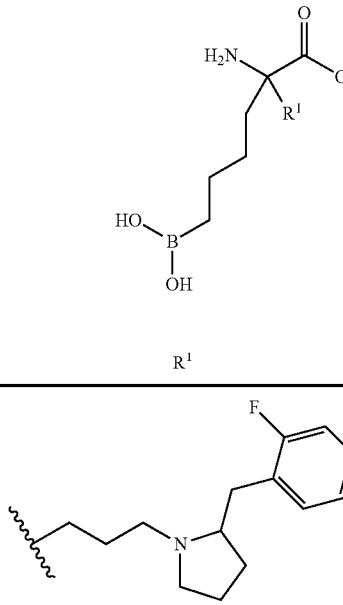
| Example No. | Cmpd No. | R¹ | Amt Isolated | MS Data | Physical Appearance |
|---|---|---|---|---|---|
| 50 | 1ax | 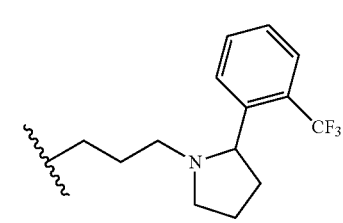 [SMILES: *CCCN1CCCC1c1ccccc1C(F)(F)F] | 42 mg | 395 377 | White flocculent powder |
| 51 | 1ay | 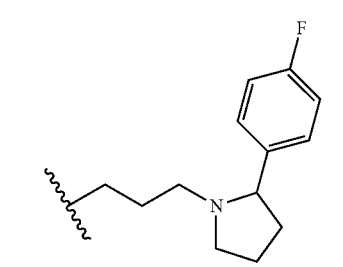 [SMILES: *CCCN1CCCC1c1ccc(F)cc1] | 10 mg | 431 413 | White flocculent powder |
| 52 | 1az | 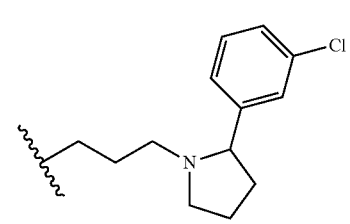 [SMILES: *CCCN1CCCC1c1cccc(Cl)c1] | 7 mg | 381 363 | White flocculent powder |
| 53 | 1ba | | 18 mg | 397 379 | White flocculent powder |
| 54 | 1bb | 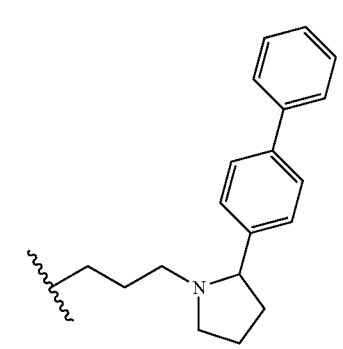 [SMILES: *CCCN1CCCC1c1ccc(-c2ccccc2)cc1] | 17 mg | 439 421 | White flocculent powder |

TABLE 7-continued

| Example No. | Cmpd No. | R¹ | Amt Isolated | MS Data | Physical Appearance |
|---|---|---|---|---|---|
| 55 | 1bc | 3,4-dichlorophenyl-pyrrolidinyl-butyl | 12 mg | 431, 413 | Colorless glass |
| 56 | 1bd | pyrrolidinyl-butyl | 28 mg | 287, 269 | Colorless glass |
| 57 | 1be | azetidinyl-butyl | 6 mg | 273, 255 | Colorless glass |
| 58 | 1bf | 3-phenylazetidinyl-butyl | 7 mg | 349, 331 | Colorless glass |
| 59 | 1bg | 3-(4-methylphenyl)azetidinyl-butyl | 9 mg | 363, 345 | Colorless glass |
| 60 | 1bh | 3-[3-(3,4-dichlorophenyl)ureido]azetidinyl-butyl | 4 mg | 475, 457 | Colorless glass |
| 61 | 1bi | 3-[3-(4-fluorophenyl)ureido]azetidinyl-butyl | 7 mg | 425, 407 | Colorless glass |

TABLE 7-continued
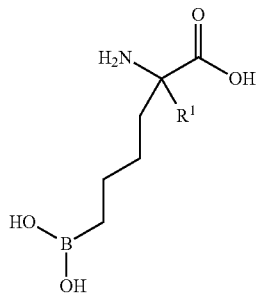
| Example No. | Cmpd No. | R¹ | Amt Isolated | MS Data | Physical Appearance |
|---|---|---|---|---|---|
| 62 | 1bj | 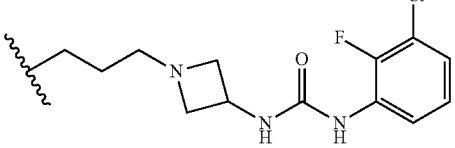 | 2 mg | 444 426 | Colorless glass |
| 63 | 1bk | 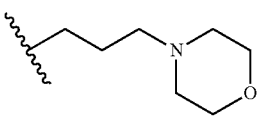 | 30 mg | 330 312 | Colorless glass |
| 64 | 1bl | 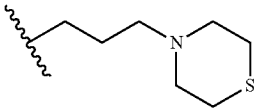 [SMILES: *CCCN1CCSCC1] | 8 mg | 303 285 | Colorless glass |
| 65 | 1bm | 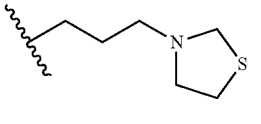 [SMILES: *CCCN1CCSC1] | 4 mg | 319 301 | Colorless glass |
| 66 | 1bn | 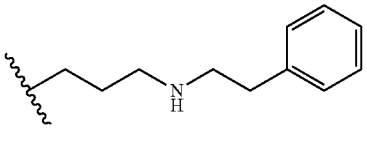 [SMILES: *CCCNCCc1ccccc1] | 20 mg | 349 331 | Colorless glass |
| 67 | 1bo | 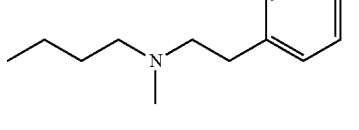 | 15 mg | 337 319 | Colorless glass |
| 68 | 1bp | 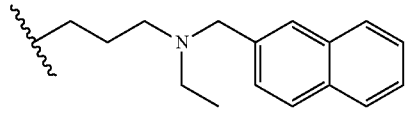 [SMILES: *CCCN(CC)Cc1ccc2ccccc2c1] | 5 mg | 351 333 | Colorless glass |
| 69 | 1bq | 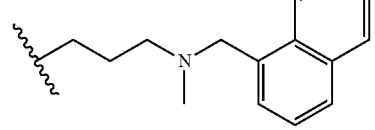 | 20 mg | 401 383 | White powder |
| 70 | 1br |  | 17 mg | 387 369 | Colorless glass |

TABLE 7-continued

| Example No. | Cmpd No. | R¹ | Amt Isolated | MS Data | Physical Appearance |
|---|---|---|---|---|---|
| 71 | 1bs | (butyl-N(ethyl)-CH₂-naphthyl) | 2 mg | 401, 383 | Colorless glass |
| 72 | 1bt | (butyl-N(ethyl)-CH₂-phenyl) | 19 mg | 351, 333 | White powder |
| 73 | 1bu | (propyl-N(methyl)-CH₂-(3-Cl-phenyl)) | 20 mg | 371, 353 | White powder |
| 74 | 1bv | (propyl-N(methyl)-CH₂-(4-Cl-phenyl)) | 6 mg | 371, 353 | Colorless glass |
| 75 | 1bw | (propyl-N(methyl)-CH₂-(3,4-diCl-phenyl)) | 6 mg | 405, 387 | Colorless glass |
| 76 | 1bx | (propyl-N(ethyl)-CH₂-(3,4-diCl-phenyl)) | 2 mg | 419, 401 | White powder |
| 77 | 1by | (propyl-NH-cyclohexyl) | 10 mg | 315, 297 | Colorless glass |
| 78 | 1bz | (propyl-N(methyl)-cyclohexyl) | 26 mg | 329, 311 | Colorless glass |
| 79 | 1ca | (propyl-N(ethyl)-CH₂-cyclohexyl) | 14 mg | 357, 339 | Colorless glass |

TABLE 7-continued
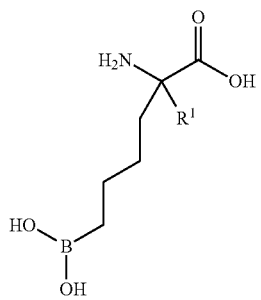
| Example No. | Cmpd No. | R¹ | Amt Isolated | MS Data | Physical Appearance |
|---|---|---|---|---|---|
| 80 | 1cb | 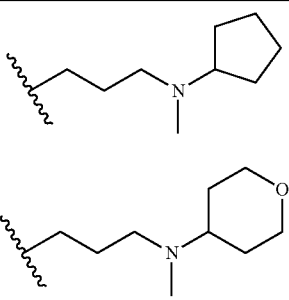 | 20 mg | 315 297 | Colorless glass |
| 81 | 1cc | 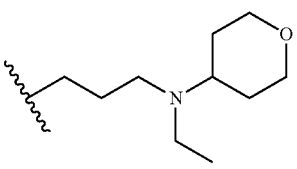 [SMILES: *CCCN(CC)C1CCOCC1] | 8 mg | 331 313 | Colorless glass |
| 82 | 1cd | 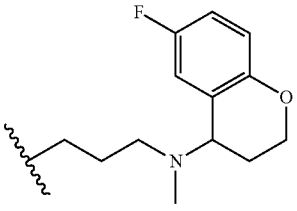 [SMILES: *CCCN(C)C1CCOc2ccc(F)cc21] | 10 mg | 343 325 | Colorless glass |
| 83 | 1ce | 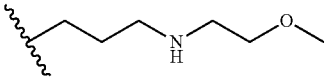 [SMILES: *CCCNCCOC] | 4 mg | 397 379 | Colorless glass |
| 84 | 1cf | 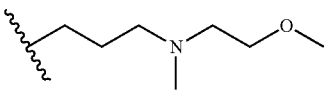 [SMILES: *CCCN(C)CCOC] | 27 mg | 291 273 | Colorless glass |
| 85 | 1cg | | 10 mg | 305 287 | Colorless glass |
| 86 | 1ch | 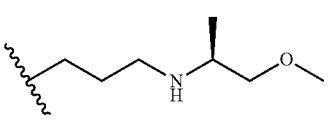 [SMILES: *CCCN[C@@H](C)COC] | 15 mg | 287 269 | Colorless glass |
| 87 | 1ci | 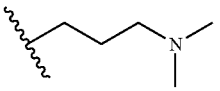 [SMILES: *CCCN(C)C] | 11 mg | 261 243 | Colorless glass |
| 88 | 1cj | 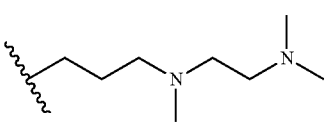 [SMILES: *CCCN(C)CCN(C)C] | 16 mg | 318 300 | Colorless glass |

TABLE 7-continued

| Example No. | Cmpd No. | R¹ | Amt Isolated | MS Data | Physical Appearance |
|---|---|---|---|---|---|
| 89 | 1ck | (CH₂)₃-NH-CH₂CH₂-N(CH₃)₂ | 15 mg | 304, 286 | Colorless glass |
| 90 | 1cl | (CH₂)₄-N(CH₂CH₃)₂ | 9 mg | 271, 253 | Colorless glass |
| 91 | 1cm | (CH₂)₃-(diazabicyclic)-C(O)NH-(3,4-dichlorophenyl) | 6 mg | 501, 483 | Colorless glass |
| 92 | 1cn | piperidinyl-bile acid ester conjugate | 40 mg | 807, 789 | White flocculent powder |
| 93 | 1co | (CH₂)₄-piperazinyl-NH | 8 mg | 316, 298 | Colorless glass |
| 94 | 1cp | (CH₂)₄-N-piperazinyl-N-(3,4-dichlorophenyl) | 58 mg | 460, 442 | White flocculent powder |
| 95 | 1cq | (CH₂)₄-N-piperidinyl-CH₂-(3,4-difluorophenyl) | 49 mg | 441, 423 | White flocculent powder |
| 96 | 1cr | (CH₂)₄-(1,2,3,4-tetrahydroisoquinolin-2-yl) | 29 mg | 363, 345 | White flocculent powder |

TABLE 7-continued

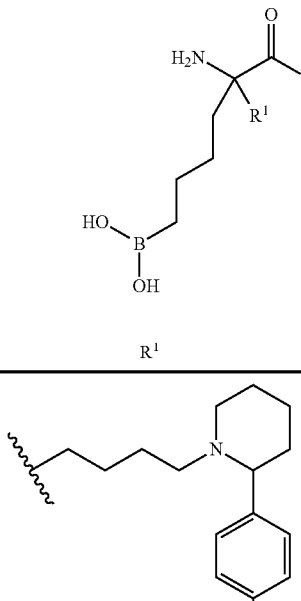

| Example No. | Cmpd No. | R¹ | Amt Isolated | MS Data | Physical Appearance |
|---|---|---|---|---|---|
| 97 | 1cs | 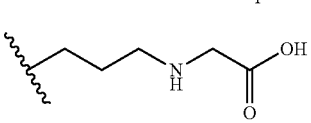 | 41 mg | 409 391 | White flocculent powder |
| 98 | 1ct | 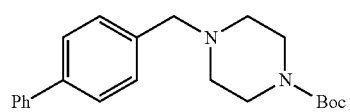 | 7 mg | 381 363 | White flocculent powder |

Example 99

2-amino-2-(3-(4-(biphenyl-4-ylmethyl)piperazin-1-yl)propyl)-6-boronohexanoic acid (1cu)

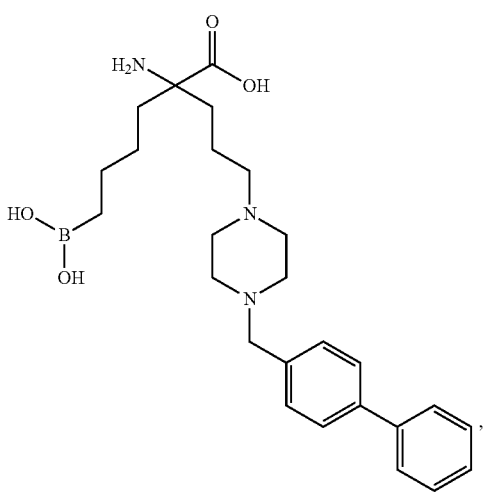

tert-Butyl 4-(biphenyl-4-ylmethyl)piperazine-1-carboxylate (51)

51

0.182 g (1.00 mmol) of biphenyl-4-carbaldehyde and 0.224 g (1.20 mmol) tert-butyl piperazine-1-carboxylate were dissolved in 10 mL dry DCM. 0.35 mL (3.0 mmol) of trimethylorthoformate and 0.21 mL (1.50 mmol) triethylamine were then added to the reaction mixture at room temperature for 1 hr. The reaction was quenched with a solution of NaHCO₃ and diluted with EtOAc. The layers were separated and the aqueous solution extracted with EtOAc 2×. The organic solution was dried over Na₂SO₄, filtered and concentrated in vacuo to give 0.35 g (100%) of 51 which was used as is for the next reaction.

1-(Biphenyl-4-ylmethyl)piperazine (52)

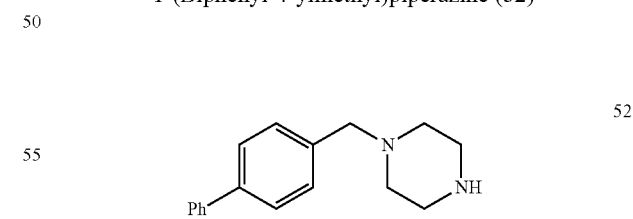

0.35 g (1.0 mmol) of compound 51 was dissolved in 5 mL methanol and 0.5 mL 12 N HCl at room temperature. The mixture was stirred for 20 min and added to a solution of NaHCO₃ and extracted 3× with EtOAc. The organic solution was dried over Na₂SO₄, filtered and concentrated in vacuo to give 0.25 g (100%) of 52.

(E)-tert-Butyl-amino-2-(3-(tert-butyldimethylsilyloxy)propyl)hex-4-enoate (26)

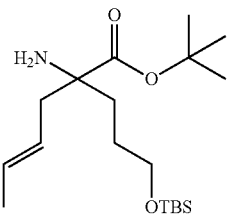

26

12.5 g (81% yield) of compound 26 was obtained as an oil from 40.0 g of compound 25 using the first part of General Procedure J described above. MS (LC/MS, ESI): 358 (M+H), 302 (M–tBu+H). ¹H NMR (300 MHz, CDCl₃, δ): 5.5 (m, 2H), 3.8 (t, 2H), 2.4-2.5 (dd, 2H), 2.05 (d, 3H), 1.6-1.8 (m, 4H), 1.38 (s, 9H), 1.0 (s, 9H), 0.2 (s, 6H).

(E)-tert-Butyl 2-(tert-butoxycarbonylamino)-2-(3-(tert-butyldimethylsilyloxy)propyl)hex-4-enoate (32)

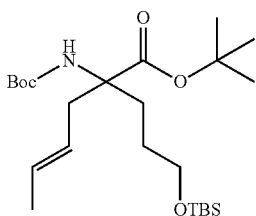

32

15.9 g (99%) of compound 32 was obtained from 12.5 g of compound 26 using General Procedure K described above. MS (LC/MS, ESI): 458, (M+H), 358 (M–Boc+H). ¹H NMR (300 MHz, CDCl₃, δ): 5.5 (m, 2H), 3.8 (t, 2H), 2.4-2.5 (dd, 2H), 2.05 (d, 3H), 1.6-1.8 (m, 4H), 1.4 (s, 9H), 1.38 (s, 9H), 1.0 (s, 9H), 0.2 (s, 6H).

tert-Butyl 2-(tert-butoxycarbonylamino)-2-(3-tert-butyldimethylsilyloxy)propyl)-6-(4,4,5,5-tetramethyl-1,3,2-dioxaborolan-2-yl)hexanoate (33)

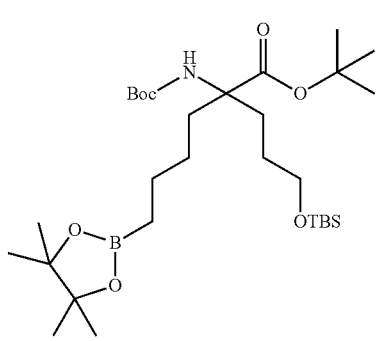

33

15.8 g (78%) of compound 33 was obtained from 15.9 g of compound 32 using General Procedure E described above. MS (LC/MS, ESI): 586, (M+H), 530 (M–tBu+H), ¹H NMR (300 MHz, CDCl₃, δ): 3.8 (t, 2H), 1.5-2.0 (m, 10H), 1.4 (s, 9H), 1.38 (s, 9H), 1.25 (s, 12H), 1.0 (s, 9H), 0.8 (t, 2H), 0.2 (s, 6H).

tert-butyl 2-(tert-butoxy)carbonylamino)-2-(3-iodopropyl-6-(4,4,5,5-tetramethyl-1,3,2-dioxaborolan-2-yl)hexanoate (34)

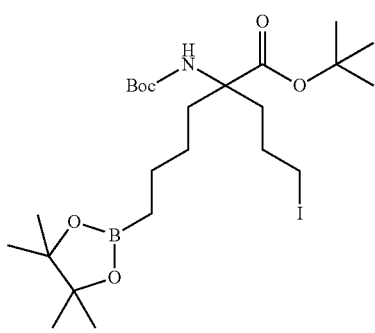

34

3.11 g (55%) of compound 34 was obtained from 5.77 g of compound 33 using General Procedure L described above. MS (LC/MS, ESI): 583, (M+H), 527 (M–tBu+H). ¹H NMR (300 MHz, CDCl₃, δ): 3.2 (t, 2H), 1.5-2.0 (m, 10H), 1.4 (s, 9H), 1.38 (s, 9H), 1.25 (s, 12H), 1.0 (s, 9H), 0.8 (t, 2H), 0.2 (s, 6H).

tert-Butyl 2-(3-(4-(biphenyl-4-ylmethyl)piperazine-1-yl)propyl)-2-(tert-butoxycarbonylamino)-6-(4,4,5,5-tetramethyl-1,3,2-dioxaborolan-2-yl)hexanoate (35cu)

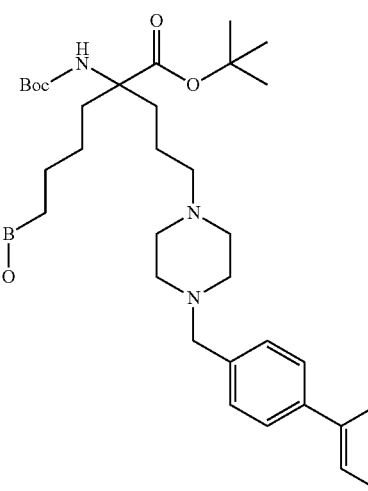

35cu 95 mg (67%) of compound 35cu was obtained from 0.116 g of compound 34 and 0.055 g of compound 52 described above using General Procedure N described above. MS (LC/MS, ESI): 706, (M+H).

Finally, 30 mg of compound 1cu, the structure of which is illustrated above, was obtained using General Procedure O, described above. MS (LC/MS, ESI): 450 (M–H₂O+H). ¹H NMR (500 MHz, D₂O, δ): 7.78 (d, 2H), 7.72 (d, 2H), 7.58 (d, 2H), 7.55 (d, 2H), 7.49 (t, 1H), 4.51 (s, 2H), 3.70 (br, 8H), 3.32 (t, 2H), 1.95-1.76 (m, 6H), 1.42 (m, 3H), 1.23 (m, 1H), 0.79 (t, 2H).

Examples 100-128

The following compounds listed in Table 8, below, were synthesized in analogous manner as described above for compound 1cu. In Table 8, each compound has the following chemical structure (each example in the Table has a different $R^1$ group):

TABLE 8

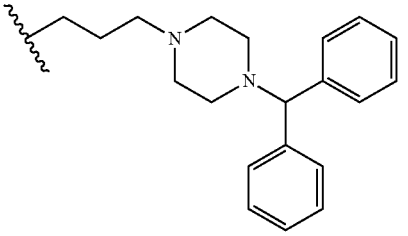 [SMILES: *CCCN1CCN(C(c2ccccc2)c2ccccc2)CC1]

| Example No. | Cmpd No. | $R^1$ | Amt Isolated | MS Data | Physical Appearance |
|---|---|---|---|---|---|
| 100 | 1cv | 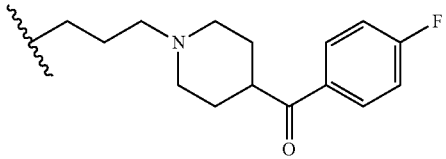 | 15 mg | 468 450 | White flocculent powder |
| 101 | 1cw | 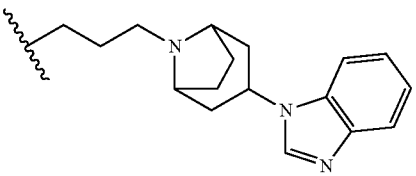 [SMILES: *CCCN1C2CCC1CC(n1cnc3ccccc31)C2] | 35 mg | 423 405 | White flocculent powder |
| 102 | 1cx | 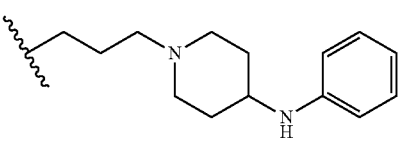 [SMILES: *CCCN1CCC(Nc2ccccc2)CC1] | 86 mg | 443 425 | White flocculent powder |
| 103 | 1cy | | 60 mg | 392 374 | White flocculent powder |
| 104 | 1cz | 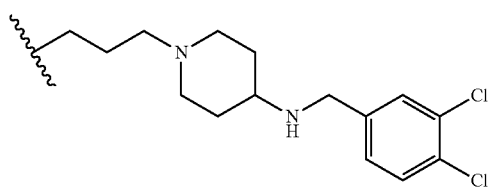 [SMILES: *CCCN1CCC(NCc2ccc(Cl)c(Cl)c2)CC1] | 40 mg | 474 456 | White flocculent powder |

TABLE 8-continued
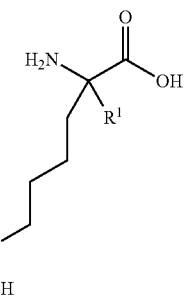
| Example No. | Cmpd No. | R¹ | Amt Isolated | MS Data | Physical Appearance |
|---|---|---|---|---|---|
| 105 | 1da | | 92 mg | 502 484 | White flocculent powder |
| 106 | 1db | | 15 mg | 316 298 | Colorless glass |
| 107 | 1dc | | 12 mg | 395 377 | White powder |
| 108 | 1dd | | 49 mg | 600 582 | White flocculent powder |
| 109 | 1de | | 10 mg | 561 543 | White flocculent powder |
| 110 | 1df | | 5 mg | 418 400 | White flocculent powder |

TABLE 8-continued
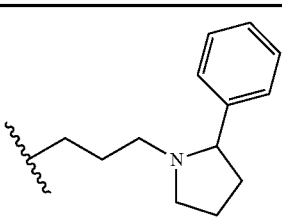
| Example No. | Cmpd No. | R¹ | Amt Isolated | MS Data | Physical Appearance |
|---|---|---|---|---|---|
| 111 | 1dg | 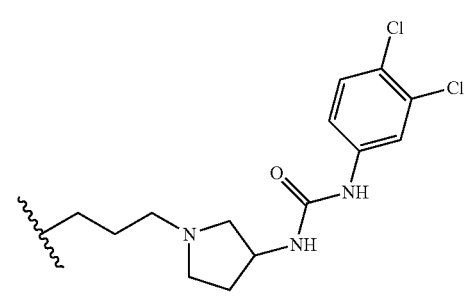 [SMILES: *CCCN1CCC(NC(=O)Nc2ccc(Cl)c(Cl)c2)C1] | 10 mg | 363 345 | Colorless glass |
| 112 | 1dh | 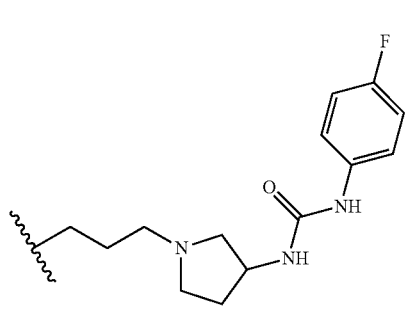 [SMILES: *CCCN1CCC(NC(=O)Nc2ccc(F)cc2)C1] | 5 mg | 489 471 | Colorless glass |
| 113 | 1di | 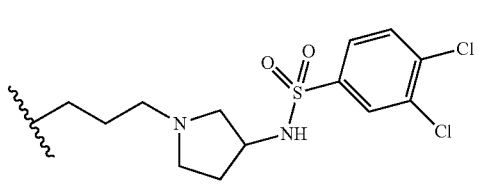 [SMILES: *CCCN1CCC(NS(=O)(=O)c2ccc(Cl)c(Cl)c2)C1] | 10 mg | 439 421 | Colorless glass |
| 114 | 1dj | 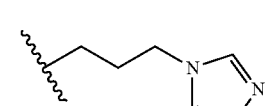 | 13 mg | 510 492 | Colorless glass |
| 115 | 1dk | 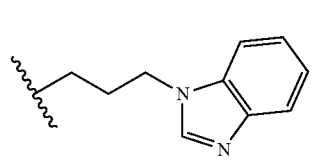 [SMILES: *CCCn1cnc2ccccc21] | 8 mg | 284 266 | Colorless glass |
| 116 | 1dl | | 8 mg | 334 316 | Colorless glass |

TABLE 8-continued
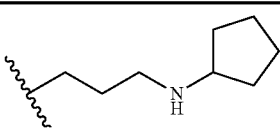
| Example No. | Cmpd No. | R¹ | Amt Isolated | MS Data | Physical Appearance |
|---|---|---|---|---|---|
| 117 | 1dm | 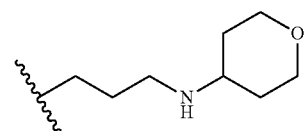 [SMILES: *CCCNC1CCOCC1] | 4 mg | 283 265 | Colorless glass |
| 118 | 1dn | 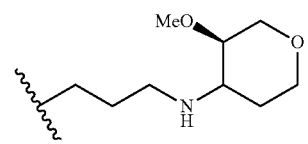 [SMILES: *CCCNC1CCOC[C@@H]1OC] | 6 mg | 317 299 | Colorless glass |
| 119 | 1do | 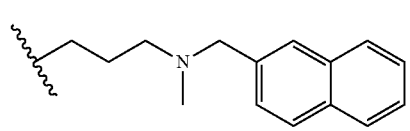 [SMILES: *CCCN(C)Cc1ccc2ccccc2c1] | 2 mg | 347 329 | Colorless glass |
| 120 | 1dp | 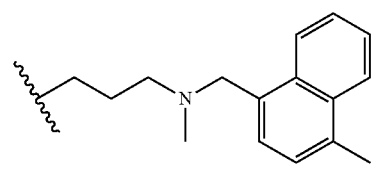 [SMILES: *CCCN(C)Cc1ccc(C)c2ccccc12] | 4 mg | 387 369 | Colorless glass |
| 121 | 1dq | 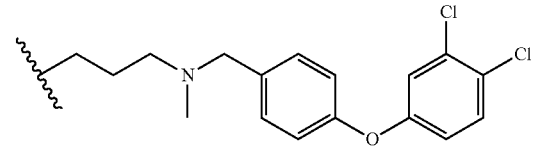 [SMILES: *CCCN(C)Cc1ccc(Oc2ccc(Cl)c(Cl)c2)cc1] | 18 mg | 401 383 | Colorless glass |
| 122 | 1dr | 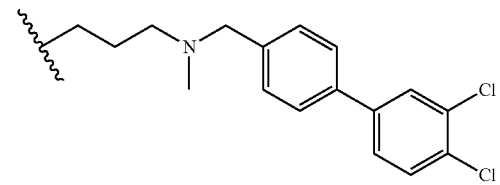 [SMILES: *CCCN(C)Cc1ccc(-c2ccc(Cl)c(Cl)c2)cc1] | 12 mg | 497 479 | White powder |
| 123 | 1ds | 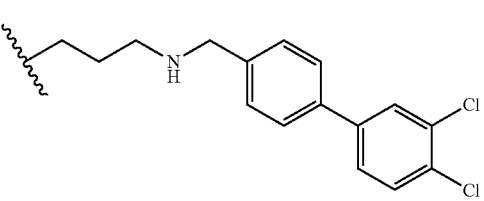 [SMILES: *CCCNCc1ccc(-c2ccc(Cl)c(Cl)c2)cc1] | 5 mg | 481 463 | Colorless glass |
| 124 | 1dt | | 4 mg | 467 449 | Colorless glass |

TABLE 8-continued

| Example No. | Cmpd No. | R¹ | Amt Isolated | MS Data | Physical Appearance |
|---|---|---|---|---|---|
| 125 | 1du | | 11 mg | 305 287 | Colorless glass |
| 126 | 1dv | | 8 mg | 345 327 309 | Colorless glass |
| 127 | 1dw | | 10 mg | 319 301 | White powder |
| 128 | 1dx | | 12 mg | 361 343 | Colorless glass |

Example 129

2-amino-6-borono-(3-(4-(3,4-dichlorobenzoyl)piperazine-1-yl)propyl)hexanoic acid (1dy)

tert-Butyl 2-(3-(4-(3,4-dichlorobenzoyl)piperazine-1-yl)propyl)-2-(diphenylmethylene amino)-6-(4,4,5,5-tetramethyl-1,3,2-dioxaborolan-2yl)hexanoate (17dy)

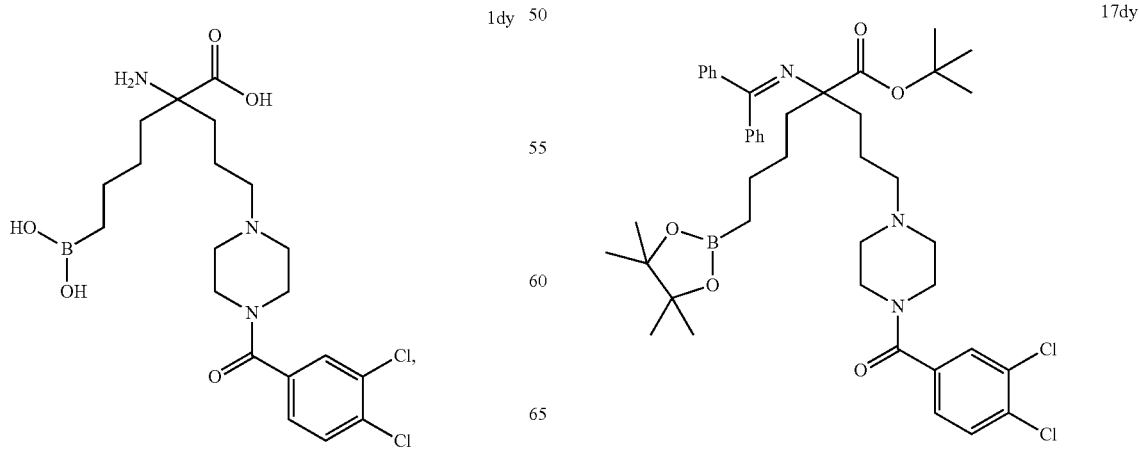

Compound 17dy, 85 mg was obtained using General Procedure H described above. MS (LC/MS, ESI): 776 (M+H).

Finally, 19 mg of compound 1dy, the structure of which is illustrated above, was obtained using General Procedure O, described above, MS (LC/MS, ESI): 456 (M–H$_2$O+H). $^1$H NMR (300 MHz, D$_2$O, δ): 8.1 (s, 1H), 7.9 (d, 1H), 7.6 (d, 1H), 3.4-3.5 (m, 4H), 2.4-2.5 (m, 6H), 2.0 (m, 6H), 1.3 (m, 4H), 0.8 (t, 2H).

Alternatively, compound 1dy may be prepared by the following procedure:

tert-Butyl 4-(4-(benzyloxycarbonylamino)-4-(tert-butoxycarbonyl)-8-(4,4,5,5-5-tetramethyl-1, 3-2-dioxaborolan-2-yl)octyl)piperazine-1-carboxylate (19)

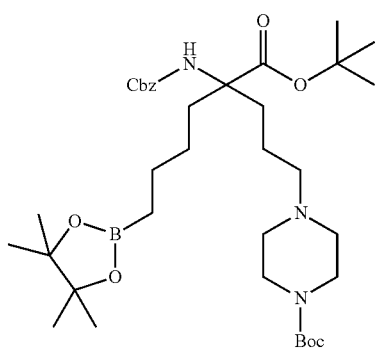

Compound 19, 319 mg was obtained using General Procedure I described above. MS (LC/MS, ESI): 674 (M+H). $^1$H NMR (300 MHz, CDCl$_3$, δ): 7.4 (s, 5H), 59 (bs, 1H), 5.1 (s, 2H), 3.2-3.6 (m, 8H), 2.2-2.3 (m, 2H), 1.7-1.9 (m, 6H), 1.4 (s, 18H), 1.3-1.5 (m, 4H), 1.25 (s, 12H), 0.7 (t, 2H).

tert-Butyl 2-(benzyloxycarbonylamino)-2-(3-piperazin-1-yl)propyl)-6-(4,4,5,5-tetramethyl-1,3,2-dioxaborolan-2-yl)hexanoate (20)

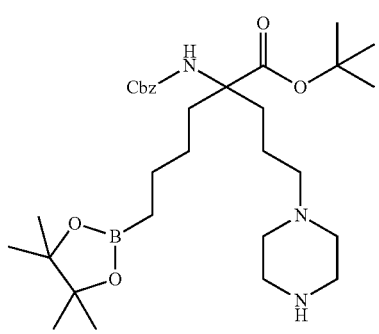

Compound 20, 82 mg was obtained using General Procedure F described above. MS (LC/MS, ESI): 574 (M+H).

tert-Butyl 2-(benzyloxycarbonylamino)-2-(3-(4-(3,4-dichlorobenzoyl)piperazin-1-yl)propyl)-6-(4,4,5,5-tetramethyl-1,3,2-dioxaborolan-2-yl)hexanoate (22dy)

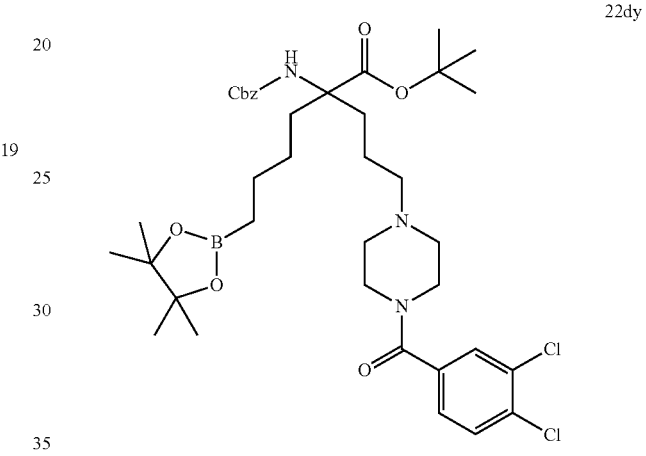

Compound 22dy, 90 mg was obtained using General Procedure H described above. MS (LC/MS, ESI): 746 (M+H).

Finally, 9 mg of compound 1dy, the structure of which is illustrated above, was obtained using General Procedure Q, described above. MS (LC/MS, ESI): 456 (M–H$_2$O+H). $^1$H NMR (300 MHz, D$_2$O, δ): 8.1 (s, 1H), 7.9 (d, 1H), 7.6 (d, 1H), 3.4-3.5 (m, 4H), 2.4-2.5 (m, 6H), 2.0 (m, 6H), 1.3 (m, 4H), 0.8 (t, 2H).

Examples 131-154

The following compounds listed in Table 9, below, were synthesized in analogous manner as described above for compound 1dy. In Table 9, each compound has the following chemical structure (each example in the Table has a different R$^1$ group):

TABLE 9
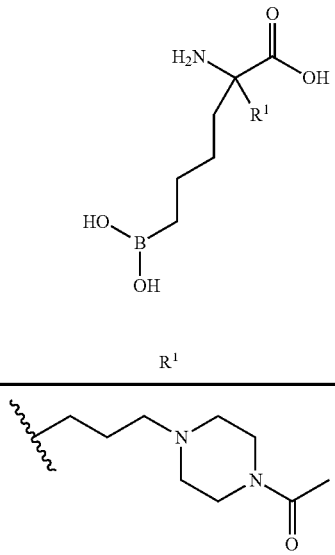
| Example No. | Cpmd No. | R¹ | Amt isolated | MS Data | Physical Appearance |
|---|---|---|---|---|---|
| Comparative Example 5 | 1dz | 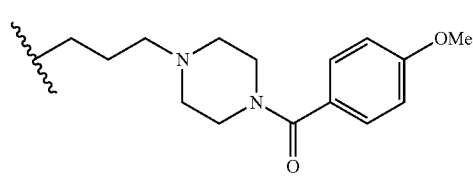 [SMILES: *CCCN1CCN(C(=O)c2ccc(OC)cc2)CC1] | 6 mg | 326 | Colorless glass |
| 131 | 1ea | 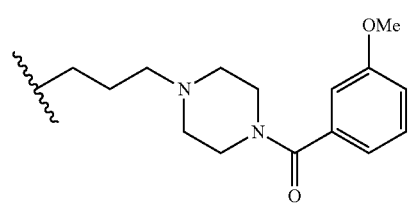 [SMILES: *CCCN1CCN(C(=O)c2cccc(OC)c2)CC1] | 12 mg | 418 | Colorless glass |
| 132 | 1eb | 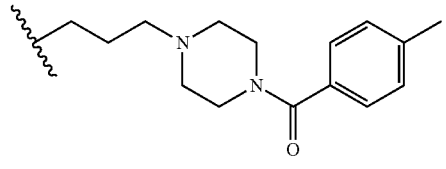 [SMILES: *CCCN1CCN(C(=O)c2ccc(C)cc2)CC1] | 40 mg | 418 | Colorless glass |
| 133 | 1ec | 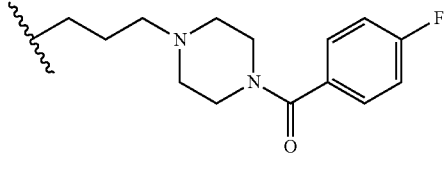 [SMILES: *CCCN1CCN(C(=O)c2ccc(F)cc2)CC1] | 20 mg | 420 | Colorless glass |
| 134 | 1ed | 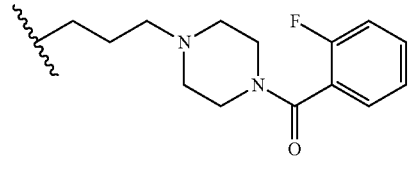 [SMILES: *CCCN1CCN(C(=O)c2ccccc2F)CC1] | 20 mg | 424 406 | Colorless glass |
| 135 | 1ee | 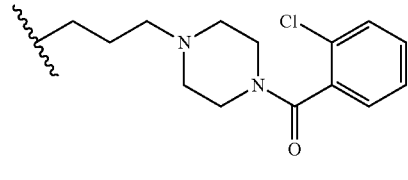 [SMILES: *CCCN1CCN(C(=O)c2ccccc2Cl)CC1] | 18 mg | 406 | Colorless glass |
| 136 | 1ef | | 20 mg | 422 | Colorless glass |

TABLE 9-continued

[Structure: 2-amino-6-borono-2-R¹-hexanoic acid core with H₂N, COOH, R¹ substituent, and B(OH)₂ group]

| Example No. | Cpmd No. | R¹ | Amt isolated | MS Data | Physical Appearance |
|---|---|---|---|---|---|
| 137 | 1eg | [piperazine-N-C(O)-phenyl-3-F] | 26 mg | 406 | Colorless glass |
| 138 | 1eh | [piperazine-N-C(O)-phenyl-4-CF₃] | 6 mg | 474, 456 | Colorless glass |
| Comparative Example 6 | 1ei | [piperazine-N-C(O)-phenyl-4-CN] | 6 mg | 413 | Colorless glass |
| 140 | 1ej | [piperazine-N-C(O)-phenyl-4-C(O)NH₂] | 6 mg | 431 | White flocculent powder |
| Comparative Example 7 | 1ek | [piperazine-N-C(O)-NH-phenyl-3-OMe] | 7 mg | 433 | Colorless glass |
| 142 | 1el | [piperazine-N-C(O)-NH-phenyl-3,4-diCl] | 18 mg | 471 | Colorless glass |

TABLE 9-continued

| Example No. | Cpmd No. | R¹ | Amt isolated | MS Data | Physical Appearance |
|---|---|---|---|---|---|
| 143 | 1em | piperazine-butyl linker, N-C(O)-NH-(2-F-phenyl) | 14 mg | 439, 421 | Colorless glass |
| 144 | 1en | piperazine-butyl linker, N-C(O)-NH-(3-F-phenyl) | 2 mg | 439, 421 | Colorless glass |
| 145 | 1eo | piperazine-butyl linker, N-C(O)-NH-(4-F-phenyl) | 25 mg | 421 | Colorless glass |
| 146 | 1ep | piperazine-butyl linker, N-C(O)-NH-(3,4-diF-phenyl) | 10 mg | 439 | Colorless glass |
| 147 | 1eq | piperazine-butyl linker, N-C(O)-NH-(2,5-diF-phenyl) | 10 mg | 439 | Colorless glass |
| 148 | 1er | piperazine-butyl linker, N-C(O)-NH-(2,4-diF-phenyl) | 6 mg | 457, 439 | Colorless glass |

TABLE 9-continued

| Example No. | Cpmd No. | R¹ | Amt isolated | MS Data | Physical Appearance |
|---|---|---|---|---|---|
| 149 | 1es | (piperazine-butyl linked to urea-NH-2,3-difluorophenyl) | 4 mg | 457, 439 | Colorless glass |
| 150 | 1et | (piperazine-butyl linked to urea-NH-3,5-difluorophenyl) | 5 mg | 457, 439 | Colorless glass |
| 151 | 1eu | (piperazine-butyl linked to sulfonyl-4-methylphenyl) | 12 mg | 438 | Colorless glass |
| 152 | 1ev | (piperazine-butyl linked to sulfonyl-4-fluorophenyl) | 15 mg | 442 | Colorless glass |
| 153 | 1ew | (piperazine-butyl linked to sulfonyl-3-fluorophenyl) | 19 mg | 460, 442 | Colorless glass |
| 154 | 1ex | (piperazine-butyl linked to sulfonyl-3,4-dichlorophenyl) | 6 mg | 492 | Colorless glass |

The following compounds listed in Table 10, below, were synthesized via General Procedure R, S, T, or U described above. The protecting groups intact after these reactions were removed via General Procedure Q described above. In Table 10, each compound has the following chemical structure (each example in the Table has a different $R^2$ group):

TABLE 10

| Example No. | Cmpd No. | $R^2$ | Amt Isolated | MS Data | Physical Appearance |
|---|---|---|---|---|---|
| 155 | 42a | isobutyl | 160 mg | 502.2 | White powder |
| 156 | 42b | isohexyl | 14 mg | 530.3 | White powder |
| 157 | 42c | propyl-piperidine | 65 mg | 571.35 | White powder |
| 158 | 42d | propyl-morpholine | 10 mg | 573.3 | White powder |

The following compounds listed in Table 11, below, were synthesized via General Procedure R, S, T, or U described above. The protecting groups intact after these reactions were removed via General Procedure Q described above. In Table 11, each compound has the following chemical structure (each example in the Table has a different $R^2$ group):

TABLE 11

| Example No. | Cmpd No. | $R^2$ | Amt Isolated | MS Data | Physical Appearance |
|---|---|---|---|---|---|
| 159 | 42e | Me | 13 mg | 483.3 | White powder |
| 160 | 42f | Et | 23 mg | 498.0 | White powder |
| 161 | 42g | Pr | 16 mg | 512.2 | Colorless glass |
| 162 | 42h | isobutyl | 9 mg | 527.9 | White powder |
| 163 | 42i | isopentyl | 86 mg | 526.3 | White powder |
| 164 | 42j | isohexyl | 8 mg | 540.3 | Colorless glass |
| 165 | 42k | 2-ethylbutyl | 7 mg | 539.8 | White powder |
| 166 | 42l | 2,3-dimethylbutyl | 7 mg | 540.0 | White powder |
| 167 | 42m | methoxypropyl | 16 mg | 527.9 | White powder |
| 168 | 42n | hydroxypropyl | 44 mg | 514.2 | Colorless glass |
| 169 | 42o | propyl-morpholine | 15 mg | 565.3 | Colorless glass |

Example 170

5-amino-8-(4-(3,4-dichlorophenyl)piperazine-1-yl)-
5-(methoxycarbonyl)octylboronic acid (42p)

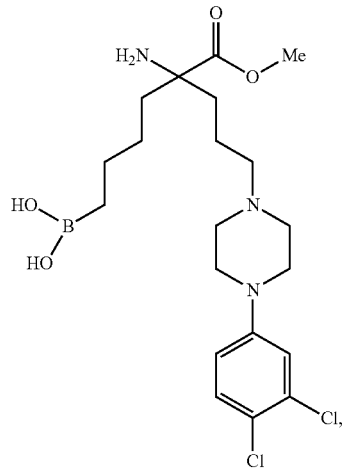

tert-Butyl 2-(benzyloxycarbonylamino)-2-(3-(4-(3,4-
dichlorophenyl)piperazin-1-yl)propyl-6-(4,4,5,5-
tetramethyl-1,3,2-dioxaborolan-2-yl)hexanoate (53)

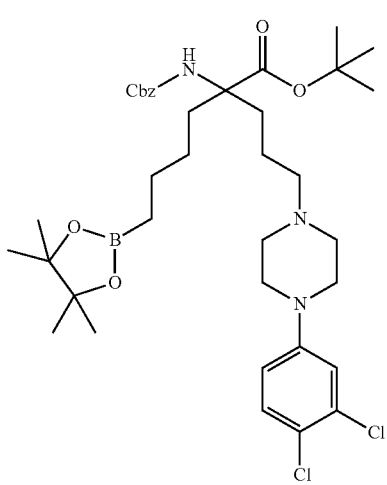

Compound 53, 1.277 g (53%), was obtained by using General Procedure N described above. MS (LC/MS, ESI): 718 (M+H), 662 (M−tBu+H). $^1$H NMR (300 MHz, CDCl$_3$, δ): 7.4 (s, 5H), 6.8-7.2 (m, 3H), 5.9 (bs, 1H), 5.1 (s, 2H), 3.2-3.6 (m, 8H), 2.4-2.5 (m, 4H), 1.6-2.0 (m, 8H), 1.4 (s, 9H), 1.25 (s, 12H), 0.8 (t, 2H).

2-benzyloxycarbonylamino)-2-(3-(4-(3,4-dichlo-
rophenyl)piperazin-1-yl)propyl)-6-(4,4,5,5-tetram-
ethyl-1,3,2-dioxaborolan-2-yl)hexanoic acid (54)

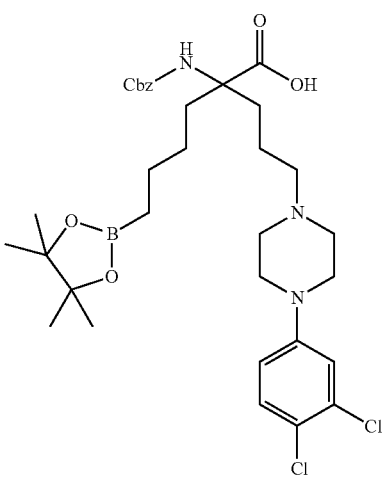

Compound 51 was treated with 100% TFA at room temperature for 2 hr. The reaction mixture was concentrated in vacuo and the residue washed with DCM 3× by the addition of a few mL of DCM and removal of the volatiles to a puddle. The residue, compound 52, 0.125 g (100%), was used as is for the next reaction. MS (LC/MS, ESI): 662 (M+H).

Methyl 2-(benzyloxycarbonylamino)-2-(3-4-(3,4-
dichlorophenyl)piperazin-1-yl)propyl)-6-(4,4,5,5-
tetramethyl-1,3,2-dioxaborolan-2-yl)hexanoate (55)

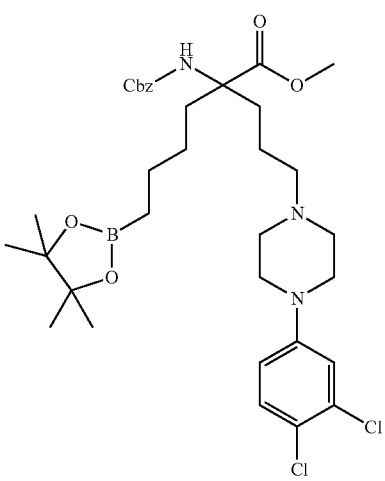

Compound 54 (0.11 g, 0.163 mmols) was dissolved in 5 mL dry toluene/methanol 1:1 under argon. TMS diazomethane in ether was added dropwise with stirring at room temperature until a yellow solution was formed (0.4 mL total, 0.8 mmol) and the mixture stirred for an additional 30 min. Glacial acetic acid was added dropwise until the yellow color disappeared and the reaction mixture concentrated in vacuo. This residue was eluted over a silica gel column with mixtures of EtOAc/hexanes (20-50%) to give 90 mg (80%) of compound 55 as an oil, MS (LC/MS, ESI): 718 (M+H), 662 (M−tBu+H). $^1$H NMR (300 MHz, CDCl$_3$, δ): 7.4 (s, 5H), 6.8-7.2 (m, 3H), 5.9 (bs, 1H), 5.1 (s, 2H), 3.8 (s, 3H), 3.2-3.6 (m, 8H), 2.4-2.5 (m, 4H), 1.6-2.0 (m, 8H), 1.25 (s, 12H), 0.8 (t, 2H).

Finally, 25 mg of compound 42p, the structure of which is illustrated above, was obtained using General Procedure V. MS (LC/MS, ESI): 460 (M+H).

Table 12 illustrates a non-limiting selection of the compounds of the invention.

TABLE 12

| Example No. | Name |
|---|---|
| Comparative Example 4 | 2-amino-6-borono-2-(3-(piperazin-1-yl)propylhexanoic acid |
| 2 | 2-amino-6-borono-2-(2-(piperazin-1-yl)ethyl)hexanoic acid |
| 3 | 2-amino-2-(3-(4-benzylpiperazin-1-yl)propyl)-6-boronohexanoic acid |
| 4 | 2-amino-6-borono-2-(3-(4-(2-chlorobenzyl)piperazin-1-yl)propyl)hexanoic acid |
| 5 | 2-amino-6-borono-2-(3-(4-(2-cyanobenzyl)piperazin-1-yl)propyl)hexanoic acid |
| 6 | 2-amino-6-borono-2-(3-(4-(2,4-difluorobenzyl)piperazin-1-yl)propyl)hexanoic acid |
| 7 | 2-amino-6-borono-2-(3-(4-(2,3-difluorobenzyl)piperazin-1-yl)propyl)hexanoic acid |
| 8 | 2-amino-6-borono-2-(3-(4-(3,4-dichlorobenzyl)piperazin-1-yl)hexanoic acid |
| 9 | 2-amino-6-borono-2-(3-(4-(3-(trifluoromethyl)benzyl)piperazin-1-yl)propyl)hexanoic acid |
| 10 | 2-amino-6-borono-2-(3-(4-(4-(methylsulfonyl)benzyl)piperazin-1-yl)propyl)hexanoic acid |
| 11 | 2-amino-6-borono-2-(3-(4-(4-fluorobenzyl)piperazin-1-yl)propyl)hexanoic acid |
| 12 | 2-amino-6-borono-2-(3-(4-(3,4-difluorobenzyl)piperazin-1-yl)propyl)hexanoic acid |
| 13 | 2-amino-6-borono-2-(3-(4-(3,5-difluorobenzyl)piperazin-1-yl)propyl)hexanoic acid |
| 14 | 2-amino-6-borono-2-(3-(4-phenethylpiperazin-1-yl)propyl)hexanoic acid |
| 15 | 2-amino-6-borono-2-(2-(4-(3,4-dichlorobenzyl)piperazin-1-yl)ethyl)hexanoic acid |
| 16 | 2-amino-6-borono-2-(3-(4-(3,4-dichlorophenyl)piperazin-1yl)propyl)hexanoic acid |
| 17 | 2-amino-6-borono-2-(3-(2-(4-fluorophenyl)piperidin-1-yl)propyl)hexanoic acid |
| 18 | 2-amino-6-borono-2-(2-(piperidin-2-yl)ethyl)hexanoic acid |
| 19 | 2-amino-6-borono-2-(2-(1-(3,4-dichlorobenzyl)piperidin-2-yl)ethyl)hexanoic acid |
| 20 | 2-amino-6-borono-2-(2-(1-(3,5-difluorobenzyl)piperidin-2-yl)ethyl)hexanoic acid |
| 21 | 2-amino-6-borono-2-(2-(1-(3,4-difluorobenzyl)piperidin-2-yl)ethyl)hexanoic acid |
| 22 | 2-amino-6-borono-2-(2-(1-(3,4-dichlorobenzyl)piperidin-3-yl)ethyl)hexanoic acid |
| 23 | 2-amino-6-borono-2-(3-(1-(3,4-dichlorobenzyl)piperidin-2-yl)propyl)hexanoic acid |
| 24 | 2-amino-6-borono-2-(3-(1-(3,4-difluorobenzyl)piperidin-2-yl)propyl)hexanoic acid |
| 25 | 2-amino-6-borono-2-(3-(1-(3,5-difluorobenzyl)piperidin-2-yl)propyl)hexanoic acid |
| 26 | 2-amino-6-borono-2-(3-(3-phenylpiperidin-1-yl)propyl)hexanoic acid |
| 27 | 2-amino-6-borono-2-(3-(3-(5-fluoro-1H-benzo[d]imidazol-2-yl)piperidin-1-yl)propyl)hexanoic acid |
| 28 | 2-amino-6-borono-2-(3-(4-(3,4-difluorobenzyl)piperidin-1-yl)propyl)hexanoic acid |
| 29 | 2-amino-6-borono-2-(3-(4-(pyrimidin-2-ylmethyl)piperidin-1-yl)propyl)hexanoic acid |
| 30 | 2-(3-(3H-spiro[isobenzofuran-1,4'piperidine]-1'-yl)propyl)-2-amino-6-boronohexanoic acid |
| 31 | 2-amino-6-borono-2(3-(4-oxo-1-phenyl-1,3,8-triazaspiro[4.5]decan-8-yl)propylhexanoic acid |
| 32 | 2-amino-6-borono-2-(3-(4-(2-chlorophenyl)-1H-pyrazol-1-yl)piperidin-1-yl)propylhexanoic acid |
| 33 | 2-amino-6-borono-2-(3-(4-(5-phenyl-1,3,4-oxadiazol-2-yl)piperidin-1-yl)propyl)hexanoic acid |
| 34 | 2-amino-6-borono-2-(3-(4-(4-(trifluoromethyl)phenoxy)piperidin-1-yl)propyl)hexanoic acid |
| 35 | 2-amino-6-borono-2-(3-(4-(2-isopropylphenoxy)piperidin-1-yl)propyl)hexanoic acid |
| 36 | 2-amino-6-borono-2-(3-(4-(4-fluorophenyl)piperidin-1-yl)propylhexanoic acid |
| 37 | 2-amino-6-borono-2-(3-(4-(4-methoxyphenyl)piperidin-1-yl)propyl)hexanoic acid |

TABLE 12-continued

| Example No. | Name |
|---|---|
| 38 | 2-amino-6-borono-2-(3-(4-(4-chlorophenyl)-5,6-dihydropyridin-1(2H)-yl)propyl)hexanoic acid |
| 39 | 2-amino-2-(3-(4-benzyl-4-hydroxypiperidin-1-yl)propyl)-6-boronohexanoic acid |
| 40 | 2-amino-6-borono-2-(3-(4-(4-chlorophenyl)-4-hydroxypiperidin-1-yl)propyl)hexanoic acid |
| 41 | 2-amino-6-borono-2-(3-(4-(5-(trifluoromethyl)pyridin-2-yl)piperazin-1-yl)propyl)hexanoic acid |
| 42 | 2-amino-6-borono-2-(3-(4-hydroxypiperidin-1-yl)propyl)hexanoic acid |
| 43 | 2-amino-2-(3-(4-((S)-2-amino-3-methylbutanoyloxy)piperidin-1-yl)propyl)-6-boronohexanoic acid |
| 44 | 2-amino-2-(3-(4-benzamidopiperidin-1-yl)propyl)-6-boronohexanoic acid |
| 45 | 2-amino-6-borono-2-(3-(3,4-dihydroisoquinolin-2(1H)-yl)propyl)hexanoic acid |
| 46 | 2-amino-6-borono-2-(3-(4-methyl-2-phenylpiperazin-1-yl)propyl)hexanoic acid |
| 47 | 2-amino-2-(3-(2-benzylpiperidin-1-yl)propyl)-6-boronohexanoic acid |
| 48 | 2-amino-6-borono-2-(3-(2-(4-methoxyphenyl)piperidin-1-yl)propyl)hexanoic acid |
| 49 | 2-amino-6-borono-2-(3-(2-(3-methoxylphenyl)pyrrolidin-1-yl)propyl)hexanoic acid |
| 50 | 2-amino-6-borono-2-(3-(2-(2-fluorobenzyl)pyrrolidin-1-yl)propyl)hexanoic acid |
| 51 | 2-amino-6-borono-2-(3-(2-(2-(trifluoromethyl)phenyl)pyrrolidin-1-yl)propyl)hexanoic acid |
| 52 | 2-amino-6-borono-2-(3-(2-(4-fluorophenyl)pyrrolidin-1-yl)propyl)hexanoic acid |
| 53 | 2-amino-6-borono-2-(3-(2-(3-chlorophenyl)pyrrolidin-1-yl)propyl)hexanoic acid |
| 54 | 2-amino-2-(3-(2-(biphenyl-4-yl)pyrrolidin-1-yl)propyl)-6-borono-hexanoic acid |
| 55 | 2-amino-6-borono-2-(3-(2-(3,4-dichlorophenyl)pyrrolidin-1-yl)propyl)hexanoic acid |
| 56 | 2-amino-6-borono-2-(3-(pyrrolidin-1-yl)propyl)hexanoic acid |
| 57 | 2-amino-2-(3-(azetidin-1-yl)propyl)-6-boronohexanoic acid |
| 58 | 2-amino-6-borono-2-(3-(3-phenylazetidin-1-yl)propyl)hexanoic acid |
| 59 | 2-amino-6-borono-2-(3-(3-p-tolylazetidin-1-yl)propyl)hexanoic acid |
| 60 | 2-amino-6-borono-2-(3-(3-(3-(3,4-dichlorophenyl)ureido)azetidin-1-yl)propyl)hexanoic acid |
| 61 | 2-amino-6-borono-2-(3-(3-(3-(4-fluorophenyl)ureido)azetidin-1-yl)propyl)hexanoic acid |
| 62 | 2-amino-6-borono-2-(3-(3-(-chloro-2-fluorobenzamido)azetidin-1-yl)propyl)hexanoic acid |
| 63 | 2-amino-6-borono-2-(3-(4-ethylpiperazin-1-yl)propyl)hexanoic acid |
| 64 | 2-amino-6-borono-2-(3-morpholinopropyl)hexanoic acid |
| 65 | 2-amino-6-borono-2-(3-thiomorpholinopropyl)hexanoic acid |
| 66 | 2-amino-6-borono-2-(3-(thiazolidin-2-yl)propyl)hexanoic acid |
| 67 | 2-amino-6-borono-2-(3-(phenethylamino)propyl)hexanoic acid |
| 68 | 2-amino-6-boron-2-(3-(methyl(phenethyl)aminopropyl)hexanoic acid |
| 69 | 2-amino-6-borono-2-(3-(ethyl(naphthalen-1-ylmethyl)amino)propyl)hexanoic acid |
| 70 | 2-amino-6-borono-2-(3-(methyl(naphthalen-1-ylmethyl)amino)propyl)hexanoic acid |
| 71 | 2-amino-6-borono-2-(3-((cyclohexylmethyl)(ethyl)amino)propyl)hexanoic acid |
| 72 | 2-amino-2-(3-(benzyl(ethyl)amino)propyl)-6-boronohexanoic acid |
| 73 | 2-amino-2-(3-(benzyl(ethyl)amino)propyl)-6-boronohexanoic acid |
| 74 | 2-amino-6-borono-2-(3-((4-chlorobenzyl)(methyl)amino)propyl)hexanoic acid |
| 75 | 2-amino-6-borono-2-(3-((3,4-dichlorobenzyl)(methyl)amino)propyl)hexanoic acid |
| 76 | 2-amino-6-borono-2-(3-((3,4-dichlorobenzyl)(ethyl)amino)propyl)hexanoic acid |
| 77 | 2-amino-6-borono-2-(3-(cyclohexylamino)propyl)hexanoic acid |
| 78 | 2-amino-6-borono-2-(3-(cyclohexyl(methyl)amino)propyl)hexanoic acid |
| 79 | 2-amino-6-borono-2-(3-(methyl(tetrahydro-2H-pyran-4-yl)amino)propyl)hexanoic acid |
| 80 | 2-amino-6-borono-2-(3-(cyclopentyl(methyl)amino)propyl)hexanoic acid |
| 81 | 2-amino-6-borono-2-(3-((3-chlorobenzyl)(methyl)amino)propyl)hexanoic acid |
| 82 | 2-amino-6-borono-2-(3-(ethyl(tetrahydro-2H-pyran-4-yl)amino)propyl)hexanoic acid |
| 83 | 2-amino-6-borono-2-(3-((6-fluorochroman-4-yl)(methyl)amino)propyl)hexanoic acid |
| 84 | 2-amino-6-borono-2-(3-(2-methoxyethylamino)propyl)hexanoic acid |

TABLE 12-continued

| Example No. | Name |
|---|---|
| 85 | 2-amino-6-borono-2-(3-((2-methoxyethyl)(methyl)amino)propyl)hexanoic acid |
| 86 | 2-amino-6-borono-2-(3-((S)-1-methoxypropan-2-ylamino)propyl)hexanoic acid |
| 87 | 2-amino-6-borono-2-(3-(dimethylamino)propyl)hexanoic acid |
| 88 | 2-amino-6-borono-2-(3-((2-(dimethylamino)ethyl(methyl)amino)propyl)hexanoic acid |
| 89 | 2-amino-6-borono-2-(3-(2-(dimethylamino)ethylamino)propyl)hexanoic acid |
| 90 | 2-amino-6-borono-2-(3-(diethylamino)propyl)hexanoic acid |
| 91 | 2-amino-6-borono-2-(3-((1R,4R)-5-(3,4-dichlorophenylcarbamoyl)-2,5-diazabicyclo[2.2.2]heptan-2-yl)propyl)hexanoic acid |
| 92 | 2-amino-6-borono-2-(3-(4-((S)-3-methyl-2-((R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanamido)butanoyloxy)piperidin-1-yl)propyl)hexanoic acid |
| 93 | 2-amino-6-borono-2-(4-(piperazin-1-yl)butyl)hexanoic acid |
| 94 | 2-amino-6-borono-2-(4-(4-(3,4-dichlorophenyl)piperazin-1-yl)butyl)hexanoic acid |
| 95 | 2-amino-6-borono-2-(4-(4-(3,4-difluorobenzyl)piperidin-1-yl)butyl)hexanoic acid |
| 96 | 2-amino-6-borono-2-(4-(3,4-dihydroisoquinolin-2(1H)-yl)butyl)hexanoic acid |
| 97 | 2-amino-6-borono-2-(4-(2-(4-fluorophenyl)piperidin-1-yl)butyl)hexanoic acid |
| 98 | 2-amino-6-borono-2-(3-(carboxymethylamino)propyl)hexanoic acid |
| 99 | 2-amino-2-(3-(4-(biphenyl-4-ylmethyl)piperazin-1-yl)propyl-6-boronohexanoic acid |
| 100 | 2-amino-2-(3-(4-benzhydrylpiperazin-1-yl)propyl)-6-boronohexanoic acid |
| 101 | 2-amino-6-borono-2-(3-(4-(4-fluorobenzoyl)piperidin-1-yl)propyl)hexanoic acid |
| 102 | 2-(3-(3-(1H-benzo[d]imidazol-1-yl)-8-azabicyclo[3.2.1]octan-8-yl)propyl)-2-amino-6-boronohexanoic acid |
| 103 | 2-amino-6-borono-2(3-(4-(phenylamino)piperidin-1-yl)propyl)hexanoic acid |
| 104 | 2-amino-6-borono-2-(3-(4-(3,4-dichlorobenzylamino)piperidin-1-yl)propyl)hexanoic acid |
| 105 | 2-amino-6-borono-2-(3-(4-((3,4-dichlorobenzyl)(ethyl)amino)piperidin-1-yl)propyl)hexanoic acid |
| 106 | 2-amino-6-borono-2-(3-(4-methylpiperazin-1-yl)propyl)hexanoic acid |
| 107 | 2-amino-6-borono-2-(3-(3-fluoro-4-phenylpiperidin-1-yl)propyl)hexanoic acid |
| 108 | 2-amino-6-borono-2-(3-(4-(N-(3,4-dichlorobenzyl)octanamido)piperidin-1-yl)propyl)hexanoic acid |
| 109 | 2-amino-3-(3-(4-benzyl-4-(decanoyloxy)piperidin-1-yl)propyl)-6-boronohexanoic acid |
| 110 | 2-amino-2-(3-(3-(benzo[d]oxazol-2-yl)piperidin-1-yl)propyl)-6-boronohexanoic acid |
| 111 | 2-amino-6-borono-2-(3-(2-phenylpyrrolin-1-yl)propyl)hexanoic acid |
| 112 | 2-amino-6-borono-2-(3-(3-(3,4-dichlorophenyl)ureido)pyrrolidin-1-yl)propyl)hexanoic acid |
| 113 | 2-amino-6-borono-2-(3-(3-(3-(4-fluorophenyl)ureido)pyrrolidin-1-yl)propyl)hexanoic acid |
| 114 | 2-amino-6-borono-2-(3-(3-(3,4-dichlorophenylsulfonamido)pyrrolidin-1-yl)propyl)hexanoic acid |
| 115 | 2-(3-(1H-imidazol-1-yl)propyl-2-amino-6-boronohexanoic acid |
| 116 | 2-(3-(1H-benzo[d]imidazol-1-yl)propyl)-2-amino-6-boronohexanoic acid |
| 117 | 2-amino-6-borono-2-(3-(cyclopentylamino)propyl)hexanoic acid |
| 118 | 2-amino-6-borono-2-(3-(tetrahydro-2H-pyran-4-ylamino)propyl)hexanoic acid |
| 119 | 2-amino-6-borono-2-(3-((3R)-3-methoxytetrahydro-2H-pyran-4-ylamino)propyl)hexanoic acid |
| 120 | 2-amino-6-borono-2-(3-(methyl(naphthalen-2-ylmethyl)amino)propyl)hexanoic acid |
| 121 | 2-amino-6-borono-2-(3-(methyl((4-methylnaphthalen-1-yl)methyl)amino)propyl)hexanoic acid |
| 122 | 2-amino-6-borono-2-(3-((4-(3,4-dichlorophenoxy)benzyl)(methyl)amino)propyl)hexanoic acid |
| 123 | 2-amino-6-borono-2-(3-(((3',4'-dichlorobiphenyl-4-yl)methyl)(methyl)amino)propyl)hexanoic acid |
| 124 | 2-amino-6-borono-2-(3-((3',4'-dichlorobiphenyl)-4-yl)methylamino)propyl)hexanoic acid |
| 125 | (S)-2-amino-6-borono-2-(3-(1-carboxyethylamino)propyl)hexanoic acid |
| 126 | (S)-2-amino-6-borono-2-(3-(1-carboxy-3-methylbutylamino)propyl)hexanoic acid |

TABLE 12-continued

| Example No. | Name |
|---|---|
| 127 | 2-amino-6-borono-2-(3-((S)-1-methoxy-1-oxopropan-2-ylamino)propyl)hexanoic acid |
| 128 | (S)-2-amino-6-borono-2-(3-(1-methoxy-4-methyl-1-oxopentan-2-ylamino)propyl)hexanoic acid |
| 129 | 2-amino-6-borono-2-(3-(4-(3,4-dichlorobenzoyl)piperazin-1-yl)propyl)hexanoic acid |
| Comparative Example 5 | 2-(3-(4-acetylpiperazin-1-yl)propyl)-2-amino-6-boronohexanoic acid |
| 131 | 2-amino-6-borono-2-(3-(4-(4-methoxybenzoyl)piperazin-1-yl)propyl)hexanoic acid |
| 132 | 2-amino-6-borono-2-(3-(4-(3-methoxybenzoyl)piperazin-1-yl)propyl)hexanoic acid |
| 133 | 2-amino-6-borono-2-(3-(4-(4-methylbenzoyl)piperazin-1-yl)propyl)hexanoic acid |
| 134 | 2-amino-6-borono-2-(3-(4-(4-fluorobenzoyl)piperazin-1yl)propyl)hexanoic acid |
| 135 | 2-amino-6-borono-2-(3-(4-(2-fluorobenzoyl)piperazin-1-yl)propyl)hexanoic acid |
| 136 | 2-amino-6-borono-2-(3-(4-(2-chlorobenzoyl)piperazin-1-yl)propyl)hexanoic acid |
| 137 | 2-amino-6-borono-2-(3-(4-(3-fluorobenzoyl)piperazin-1-yl)propyl)hexanoic acid |
| 138 | 2-amino-6-borono-2-(3-(4-(4-(trifluoromethyl)benzoyl)piperazin-1-yl)propyl)hexanoic acid |
| Comparative Example 6 | 2-amino-6-borono-2-(3-(4-(4-cyanobenzoyl)piperazin-1-yl)propylhexanoic acid |
| 140 | 2-amino-6-borono-2-(3-(4-(4-carbamoylbenzoyl)piperazin-1-yl)propyl)hexanoic acid |
| Comparative Example 7 | 2-amino-6-borono-2-(3-(4-(3-methoxyphenylcarbamoyl)piperazin-1-yl)propyl)hexanoic acid |
| 142 | 2-amino-6-borono-2-(3-(4-(3,4-dichlorophenylcarbamoyl)piperazin-1-yl)propyl)hexanoic acid |
| 143 | 2-amino-6-borono-2-(3-(4-(2-fluorophenylcarbamoyl)piperazin-1-yl)propyl)hexanoic acid |
| 144 | 2-amino-6-borono-2-(3-(4-(3-fluorophenylcarbamoyl)piperazin-1-yl)propyl)hexanoic acid |
| 145 | 2-amino-6-borono-2-(3-(4-(4-fluorophenylcarbamoyl)piperazin-1-yl)propyl)hexanoic acid |
| 146 | 2-amino-6-borono-2-(3-(4-(3,4-diflurorophenylcarbamoyl)piperazin-1-yl)propylhexanoic acid |
| 147 | 2-amino-6-borono-2-(3-(4-(2,5-difluorophenylcarbamoyl)piperazin-1-yl)propyl)hexanoic acid |
| 148 | 2-amino-6-borono-2-(3-(4-(2,4-difluorophenylcarbamoyl)piperazin-1-yl)propyl)hexanoic acid |
| 149 | 2-amino-6-borono-2-(3-(4-(2,3-difluorophenylcarbamoyl)piperazin-1-yl)propyl)hexanoic acid |
| 150 | 2-amino-6-borono-2-(3-(4-(3,5-difluorophenylcarbamoyl)piperazin-1-yl)propyl)hexanoic acid |
| 151 | 2-amino-6-borono-2-(3-(4-tosylpiperazin-1-yl)propyl)hexanoic acid |
| 152 | 2-amino-6-borono-2-(3-(4-(4-fluorophenylsulfonyl)piperazin-1-yl)propyl)hexanoic acid |
| 153 | 2-amino-6-borono-2-(3-(4-(3-fluorophenylsulfonyl)piperazin-1-yl)propyl)hexanoic acid |
| 154 | 2-amino-6-borono-2-(3-(4-(3,4-dichlorophenylsulfonyl)piperazin-1-yl)propyl)hexanoic acid |
| 155 | 5-amino-8-(4-(3,4-dichlorobenzyl)piperazin-1-yl)-5-(isopropoxycarbonyl)octylboronic acid |
| 156 | 5-amino-8-(4-(3,4-dichlorobenzyl)piperazin-1-yl)-5-(isopentyloxycarbonyl)octylboronic acid |
| 157 | 5-amino-8-(4-(3,4-dichlorobenzyl)piperazin-1-yl)-5-((2-(piperidin-1-yl)ethoxy)carbonyl)octylboronic acid |
| 158 | 5-amino-8-(4-(3,4-dichlorobenzyl)piperazin-1-yl)-5-((2-morpholinoethoxy)carbonyl)octylboronic acid |
| 159 | 5-amino-5-(methoxycarbonyl)-8-(4-(4-methylsulfonyl)benzyl)piperazin-1-yl)octylboronic acid |
| 160 | 5-amino-5-(ethoxycarbonyl)-8-(4-(4-(methylsulfonyl)benzyl)piperazin-1-yl)octylboronic acid |
| 161 | 5-amino-8-(4-(4-(methylsulfonyl)benzyl)piperazine-1-yl)-5-(propoxycarbonyl)octylboronic acid |
| 162 | 5-amino-5-(isopropoxycarbonyl)-8-(4-(4-(methylsulfonyl)benzyl)piperazin-1-yl)octylboronic acid |
| 163 | 5-amino-5-(isobutoxycarbonyl)-8-(4-(4-(methylsulfonyl)benzyl)piperazin-1-yl)octylboronic acid |
| 164 | 5-amino-5-(isopentyloxycarbonyl)-8-(4-(4-(methylsulfonyl)benzyl)piperazin-1-yl)octylboronic acid |
| 165 | 5-amino-8-(4-(4-(methylsulfonyl)benzyl)piperazin-1-yl)-5-((pentan-3-yloxy)carbonyl)octylboronic acid |

TABLE 12-continued

| Example No. | Name |
|---|---|
| 166 | 5-amino-5-((3-methylbutan-2-yloxy)carbonyl)-8-(4-(4-(methylsulfonyl)benzylpiperazin-1-yl)octylboronic acid |
| 167 | 5-amino-5-((2-methoxyethoxy)carbonyl)-8-(4-(4-(methylsulfonyl)benzyl)piperazin-1-yl)octylboronic acid |
| 168 | 5-amino-5-((2-hydroxyethoxy)carbonyl)-8-(4-(4-(methylsulfonyl)benzyl)piperazin-1-yl)octylboronic acid |
| 169 | 5-amino-8-(4-(4-(methylsulfonyl)benzyl)piperazine-1-yl-5-((2-morpholinoethoxy)carbonyl)octylboronic acid |
| 170 | 5-amino-8-(4-(3,4-dichlorophenyl)piperazin-1-yl-5-(methoxycarbonyl)octylboronic acid |

Example 171 pH Effect of Compounds of the Invention

The inhibitory potency of selected compounds of the invention against Arg I and/or Arg II was determined at pH values of 7.5 and 9.5. In one embodiment, compounds were found to have a 'pH effect' as defined herein if the potency ratio at pH 7.5 over pH 9.5 was at least 0.5. For some compounds, their inhibitory potency at pH 7.5 was compared to the inhibitory potency of ABH at pH 7.5. Selected data are displayed on Table 3.

Example 172

Biological Assay of Arginase Inhibition

Quantitative determination of arginase activity was performed in a 96-well format by a colorimetric method using the QuantiChrom™ Arginase Assay Kit available from Bio-Assay Systems (Hayward, Calif., Catalog No. DARG-200) according to the manufacturer's protocol. Modifications were made to reagent quantities to suit the assaying of a highly purified sample.

Briefly, the method utilized a chromogen that forms a colored complex specifically with urea produced in the arginase reaction (Mellerup, 1967, Clin. Chem. 13:900-08). The intensity of the color was directly proportional to the arginase activity in the sample.

The rate of urea production was measured in the presence of twelve different concentrations of each potential inhibitor compound. In a typical assay, seven different compounds were tested relative to a control inhibitor (e.g. ABH) against one enzyme (either human ArgI or human ArgII) at a particular pH (either 9.5 or 7.5). The pH of the solution was controlled using an appropriate pH buffering compound at 60 mM concentrations; for example, 60 mM glycine (pH 9.5) or 60 mM HEPES (pH 7.5). The half maximal inhibitory concentration ($IC_{50}$) was determined by constructing a dose-response curve. As $IC_{50}$ values are dependent upon the measurement conditions, the $IC_{50}$ values were converted to the inhibitor binding affinity ($K_i$) using the Cheng-Prusoff equation and the affinity constant ($K_m$) of L-arginine which was estimated with the same activity assay (see, e.g., Cheng et al., 1973, Biochem. Pharmacol. 22:3099-108).

The inhibitor binding affinities for both human arginase I and II ("hArgI" and "hArgII," respectively) are listed below in Table 1 elsewhere herein.

Example 173

Myocardial Ischemia-Reperfusion Injury

Rats were intraperitoneally (IP) anesthetized to effect with pentobarbital (~50 mg/kg), shaved and positioned in dorsal recumbence, intubated and ventilated (~90 breaths/min, ~2.5 mL tidal volume with 95% $O_2$/5% $CO_2$) with an adjustable small animal ventilator (Harvard Apparatus). Anesthesia was maintained with a continuous sodium pentobarbital infusion (to effect, ~3 to 5 mg/kg/h, IV) until completion of the study via an indwelling catheter placed in a peripheral vein (e.g., femoral). Body temperature was continuously monitored throughout the duration of the surgical/experimental procedures via a rectal probe, and was maintained within the physiological range via a heated temperature-controlled (closed-loop) small animal surgical table/control unit (Vestavia Scientific).

Subsequently, transthoracic needle electrodes forming a single-lead ECG (e.g., lead II) were placed. Once a surgical plane of anesthesia had been reached, a femoral artery was isolated, dissected free from the surrounding tissue, and cannulated with a 2F high-fidelity micromanometer catheter (Millar Instruments). In order to record arterial/systemic pressures, this catheter was advanced towards the abdominal aorta. An in-dwelling catheter was also placed in a vein (i.e., jugular) for administration of the test article/vehicle, or stains (see below).

Finally, the animals were placed in right-lateral recumbence and the heart was exposed by a left-side thoracotomy/pericardiotomy. Ligatures were loosely placed (using a taper-point needle) around the proximal section of the left anterior descending artery (LAD). Tightening of these snares (via small pieces of polyethylene tubing) rendered a portion of myocardium temporarily ischemic.

Following surgical preparation, the animals were allowed to reach hemodynamic stability (for approximately 15 min), and baseline data was collected. It should be noted that in order to ensure experimental/data homogeneity, all animals must have satisfied the following entry criteria: heart rate >320 bpm and mean arterial pressure >80 mmHg. The anesthetic regime may be adjusted in order to ensure proper anesthesia/analgesia and to satisfy such inclusion criteria.

After hemodynamic stabilization and baseline measurements, the animals were treated with either vehicle or test article delivered as an intravenous bolus. Subsequently (approximately 15 min post-dosing), the animals were subjected to an acute 30 min ischemic insult by tightening of the LAD coronary artery snare. Myocardial ischemia was visually confirmed both by the appearance of cyanotic changes in distal distributions of the LAD as well as by the onset of electrocardiographic changes. After approximately 30 min of induced ischemia, the coronary snares were released and the previously ischemic myocardium was reperfused for up to 2 hrs. Treatments were not administered during either the ischemia and/or reperfusion periods. It should also be noted that in order to minimize any possible confounding effects on indices of myocardial injury, non-self-resolving malignant arrhythmias/rhythms (e.g., ventricular tachycardia/fibrillation) developing during reperfusion were considered terminal (i.e., the experiment was terminated prematurely).

At the completion of the protocol, irreversible myocardial injury (i.e., infarction) resulting from the I/R insult was evaluated. In short, the coronary snares were retightened and Evan's blue dye (1 mL/kg; Sigma, St. Louis, Mo.) was injected intravenously to delineate the myocardial area-at-risk (AR) during ischemia. Thereafter, the heart was quickly removed, rinsed in cold saline, weighed, wrapped in Saran wrap and placed in the freezer for approximately 30 minutes. The heart was removed from the freezer, weighed again and transversely sectioned; 2 to 3 short axis segments (~1.5 mm thick) from the apex to the base is taken. The slices were numbered consecutively, with "Slice #1" being the most apical and photographed/scanned. Subsequently, the slices were incubated for approximately 15 minutes in 1% triphenyl-tetrazolium-chloride (TTC) at approximately 37° C. and fixed in a 10% neutral buffered formalin solution for approximately 60 minutes.

Following fixation, the infarct and at-risks areas were delineated and measured digitally. For such purpose, the thickness of each slice was measured with a micrometer and later photographed/scanned. All photographs were imported into an image analysis program (Image J; National Institutes of Health), and computer-assisted planimetry was performed to determine the overall size of the infarct (IA) and the area-at-risk (AR). For each slide, the infarct size (IA, not stained tissue) was expressed as a percentage of the AR (IA/AR). It should be noted that, in all cases, quantitative histomorphometery was performed by personnel blinded to the treatment assignment/study-design. Results are summarized in Table 13.

TABLE 13

| Test Article | Dose, mg/kg iv | Mean IA/AR (%) |
| --- | --- | --- |
| Vehicle for 8 | 0 | 46 |
| Example 8 | 1 | 32 |
|  | 3 | 29 |
| Vehicle for 10 | 0 | 36 |
| Example 10 | 1 | 24 |
|  | 3 | 22 |
|  | 10 | 17 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of:
2-amino-6-borono-2-(2-(piperazin-1-yl)ethyl)hexanoic acid;
2-amino-2-(3-(4-benzylpiperazin-1-yl)propyl)-6-boronohexanoic acid;
2-amino-6-borono-2-(3-(4-(2-chlorobenzyl)piperazin-1-yl)propyl)hexanoic acid;
2-amino-6-borono-2-(3-(4-(2-cyanobenzyl)piperazin-1-yl)propyl)hexanoic acid;
2-amino-6-borono-2-(3-(4-(2,4-difluorobenzyl)piperazin-1-yl)propyl)hexanoic acid;
2-amino-6-borono-2-(3-(4-(2,3-difluorobenzyl)piperazin-1-yl)propyl)hexanoic acid;
2-amino-6-borono-2-(3-(4-(3,4-dichlorobenzyl)piperazin-1-yl)hexanoic acid;
2-amino-6-borono-2-(3-(4-(3-(trifluoromethyl)benzyl)piperazin-1-yl)propyl)hexanoic acid;
2-amino-6-borono-2-(3-(4-(4-(methylsulfonyl)benzyl)piperazin-1-yl)propyl)hexanoic acid;
2-amino-6-borono-2-(3-(4-(4-fluorobenzyl)piperazin-1-yl)propyl)hexanoic acid;
2-amino-6-borono-2-(3-(4-(3,4-difluorobenzyl)piperazin-1-yl)propyl)hexanoic acid;
2-amino-6-borono-2-(3-(4-(3,5-difluorobenzyl)piperazin-1-yl)propyl)hexanoic acid;
2-amino-6-borono-2-(3-(4-phenethylpiperazin-1-yl)propyl)hexanoic acid;
2-amino-6-borono-2-(2-(4-(3,4-dichlorobenzyl)piperazin-1-yl)ethyl)hexanoic acid;
2-amino-6-borono-2-(3-(4-(3,4-dichlorophenyl)piperazin-1yl)propyl)hexanoic acid;
2-amino-6-borono-2-(3-(2-(4-fluorophenyl)piperidin-1-yl)propyl)hexanoic acid;
2-amino-6-borono-2-(2-(piperidin-2-yl)ethyl)hexanoic acid;
2-amino-6-borono-2-(2-(1-(3,4-dichlorobenzyl)piperidin-2-yl)ethyl)hexanoic acid;
2-amino-6-borono-2-(2-(1-(3,5-difluorobenzyl)piperidin-2-yl)ethyl)hexanoic acid;
2-amino-6-borono-2-(2-(1-(3,4-difluorobenzyl)piperidin-2-yl)ethyl)hexanoic acid;
2-amino-6-borono-2-(2-(1-(3,4-dichlorobenzyl)piperidin-3-yl)ethyl)hexanoic acid;
2-amino-6-borono-2-(3-(1-(3,4-dichlorobenzyl)piperidin-2-yl)propyl)hexanoic acid;
2-amino-6-borono-2-(3-(1-(3,4-difluorobenzyl)piperidin-2-yl)propyl)hexanoic acid;
2-amino-6-borono-2-(3-(1-(3,5-difluorobenzyl)piperidin-2-yl)propyl)hexanoic acid;
2-amino-6-borono-2-(3-(3-phenylpiperidin-1-yl)propyl) hexanoic acid;
2-amino-6-borono-2-(3-(3-(5-fluoro-1H-benzo[d]imidazol-2-yl)piperidin-1-yl)propyl)hexanoic acid;
2-amino-6-borono-2-(3-(4-(3,4-difluorobenzyl)piperidin-1-yl)propyl)hexanoic acid;
2-amino-6-borono-2-(3-(4-(pyrimidin-2-ylmethyl)piperidin-1-yl)propyl)hexanoic acid;
2-(3-(3H-spiro[isobenzofuran-1,4'piperidine]-1'-yl)propyl)-2-amino-6-boronohexanoic acid;
2-amino-6-borono-2(3-(4-oxo-1-phenyl-1,3,8-triazaspiro[4.5]decan-8-yl)propyl) hexanoic acid;
2-amino-6-borono-2-(3-(4-(2-chlorophenyl)-1H-pyrazol-1-yl)piperidin-1-yl) propylhexanoic acid;
2-amino-6-borono-2-(3-(4-(5-phenyl-1,3,4-oxadiazol-2-yl)piperidin-1-yl)propyl) hexanoic acid;
2-amino-6-borono-2-(3-(4-(4-(trifluoromethyl)phenoxy)piperidin-1-yl)propyl) hexanoic acid;
2-amino-6-borono-2-(3-(4-(2-isopropylphenoxy)piperidin-1-yl)propyl)hexanoic acid;
2-amino-6-borono-2-(3-(4-(4-fluorophenyl)piperidin-1-yl)propylhexanoic acid;
2-amino-6-borono-2-(3-(4-(4-methoxyphenyl)piperidin-1-yl)propyl)hexanoic acid;
2-amino-6-borono-2-(3-(4-(4-chlorophenyl)-5,6-dihydropyridin-1(2H)-yl)propyl) hexanoic acid;
2-amino-2-(3-(4-benzyl-4-hydroxypiperidin-1-yl)propyl)-6-boronohexanoic acid;

2-amino-6-borono-2-(3-(4-(4-chlorophenyl)-4-hydroxypiperidin-1-yl)propyl)hexanoic acid;
2-amino-6-borono-2-(3-(4-(5-(trifluoromethyl)pyridin-2-yl)piperazin-1-yl)propyl) hexanoic acid;
2-amino-6-borono-2-(3-(4-hydroxypiperidin-1-yl)propyl) hexanoic acid;
2-amino-2-(3-(4-((S)-2-amino-3-methylbutanoyloxy)piperidin-1-yl)propyl)-6-boronohexanoic acid;
2-amino-2-(3-(4-benzamidopiperidin-1-yl)propyl)-6-boronohexanoic acid;
2-amino-6-borono-2-(3-(3,4-dihydroisoquinolin-2(1H)-yl)propyl)hexanoic acid;
2-amino-6-borono-2-(3-(4-methyl-2-phenylpiperazin-1-yl)propyl)hexanoic acid;
2-amino-2-(3-(2-benzylpiperidin-1-yl)propyl)-6-borono-hexanoic acid;
2-amino-6-borono-2-(3-(2-(4-methoxyphenyl)piperidin-1-yl)propyl)hexanoic acid;
2-amino-6-borono-2-(3-(2-(3-methoxylphenyl)pyrrolidin-1l-yl)propyl)hexanoic acid 2-amino-6-borono-2-(3-(2-(2-fluorobenzyl)pyrrolidin-1-yl)propyl)hexanoic acid;
2-amino-6-borono-2-(3-(2-(2-(trifluoromethyl)phenyl)pyrrolidin-1-yl)propyl) hexanoic acid;
2-amino-6-borono-2-(3-(2-(4-fluorophenyl)pyrrolidin-1-yl)propyl)hexanoic acid;
2-amino-6-borono-2-(3-(2-(3-chlorophenyl)pyrrolidin-1-yl)propyl)hexanoic acid;
2-amino-2-(3-(2-(biphenyl-4-yl)pyrrolidin-1-yl)propyl)-6-borono-hexanoic acid;
2-amino-6-borono-2-(3-(2-(3,4-dichlorophenyl)pyrrolidin-1-yl)propyl)hexanoic acid;
2-amino-6-borono-2-(3-(pyrrolidin-1-yl)propyl)hexanoic acid;
2-amino-2-(3-(azetidin-1-yl)propyl)-6-boronohexanoic acid;
2-amino-6-borono-2-(3-(3-phenylazetidin-1-yl)propyl) hexanoic acid;
2-amino-6-borono-2-(3-(3-p-tolylazetidin-1-yl)propyl) hexanoic acid;
2-amino-6-borono-2-(3-(3-(3-(3,4-dichlorophenyl)ureido)azetidin-1-yl)propyl) hexanoic acid;
2-amino-6-borono-2-(3-(3-(3-(4-fluorophenyl)ureido) azetidin-1-yl)propyl) hexanoic acid;
2-amino-6-borono-2-(3-(-chloro-2-fluorobenzamido) azetidin-1-yl)propyl) hexanoic acid;
2-amino-6-borono-2-(3-(4-ethylpiperazin-1-yl)propyl) hexanoic acid;
2-amino-6-borono-2-(3-morpholinopropyl)hexanoic acid;
2-amino-6-borono-2-(3-thiomorpholinopropyl)hexanoic acid;
2-amino-6-borono-2-(3-(thiazolidin-2-yl)propyl)hexanoic acid;
2-amino-6-borono-2-(3-(phenethylamino)propyl)hexanoic acid;
2-amino-6-borono-2-(3-(methyl(phenethyl)aminopropyl) hexanoic acid;
2-amino-6-borono-2-(3-(ethyl(naphthalen-1-ylmethyl) amino)propyl)hexanoic acid;
2-amino-6-borono-2-(3-(methyl(naphthalen-1-ylmethyl) amino)propyl)hexanoic acid;
2-amino-6-borono-2-(3-((cyclohexylmethyl)(ethyl) amino)propyl)hexanoic acid;
2-amino-2-(3-(benzyl(ethyl)amino)propyl)-6-boronohexanoic acid;
2-amino-2-(3-(benzyl(ethyl)amino)propyl)-6-boronohexanoic acid;
2-amino-6-borono-2-(3-((4-chlorobenzyl)(methyl)amino) propyl)hexanoic acid;
2-amino-6-borono-2-(3-((3,4-dichlorobenzyl)(methyl) amino)propyl)hexanoic acid;
2-amino-6-borono-2-(3-((3,4-dichlorobenzyl)(ethyl) amino)propyl)hexanoic acid;
2-amino-6-borono-2-(3-(cyclohexylamino)propyl)hexanoic acid;
2-amino-6-borono-2-(3-(cyclohexyl(methyl)amino)propyl)hexanoic acid;
2-amino-6-borono-2-(3-(methyl(tetrahydro-2H-pyran-4-yl)amino)propyl) hexanoic acid;
2-amino-6-borono-2-(3-(cyclopentyl(methyl)amino)propyl)hexanoic acid;
2-amino-6-borono-2-(3-((3-chlorobenzyl)(methyl)amino) propyl)hexanoic acid;
2-amino-6-borono-2-(3-(ethyl(tetrahydro-2H-pyran-4-yl) amino)propyl)hexanoic acid;
2-amino-6-borono-2-(3-((6-fluorochroman-4-yl)(methyl) amino)propyl)hexanoic acid;
2-amino-6-borono-2-(3-(2-methoxyethylamino)propyl) hexanoic acid;
2-amino-6-borono-2-(3-((2-methoxyethyl)(methyl) amino)propyl)hexanoic acid;
2-amino-6-borono-2-(3-((S)-1-methoxypropan-2-ylamino)propyl)hexanoic acid;
2-amino-6-borono-2-(3-(dimethylamino)propyl)hexanoic acid;
2-amino-6-borono-2-(3-((2-(dimethylamino)ethyl(methyl)amino)propyl)hexanoic acid;
2-amino-6-borono-2-(3-(2-(dimethylamino)ethylamino) propyl)hexanoic acid;
2-amino-6-borono-2-(3-(diethylamino)propyl)hexanoic acid;
2-amino-6-borono-2-(3-((1R,4R)-5-(3,4-dichlorophenylcarbamoyl)-2,5-diazabicyclo[2.2.2]heptan-2-yl)propyl)hexanoic acid;
2-amino-6-borono-2-(3-(4-((S)-3-methyl-2-4((R)-4-((3R,5S,7R,8R,9S,10S,12S,13R,14S,17R)-3,7,12-trihydroxy-10,13-dimethylhexadecahydro-1H-cyclopenta [α]phenathren-17-yl)pentanamido)butanoyloxy) piperidin-1-yl)propyl)hexanoic acid;
2-amino-6-borono-2-(4-(piperazin-1-yl)butyl)hexanoic acid;
2-amino-6-borono-2-(4-(4-(3,4-dichlorophenyl)piperazin-1-yl)butyl)hexanoic acid;
2-amino-6-borono-2-(4-(4-(3,4-difluorobenzyl)piperidin-1-yl)butyl)hexanoic acid;
2-amino-6-borono-2-(4-(3,4-dihydroisoquinolin-2(1H)-yl)butyl)hexanoic acid;
2-amino-6-borono-2-(4-(2-(4-fluorophenyl)piperidin-1-yl)butyl)hexanoic acid;
2-amino-6-borono-2-(3-(carboxymethylamino)propyl) hexanoic acid;
2-amino-2-(3-(4-(biphenyl-4-ylmethyl)piperazin-1-yl) propyl)-6-boronohexanoic acid;
2-amino-2-(3-(4-benzhydrylpiperazin-1-yl)propyl)-6-boronohexanoic acid;
2-amino-6-borono-2-(3-(4-(4-fluorobenzoyl)piperidin-1-yl)propyl)hexanoic acid;
2-(3-(3-(1H-benzo[d]imidazol-1-yl)-8-azabicyclo[3.2.1] octan-8-yl)propyl)-2-amino-6-boronohexanoic acid;
2-amino-6-borono-2-(3-(4-(phenylamino)piperdin-1-yl) propyl)hexanoic acid;
2-amino-6-borono-2-(3-(4-(3,4-dichlorobenzylamino)piperidin-1-yl)propyl) hexanoic acid;

2-amino-6-borono-2-(3-(4-((3,4-dichlorobenzyl)(ethyl) amino)piperidin-1-yl) propyl)hexanoic acid;
2-amino-6-borono-2-(3-(4-methylpiperazin-1-yl)propyl) hexanoic acid;
2-amino-6-borono-2-(3-(3-fluoro-4-phenylpiperidin-1-yl)propyl)hexanoic acid;
2-amino-6-borono-2-(3-(4-(N-(3,4-dichlorobenzyl)octanamido)piperidin-1-yl)propyl)hexanoic acid;
2-amino-3-(3-(4-benzyl-4-(decanoyloxy)piperidin-1-yl) propyl)-6-boronohexanoic acid;
2-amino-2-(3-(3-(benzo[d]oxazol-2-yl)piperidin-1-yl) propyl)-6-boronohexanoic acid;
2-amino-6-borono-2-(3-(2-phenylpyrrolin-1-yl)propyl) hexanoic acid;
2-amino-6-borono-2-(3-(3-(3-(3,4-dichlorophenyl)ureido)pyrrolidin-1-yl)propyl) hexanoic acid;
2-amino-6-borono-2-(3-(3-(3-(4-fluorophenyl)ureido) pyrrolidin-1-yl)propyl) hexanoic acid;
2-amino-6-borono-2-(3-(3-(3,4-dichlorophenylsulfonamido)pyrrolidin-1-yl) propyl)hexanoic acid;
2-(3-(1H-imidazol-1-yl)propyl)-2-amino-6-boronohexanoic acid;
2-(3-(1H-benzo[d]imidazol-1-yl)propyl)-2-amino-6-boronohexanoic acid;
2-amino-6-borono-2-(3-(cyclopentylamino)propyl)hexanoic acid;
2-amino-6-borono-2-(3-(tetrahydro-2H-pyran-4-ylamino)propyl)hexanoic acid;
2-amino-6-borono-2-(3-((3R)-3-methoxytetrahydro-2H-pyran-4-ylamino)propyl) hexanoic acid;
2-amino-6-borono-2-(3-(methyl(naphthalen-2-ylmethyl) amino)propyl)hexanoic acid;
2-amino-6-borono-2-(3-(methyl((4-methylnaphthalen-1-yl)methyl)amino)propyl) hexanoic acid;
2-amino-6-borono-2-(3-((4-(3,4-dichlorophenoxy)benzyl)(methyl)amino)propyl) hexanoic acid;
2-amino-6-borono-2-(3-((3',4'-dichlorobiphenyl-4-yl)methyl)(methyl)amino) propyl)hexanoic acid;
2-amino-6-borono-2-(3-((3',4'-dichlorobiphenyl)-4-yl) methylamino)propyl) hexanoic acid;
(S)-2-amino-6-borono-2-(3-(1-carboxylethylamino)propyl)hexanoic acid;
(S)-2-amino-6-borono-2-(3-(1-carboxy-3-methylbutylamino)propyl)hexanoic acid;
2-amino-6-borono-2-(3-((S)-1-methoxy-1-oxopropan-2-ylamino)propyl)hexanoic acid;
(S)-2-amino-6-borono-2-(3-(1-methoxy-4-methyl-1-oxopentan-2-ylamino)propyl) hexanoic acid;
2-amino-6-borono-2-(3-(4-(3,4-dichlorobenzoyl)piperazin-1-yl)propyl)hexanoic acid;
2-amino-6-borono-2-(3-(4-(4-methoxybenzoyl)piperazin-1-yl)propyl)hexanoic acid;
2-amino-6-borono-2-(3-(4-(3-methoxybenzoyl)piperazin-1-yl)propyl)hexanoic acid;
2-amino-6-borono-2-(3-(4-(4-methylbenzoyl)piperazin-1-yl)propyl)hexanoic acid;
2-amino-6-borono-2-(3-(4-(4-fluorobenzoyl)piperazin-1yl)propyl)hexanoic acid;
2-amino-6-borono-2-(3-(4-(2-fluorobenzoyl)piperazin-1-yl)propyl)hexanoic acid;
2-amino-6-borono-2-(3-(4-(2-chlorobenzoyl)piperazin-1-yl)propyl)hexanoic acid;
2-amino-6-borono-2-(3-(4-(3-fluorobenzoyl)piperazin-1-yl)propyl)hexanoic acid;
2-amino-6-borono-2-(3-(4-4-(trifluoromethyl)benzoyl) piperazin-1-yl)propyl) hexanoic acid;
2-amino-6-borono-2-(3-(4-4-carbamoylbenzoyl)piperazin-1-yl)propyl)hexanoic acid;
2-amino-6-borono-2-(3-(4-3,4-dichlorophenylcarbamoyl) piperazin-1-yl)propyl) hexanoic acid;
2-amino-6-borono-2-(3-(4-2-fluorophenylcarbamoyl)piperazin-1-yl)propyl) hexanoic acid;
2-amino-6-borono-2-(3-(4-3-fluorophenylcarbamoyl)piperazin-1-yl)propyl) hexanoic acid;
2-amino-6-borono-2-(3-(4-4-fluorophenylcarbamoyl)piperazin-1-yl)propyl) hexanoic acid;
2-amino-6-borono-2-(3-(4-3,4-difluorophenylcarbamoyl) piperazin-1-yl)propyl hexanoic acid;
2-amino-6-borono-2-(3-(4-2,5-difluorophenylcarbamoyl) piperazin-1-yl)propyl) hexanoic acid;
2-amino-6-borono-2-(3-(4-2,4-difluorophenylcarbamoyl) piperazin-1-yl)propyl) hexanoic acid;
2-amino-6-borono-2-(3-(4-2,3-difluorophenylcarbamoyl) piperazin-1-yl)propyl) hexanoic acid;
2-amino-6-borono-2-(3-(4-3,5-difluorophenylcarbamoyl) piperazin-1-yl)propyl) hexanoic acid;
2-amino-6-borono-2-(3-(4-tosylpiperazin-1-yl)propyl) hexanoic acid;
2-amino-6-borono-2-(3-(4-4-fluorophenylsulfonyl)piperazin-1-yl)propyl) hexanoic acid;
2-amino-6-borono-2-(3-(4-3-fluorophenylsulfonyl)piperazin-1-yl)propyl) hexanoic acid;
2-amino-6-borono-2-(3-(4-3,4-dichlorophenylsulfonyl) piperazin-1-yl)propyl) hexanoic acid;
a salt thereof, an ester thereof and a mixture thereof.

2. A compound selected from the group consisting of:
5-amino-8-(4-(3,4-dichlorobenzyl)piperazin-1-yl)-5-(isopropoxycarbonyl)octylboronic acid;
5-amino-8-(4-(3,4-dichlorobenzyl)piperazin-1-yl)-5-(isopentyloxycarbonyl)octylboronic acid;
5-amino-8-(4-(3,4-dichlorobenzyl)piperazin-1-yl)-5-((2-(piperidin-1-yl)ethoxy) carbonyl) octylboronic acid;
5-amino-8-(4-(3,4-dichlorobenzyl)piperazin-1-yl)-5-((2-morpholinoethoxy) carbonyl) octylboronic acid;
5-amino-5-(methoxycarbonyl)-8-(4-(4-methylsulfonyl) benzyl)piperazin-1-yl)octylboronic acid;
5-amino-5-(ethoxycarbonyl)-8-(4-(4-(methylsulfonyl) benzyl)piperazin-1-yl)octylboronic acid;
5-amino-8-(4-(4-(methylsulfonyl)benzyl)piperazine-1-yl)-5-(propoxycarbonyl) octylboronic acid;
5-amino-5-(isopropoxycarbonyl)-8-(4-(4-(methylsulfonyl)benzyl)piperazin-1-yl)octylboronic acid;
5-amino-5-(isobutoxycarbonyl)-8-(4-(4-(methylsulfonyl) benzyl)piperazin-1-yl)octylboronic acid;
5-amino-5-(isopentyloxycarbonyl)-8-(4-(4-(methylsulfonyl)benzyl)piperazin-1-yl)octylboronic acid;
5-amino-8-(4-(4-(methylsulfonyl)benzyl)piperazin-1-yl)-5-((pentan-3-yloxy)carbonyl) octylboronic acid;
5-amino-5-((3-methylbutan-2-yloxy)carbonyl)-8-(4-(4-(methylsulfonyl) benzylpiperazin-1-yl) octylboronic acid;
5-amino-5-((2-methoxyethoxy)carbonyl)-8-(4-(4-(methylsulfonyl)benzyl) piperazin-1-yl) octylboronic acid;
5-amino-5-((2-hydroxyethoxy)carbonyl)-8-(4-(4-(methylsulfonyl)benzyl) piperazin-1-yl) octylboronic acid;
5-amino-8-(4-(4-(methylsulfonyl)benzyl)piperazine-1-yl-5((2-morpholinoethoxy)carbonyl) octylboronic acid;
5-amino-8-(4-(3,4-dichlorophenyl)piperazin-1-yl-5-(methoxycarbonyl) octylboronic acid;
a salt thereof and a mixture thereof.

* * * * *

UNITED STATES PATENT AND TRADEMARK OFFICE
CERTIFICATE OF CORRECTION

| | |
|---|---|
| PATENT NO. | : 8,894,970 B2 |
| APPLICATION NO. | : 13/191160 |
| DATED | : November 25, 2014 |
| INVENTOR(S) | : B. E. Tomczuk et al. |

It is certified that error appears in the above-identified patent and that said Letters Patent is hereby corrected as shown below:

IN THE SPECIFICATION

In column 128, Table 12, Comparative Example No. 4, "2-amino-6-borono-2-(3-(piperazin-1-yl)propylhexanoic acid" should be changed to --2-amino-6-borono-2-(3-(piperazin-1-yl)propyl)hexanoic acid--.

In column 128, Table 12, Example No. 8, "2-amino-6-borono-2-(3-(4-(3,4-dichlorobenzyl)piperazin-1-yl)hexanoic acid" should be changed to --2-amino-6-borono-2-(3-(4-(3,4-dichlorobenzyl)piperazin-1-yl)propyl)hexanoic acid--.

In column 128, Table 12, Example No. 31, "2-amino-6-borono-2(3-(4-oxo-1-phenyl-1,3,8-triazaspiro[4.5]decan-8-yl)propylhexanoic acid" should be changed to --2-amino-6-borono-2-(3-(4-oxo-1-phenyl-1,3,8-triazaspiro[4.5]decan-8-yl)propyl)hexanoic acid--.

In column 128, Table 12, Example No. 36, "2-amino-6-borono-2-(3-(4-(4-fluorophenyl)piperidin-1-yl)propylhexanoic acid" should be changed to --2-amino-6-borono-2-(3-(4-(4-fluorophenyl)piperidin-1-yl)propyl)hexanoic acid--.

In column 129, Table 12, Example No. 62, "2-amino-6-borono-2-(3-(3-(-chloro-2-fluorobenzamido)azetidin-1-yl)propyl) hexanoic acid" should be changed to --2-amino-6-borono-2-(3-(3-(3-chloro-2-fluorophenyl)ureido)azetidin-1-yl)propyl)hexanoic acid--.

In column 129, Table 12, Example No. 66, "2-amino-6-borono-2-(3-(thiazolidin-2-yl)propyl)hexanoic acid" should be changed to --2-amino-6-borono-2-(3-(thiazolidin-3-yl)propyl)hexanoic acid--.

In column 129, Table 12, Example No. 68, "2-amino-6-boron-2-(3-(methyl(phenethyl)aminopropyl)hexanoic acid" should be changed to --2-amino-6-borono-2-(3-methyl(phenethyl)aminopropyl)hexanoic acid--.

Signed and Sealed this
Twenty-sixth Day of January, 2016

Michelle K. Lee
*Director of the United States Patent and Trademark Office*

CERTIFICATE OF CORRECTION (continued)
U.S. Pat. No. 8,894,970 B2

IN THE SPECIFICATION

In column 129, Table 12, Example No. 69, "2-amino-6-borono-2-(3-(ethyl(naphthalen-1-ylmethyl)amino)propyl)hexanoic acid" should be changed to --2-amino-6-borono-2-(3-(ethyl(naphthalen-2-ylmethyl)amino)propyl)hexanoic acid--.

In column 129, Table 12, Example No. 71, "2-amino-6-borono-2-(3-((cyclohexylmethyl)(ethyl)amino)propyl)hexanoic acid" should be changed to --2-amino-6-borono-2-(3-(ethyl(naphthalen-1-ylmethyl)amino)propyl)hexanoic acid--.

In column 129, Table 12, Example No. 73, "2-amino-2-(3-(benzyl(ethyl)amino)propyl)-6-boronohexanoic acid" should be changed to --2-amino-6-borono-2-(3-((3-chlorobenzyl)(methyl)amino)propyl)hexanoic acid--.

In column 129, Table 12, Example No. 79, "2-amino-6-borono-2-(3-(methyl(tetrahydro-2H-pyran-4-yl)amino)propyl)hexanoic acid" should be changed to --2-amino-6-borono-2-(3-((cyclohexylmethyl)(ethyl)amino)propyl)hexanoic acid--.

In column 129, Table 12, Example No. 81, "2-amino-6-borono-2-(3-((3-chlorobenzyl)(methyl)amino)propyl)hexanoic acid" should be changed to --2-amino-6-borono-2-(3-(methyl(tetrahydro-2H-pyran-4-yl)amino)propyl)hexanoic acid--.

In column 131, Table 12, Example No. 88, "2-amino-6-borono-2-(3-((2-(dimethylamino)ethyl(methyl)amino)propyl)hexanoic acid" should be changed to --2-amino-6-borono-2-(3-(2-(dimethylamino)ethyl(methyl)amino)propyl)hexanoic acid--.

In column 131, Table 12, Example No. 91, "2-amino-6-borono-2-(3-((1R,4R)-5-(3,4-dichlorophenylcarbamoyl)-2,5-diazabicyclo[2.2.2]heptan-2-yl)propyl)hexanoic acid" should be changed to --2-amino-6-borono-2-(3-((1R,4R)-5-(3,4-dichlorophenylcarbamoyl)-2,5-diazabicyclo[2.2.1]heptan-2-yl)propyl)hexanoic acid--.

In column 131, Table 12, Example No. 92, "2-amino-6-borono-2-(3-(4-((S)-3-methyl-2-((R)-4-((3R,5S,7R,8R,9S,10S,12S,13R,14S,17R)-3,7,12-trihydroxy-10,13-dimethylhexadecahydro-1H-cyclopenta[a]phenathren-17-yl)pentanamido)butanoyloxy)piperidin-1-yl)propyl)hexanoic acid" should be changed to --2-amino-6-borono-2-(3-(4-((R)-3-methyl-2-((S)-4-((3S,5R,7S,8S,9R,10R,13R,14R,17S)-3,7,13-trihydroxy-10-methylhexadecahydro-1H-cyclopenta[a]phenanthren-17-yl)pentanamido)butanoyloxy)piperidin-1-yl)propyl)hexanoic acid--.

In column 131, Table 12, Example No. 99, "2-amino-2-(3-(4-(biphenyl-4-ylmethyl)piperazin-1-yl)propyl-6-boronohexanoic acid" should be changed to --2-amino-2-(3-(4-(biphenyl-4-ylmethyl)piperazin-1-yl)propyl)-6-boronohexanoic acid--.

In column 131, Table 12, Example No. 103, "2-amino-6-borono-2(3-(4-(phenylamino)piperidin-1-yl)propyl)hexanoic acid" should be changed to --2-amino-6-borono-2-(3-(4-(phenylamino)piperidin-1-yl)propyl)hexanoic acid--.

CERTIFICATE OF CORRECTION (continued)
U.S. Pat. No. 8,894,970 B2

IN THE SPECIFICATION

In column 131, Table 12, Example No. 115, "2-(3-(1H-imidazol-1-yl)propyl-2-amino-6-boronohexanoic acid" should be changed to --2-(3-(1H-imidazol-1-yl)propyl)-2-amino-6-boronohexanoic acid--.

In column 131, Table 12, Example No. 124, "2-amino-6-borono-2-(3-((3',4'-dichlorobiphenyl)-4-yl)methylamino)propyl)hexanoic acid" should be changed to --2-amino-6-borono-2-(3-(((3',4'-dichlorobiphenyl-4-yl)methyl)amino)propyl)hexanoic acid--.

In column 131, Table 12, Example No. 125, "(S)-2-amino-6-borono-2-(3-(1-carboxylethylamino)propyl)hexanoic acid" should be changed to --2-amino-6-borono-2-(3-((S)-1-carboxyethylamino)propyl)hexanoic acid--.

In column 131, Table 12, Example No. 126, "(S)-2-amino-6-borono-2-(3-(1-carboxy-3-methylbutylamino)propyl)hexanoic acid" should be changed to --2-amino-6-borono-2-(3-((S)-1-carboxy-3-methylbutylamino)propyl)hexanoic acid--.

In column 133, Table 12, Example No. 128, "(S)-2-amino-6-borono-2-(3-(1-methoxy-4-methyl-1-oxopentan-2-ylamino)propyl)hexanoic acid" should be changed to --2-amino-6-borono-2-(3-((S)-1-methoxy-4-methyl-1-oxopentan-2-ylamino)propyl)hexanoic acid--.

In column 133, Table 12, Comparative Example No. 6, "2-amino-6-borono-2-(3-(4-(4-cyanobenzoyl)piperazin-1-yl)propylhexanoic acid" should be changed to --2-amino-6-borono-2-(3-(4-(4-cyanobenzoyl)piperazin-1-yl)propyl) hexanoic acid--.

In column 133, Table 12, Example No. 146, "2-amino-6-borono-2-(3-(4-(3,4-diflurorophenylcarbamoyl)piperazin-1-yl)propylhexanoic acid" should be changed to --2-amino-6-borono-2-(3-(4-(3,4-diflurorophenylcarbamoyl)piperazin-1-yl)propyl)hexanoic acid--.

In column 133, Table 12, Example No. 159, "5-amino-5-(methoxycarbonyl)-8-(4-(4-methylsulfonyl)benzyl)piperazin-1-yl)octylboronic acid" should be changed to --5-amino-5-(methoxycarbonyl)-8-(4-(4-(methylsulfonyl)benzyl)piperazin-1-yl)octylboronic acid--.

In column 135, Table 12, Example No. 166, "5-amino-5-((3-methylbutan-2-yloxy)carbonyl)-8-(4-(4-(methylsulfonyl)benzylpiperazin-1-yl)octylboronic acid" should be changed to --5-amino-5-((3-methylbutan-2-yloxy)carbonyl)-8-(4-(4-(methylsulfonyl)benzyl)piperazin-1-yl)octylboronic acid--.

In column 135, Table 12, Example No. 169, "5-amino-8-(4-(4-(methylsulfonyl)benzyl)piperazine-1-yl-5-((2-morpholinoethoxy)carbonyl)octylboronic acid" should be changed to --5-amino-8-(4-(4-(methylsulfonyl)benzyl)piperazine-1-yl-5-((2-morpholino)ethoxy)carbonyl)octylboronic acid--.

In column 135, Table 12, Example No. 170, "5-amino-8-(4-(3,4-dichlorophenyl)piperazin-1-yl-5-(methoxycarbonyl)octylboronic acid" should be changed to --5-amino-8-(4-(3,4-dichlorophenyl)piperazin-1-yl)-5-(methoxycarbonyl)octylboronic acid--.

CERTIFICATE OF CORRECTION (continued)
U.S. Pat. No. 8,894,970 B2

IN THE CLAIMS

In claim 1, column 138, lines 3-4, "2-amino-6-borono-2-(3-(4-(3,4-dichlorobenzyl)piperazin-1-yl)hexanoic acid" should be changed to --2-amino-6-borono-2-(3-(4-(3,4-dichlorobenzyl)piperazin-1-yl)propyl)hexanoic acid--.

In claim 1, column 138, lines 49-50, "2-amino-6-borono-2(3-(4-oxo-1-phenyl-1,3,8-triazaspiro[4.5]decan-8-yl)propyl) hexanoic acid" should be changed to --2-amino-6-borono-2-(3-(4-oxo-1-phenyl-1,3,8-triazaspiro[4.5]decan-8-yl)propyl) hexanoic acid--.

In claim 1, column 138, lines 59-60, "2-amino-6-borono-2-(3-(4-(4-fluorophenyl)piperidin-1-yl)propylhexanoic acid" should be changed to --2-amino-6-borono-2-(3-(4-(4-fluorophenyl)piperidin-1-yl)propyl)hexanoic acid--.

In claim 1, column 139, lines 19-22, "2-amino-6-borono-2-(3-(2-(3-methoxylphenyl)pyrrolidin-1l-yl)propyl)hexanoic acid 2-amino-6-borono-2-(3-(2-(2-fluorobenzyl)pyrrolidin-1-yl)propyl)hexanoic acid" should be changed to --2-amino-6-borono-2-(3-(2-(3-methoxylphenyl)pyrrolidin-1-yl)propyl)hexanoic acid;
2-amino-6-borono-2-(3-(2-(2-fluorobenzyl)pyrrolidin-1-yl)propyl)hexanoic acid--.

In claim 1, column 139, lines 45-46, "2-amino-6-borono-2-(3-(3-(-chloro-2-fluorobenzamido)azetidin-1-yl)propyl) hexanoic acid" should be changed to --2-amino-6-borono-2-(3-(3-(3-chloro-2-fluorophenyl)ureido)azetidin-1-yl)propyl)hexanoic acid--.

In claim 1, column 139, lines 52-54, "2-amino-6-borono-2-(3-(thiazolidin-2-yl)propyl)hexanoic acid" should be changed to --2-amino-6-borono-2-(3-(thiazolidin-3-yl)propyl)hexanoic acid--.

In claim 1, column 139, lines 56-57, "2-amino-6-borono-2-(3-(methyl(phenethyl)aminopropyl)hexanoic acid" should be changed to --2-amino-6-borono-2-(3-methyl(phenethyl)aminopropyl)hexanoic acid--.

In claim 1, column 139, lines 58-59, "2-amino-6-borono-2-(3-(ethyl(naphthalen-1-ylmethyl)amino)propyl)hexanoic acid" should be changed to --2-amino-6-borono-2-(3-(ethyl(naphthalen-2-ylmethyl)amino)propyl)hexanoic acid--.

In claim 1, column 139, lines 62-63, "2-amino-6-borono-2-(3-((cyclohexylmethyl)(ethyl)amino)propyl)hexanoic acid" should be changed to --2-amino-6-borono-2-(3-(ethyl(naphthalen-1-ylmethyl)amino)propyl)hexanoic acid--.

In claim 1, column 139, lines 66-67, "2-amino-2-(3-(benzyl(ethyl)amino)propyl)-6-boronohexanoic acid" should be changed to --2-amino-6-borono-2-(3-((3-chlorobenzyl)(methyl)amino)propyl)hexanoic acid--.

IN THE CLAIMS

In claim 1, column 140, lines 11-12, "2-amino-6-borono-2-(3-(methyl(tetrahydro-2H-pyran-4-yl)amino)propyl)hexanoic acid" should be changed to --2-amino-6-borono-2-(3-((cyclohexylmethyl)(ethyl)amino)propyl)hexanoic acid--.

In claim 1, column 140, lines 15-16, "2-amino-6-borono-2-(3-((3-chlorobenzyl)(methyl)amino)propyl)hexanoic acid" should be changed to --2-amino-6-borono-2-(3-(methyl(tetrahydro-2H-pyran-4-yl)amino)propyl)hexanoic acid--.

In claim 1, column 140, lines 29-30, "2-amino-6-borono-2-(3-((2-(dimethylamino)ethyl(methyl)amino)propyl)hexanoic acid" should be changed to --2-amino-6-borono-2-(3-(2-(dimethylamino)ethyl(methyl)amino)propyl)hexanoic acid--.

In claim 1, column 140, lines 35-37, "2-amino-6-borono-2-(3-((1R,4R)-5-(3,4-dichlorophenylcarbamoyl)-2,5-diazabicyclo[2.2.2]heptan-2-yl)propyl)hexanoic acid" should be changed to --2-amino-6-borono-2-(3-((1R,4R)-5-(3,4-dichlorophenylcarbamoyl)-2,5-diazabicyclo[2.2.1]heptan-2-yl)propyl)hexanoic acid--.

In claim 1, column 140, lines 38-42, "2-amino-6-borono-2-(3-(4-((S)-3-methyl-2-4((R)-4-((3R,5S,7R,8R,9S,10S,12S,13R,14S,17R)-3,7,12-trihydroxy-10,13-dimethylhexadecahydro-1H-cyclopenta[a]phenathren-17-yl)pentanamido)butanoyloxy)piperidin-1-yl)propyl)hexanoic acid" should be changed to --2-amino-6-borono-2-(3-(4-((R)-3-methyl-2-((S)-4-((3S,5R,7S,8S,9R,10R,13R,14R,17S)-3,7,13-trihydroxy-10-methylhexadecahydro-1H-cyclopenta[a]phenanthren-17-yl)pentanamido)butanoyloxy)piperidin-1-yl)propyl)hexanoic acid--.

In claim 1, column 140, lines 63-64, "2-amino-6-borono-2(3-(4-(phenylamino)piperidin-1-yl)propyl)hexanoic acid" should be changed to --2-amino-6-borono-2-(3-(4-(phenylamino)piperidin-1-yl)propyl)hexanoic acid--.

In claim 1, column 141, lines 37-38, "2-amino-6-borono-2-(3-((3',4'-dichlorobiphenyl-4-yl)methyl)(methyl)amino)propyl)hexanoic acid" should be changed to --2-amino-6-borono-2-(3-(((3',4'-dichlorobiphenyl-4-yl)methyl)(methyl)amino)propyl)hexanoic acid--.

In claim 1, column 141, lines 39-40, "2-amino-6-borono-2-(3-((3',4'-dichlorobiphenyl)-4-yl)methylamino)propyl)hexanoic acid" should be changed to --2-amino-6-borono-2-(3-(((3',4'-dichlorobiphenyl-4-yl)methyl)amino)propyl)hexanoic acid--.

In claim 1, column 141, lines 41-42, "(S)-2-amino-6-borono-2-(3-(1-carboxylethylamino)propyl)hexanoic acid" should be changed to --2-amino-6-borono-2-(3-((S)-1-carboxyethylamino)propyl)hexanoic acid--.

In claim 1, column 141, lines 43-44, "(S)-2-amino-6-borono-2-(3-(1-carboxy-3-methylbutylamino)propyl)hexanoic acid" should be changed to --2-amino-6-borono-2-(3-((S)-1-carboxy-3-methylbutylamino)propyl)hexanoic acid--.

IN THE CLAIMS

In claim 1, column 141, lines 47-48, "(S)-2-amino-6-borono-2-(3-(1-methoxy-4-methyl-1-oxopentan-2-ylamino)propyl)hexanoic acid" should be changed to --2-amino-6-borono-2-(3-((S)-1-methoxy-4-methyl-1-oxopentan-2-ylamino)propyl)hexanoic acid--.

In claim 1, column 141, lines 65-66, "2-amino-6-borono-2-(3-(4-4-(trifluoromethyl)benzoyl)piperazin-1-yl)propyl)hexanoic acid" should be changed to --2-amino-6-borono-2-(3-(4-(4-(trifluoromethyl)benzoyl)piperazin-1-yl) propyl)hexanoic acid--.

In claim 1, column 142, lines 1-20,
"2-amino-6-borono-2-(3-(4-4-carbamoylbenzoyl)piperazin-1-yl)propyl)hexanoic acid;
2-amino-6-borono-2-(3-(4-3,4-dichlorophenylcarbamoyl)piperazin-1-yl)propyl)hexanoic acid;
2-amino-6-borono-2-(3-(4-2-fluorophenylcarbamoyl)piperazin-1-yl)propyl)hexanoic acid;
2-amino-6-borono-2-(3-(4-3-fluorophenylcarbamoyl)piperazin-1-yl)propyl)hexanoic acid;
2-amino-6-borono-2-(3-(4-4-fluorophenylcarbamoyl)piperazin-1-yl)propyl)hexanoic acid;
2-amino-6-borono-2-(3-(4-3,4-difluorophenylcarbamoyl)piperazin-1-yl)propyl hexanoic acid;
2-amino-6-borono-2-(3-(4-2,5-difluorophenylcarbamoyl)piperazin-1-yl)propyl) hexanoic acid;
2-amino-6-borono-2-(3-(4-2,4-difluorophenylcarbamoyl)piperazin-1-yl)propyl) hexanoic acid;
2-amino-6-borono-2-(3-(4-2,3-difluorophenylcarbamoyl)piperazin-1-yl)propyl) hexanoic acid;
2-amino-6-borono-2-(3-(4-3,5-difluorophenylcarbamoyl)piperazin-1-yl)propyl) hexanoic acid;"
should be changed to
--2-amino-6-borono-2-(3-(4-(4-carbamoylbenzoyl)piperazin-1-yl)propyl)hexanoic acid;
2-amino-6-borono-2-(3-(4-(3,4-dichlorophenylcarbamoyl)piperazin-1-yl)propyl)hexanoic acid;
2-amino-6-borono-2-(3-(4-(2-fluorophenylcarbamoyl)piperazin-1-yl)propyl)hexanoic acid;
2-amino-6-borono-2-(3-(4-(3-fluorophenylcarbamoyl)piperazin-1-yl)propyl)hexanoic acid;
2-amino-6-borono-2-(3-(4-(4-fluorophenylcarbamoyl)piperazin-1-yl)propyl)hexanoic acid;
2-amino-6-borono-2-(3-(4-(3,4-difluorophenylcarbamoyl)piperazin-1-yl)propyl) hexanoic acid;
2-amino-6-borono-2-(3-(4-(2,5-difluorophenylcarbamoyl)piperazin-1-yl)propyl) hexanoic acid;
2-amino-6-borono-2-(3-(4-(2,4-difluorophenylcarbamoyl)piperazin-1-yl)propyl) hexanoic acid;
2-amino-6-borono-2-(3-(4-(2,3-difluorophenylcarbamoyl)piperazin-1-yl)propyl) hexanoic acid;
2-amino-6-borono-2-(3-(4-(3,5-difluorophenylcarbamoyl)piperazin-1-yl)propyl) hexanoic acid;--.

In claim 1, column 142, lines 23-28,
"2-amino-6-borono-2-(3-(4-4-fluorophenylsulfonyl)piperazin-1-yl)propyl)hexanoic acid;
2-amino-6-borono-2-(3-(4-3-fluorophenylsulfonyl)piperazin-1-yl)propyl)hexanoic acid;
2-amino-6-borono-2-(3-(4-3,4-dichlorophenylsulfonyl)piperazin-1-yl)propyl)hexanoic acid;" should be changed to
--2-amino-6-borono-2-(3-(4-(4-fluorophenylsulfonyl)piperazin-1-yl)propyl)hexanoic acid;
2-amino-6-borono-2-(3-(4-(3-fluorophenylsulfonyl)piperazin-1-yl)propyl)hexanoic acid;
2-amino-6-borono-2-(3-(4-(3,4-dichlorophenylsulfonyl)piperazin-1-yl)propyl)hexanoic acid;--.

CERTIFICATE OF CORRECTION (continued)
U.S. Pat. No. 8,894,970 B2

IN THE CLAIMS

In claim 2, column 142, lines 39-40, "5-amino-5-(methoxycarbonyl)-8-(4-(4-methylsulfonyl)benzyl)piperazin-1-yl)octylboronic acid" should be changed to --5-amino-5-(methoxycarbonyl)-8-(4-(4-(methylsulfonyl)benzyl)piperazin-1-yl)octylboronic acid--.

In claim 2, column 142, lines 53-55, "5-amino-5-((3-methylbutan-2-yloxy)carbonyl)-8-(4-(4-(methylsulfonyl)benzylpiperazin-1-yl)octylboronic acid" should be changed to --5-amino-5-((3-methylbutan-2-yloxy)carbonyl)-8-(4-(4-(methylsulfonyl)benzyl)piperazin-1-yl)octylboronic acid--.

In claim 2, column 142, lines 60-61, "5-amino-8-(4-(4-(methylsulfonyl)benzyl)piperazine-1-yl-5-((2-morpholinoethoxy)carbonyl)octylboronic acid" should be changed to --5-amino-8-(4-(4-(methylsulfonyl)benzyl)piperazine-1-yl-5-((2-morpholino)ethoxy)carbonyl)octylboronic acid--.

In claim 2, column 142, lines 62-63, "5-amino-8-(4-(3,4-dichlorophenyl)piperazin-1-yl-5-(methoxycarbonyl)octylboronic acid" should be changed to --5-amino-8-(4-(3,4-dichlorophenyl)piperazin-1-yl)-5-(methoxycarbonyl)octylboronic acid--.